US011246776B2

(12) United States Patent
Moreno et al.

(10) Patent No.: US 11,246,776 B2
(45) Date of Patent: Feb. 15, 2022

(54) PATIENT SUPPORT WITH IMPROVED CONTROL

(71) Applicant: Stryker Corporation, Kalamazoo, MI (US)

(72) Inventors: David Mayen Moreno, Quebec (CA); David Kim Soui Wan Fong, Brossard (CA)

(73) Assignee: Stryker Corporation, Kalamazoo, MI (US)

(*) Notice: Subject to any disclaimer, the term of this patent is extended or adjusted under 35 U.S.C. 154(b) by 883 days.

(21) Appl. No.: 16/037,791

(22) Filed: Jul. 17, 2018

(65) Prior Publication Data

US 2019/0008708 A1    Jan. 10, 2019

Related U.S. Application Data

(63) Continuation of application No. 14/719,671, filed on May 22, 2015, now Pat. No. 10,052,249, which is a
(Continued)

(51) Int. Cl.
*A61G 7/018* (2006.01)
*A61G 7/015* (2006.01)
(Continued)

(52) U.S. Cl.
CPC .............. *A61G 7/018* (2013.01); *A61B 5/447* (2013.01); *A61B 5/6892* (2013.01); *A61G 7/005* (2013.01);
(Continued)

(58) Field of Classification Search
CPC ........ A61G 7/018; A61G 7/005; A61G 7/015; A61G 7/0524; A61G 13/02; A61G 13/04;
(Continued)

(56) References Cited

U.S. PATENT DOCUMENTS 3,599,199 A    8/1971  Bunting
3,962,615 A    6/1976  Spangler
(Continued)

FOREIGN PATENT DOCUMENTS

CA    2408342 A1    11/2001
EP    1149571 A2    10/2001
(Continued)

OTHER PUBLICATIONS

May 4, 2009 Office Action for Singaporean patent application serial No. 200803045.4, the national stage counterpart to PCT/US2006/043290 (which corresponds to U.S. Appl. No. 11/557,349).
(Continued)

*Primary Examiner* — Robert G Santos
(74) *Attorney, Agent, or Firm* — Warner Norcross + Judd LLP

(57) ABSTRACT

A braking system for a patient support apparatus includes a caster wheel assembly. The caster wheel assembly includes a caster wheel and manually operable brake operable to brake the caster wheel. The caster wheel assembly further includes a manual brake activation handle or pedal for manually operating the manually operable brake to move between three positions, wherein said three positions include a braking position, an un-braked position, and a steer lock position. The braking system further includes an electrically powered actuator mechanically coupled to the manual brake activation handle or pedal and to the manually operable brake. When powered, the electrically powered actuator is operable to move the manually operable brake and to move the manual brake activation handle or pedal between two or more of the three positions to thereby manually operate the caster wheel in a braking mode, an un-braked mode, or a steer lock mode. And, when the actuator is unpowered, the manual brake activation handle or pedal is operable to be
(Continued)

manually moved between two or more of the three positions to thereby manually operate the caster wheel in the braking mode, the un-braked mode, or the steer lock mode.

22 Claims, 61 Drawing Sheets

Related U.S. Application Data continuation-in-part of application No. 13/035,544, filed on Feb. 25, 2011, now Pat. No. 9,126,571, which is a continuation of application No. 11/642,047, filed on Dec. 19, 2006, now Pat. No. 7,962,981, said application No. 14/719,671 is a continuation of application No. 11/941,338, filed on Nov. 16, 2007, now Pat. No. 9,038,217, which is a continuation-in-part of application No. 11/642,047, filed on Dec. 19, 2006, now Pat. No. 7,962,981, said application No. 11/941,338 is a continuation-in-part of application No. 11/612,361, filed on Dec. 18, 2006, now Pat. No. 7,861,334, and a continuation-in-part of application No. 11/612,428, filed on Dec. 18, 2006, now Pat. No. 7,690,059, and a continuation-in-part of application No. 11/612,405, filed on Dec. 18, 2006, now Pat. No. 7,805,784.

(60) Provisional application No. 60/874,287, filed on Dec. 11, 2006, provisional application No. 60/751,770, filed on Dec. 19, 2005.

(51) Int. Cl.

| | | |
|---|---|---|
| *A61G 13/02* | (2006.01) | |
| *A61G 13/08* | (2006.01) | |
| *A61B 5/00* | (2006.01) | |
| *A61G 7/005* | (2006.01) | |
| *A61G 7/012* | (2006.01) | |
| *A61G 7/05* | (2006.01) | |
| *G16H 40/63* | (2018.01) | |
| *G16H 40/20* | (2018.01) | |
| *G16Z 99/00* | (2019.01) | |
| *G01G 19/44* | (2006.01) | |
| *G01G 19/52* | (2006.01) | |
| *G01G 23/32* | (2006.01) | |
| *G01G 23/42* | (2006.01) | |
| *G06F 3/0481* | (2013.01) | |
| *G06F 3/0484* | (2013.01) | |
| *G06F 3/0488* | (2013.01) | |
| *A61B 5/103* | (2006.01) | |
| *A61B 5/11* | (2006.01) | |
| *A61G 7/08* | (2006.01) | |

(52) U.S. Cl.
CPC .............. *A61G 7/012* (2013.01); *A61G 7/015* (2013.01); *A61G 7/0506* (2013.01); *A61G 7/0507* (2013.01); *A61G 7/0509* (2016.11); *A61G 7/0514* (2016.11); *A61G 7/0524* (2016.11); *A61G 7/0527* (2016.11); *A61G 7/0528* (2016.11); *G01G 19/44* (2013.01); *G01G 19/52* (2013.01); *G01G 23/32* (2013.01); *G01G 23/42* (2013.01); *G06F 3/0488* (2013.01); *G06F 3/04817* (2013.01); *G06F 3/04842* (2013.01); *G16H 40/20* (2018.01); *G16H 40/63* (2018.01); *G16Z 99/00* (2019.02); *A61B 5/103* (2013.01); *A61B 5/11* (2013.01); *A61B 5/743* (2013.01); *A61B 5/7435* (2013.01); *A61G 7/08* (2013.01); *A61G 2203/16* (2013.01); *A61G 2203/20* (2013.01); *A61G 2203/32* (2013.01); *A61G 2203/42* (2013.01); *A61G 2210/50* (2013.01)

(58) Field of Classification Search
CPC . A61G 13/08; A61G 2203/20; A61G 2203/42
USPC .............................................. 5/613, 616, 617
See application file for complete search history.

(56) References Cited

U.S. PATENT DOCUMENTS

| | | |
|---|---|---|
| 4,038,709 A | 8/1977 | Kerwit |
| 4,067,005 A | 1/1978 | Levy et al. |
| 4,183,015 A | 1/1980 | Drew et al. |
| 4,196,425 A | 4/1980 | Williams, Jr. et al. |
| 4,264,904 A | 4/1981 | McCoy et al. |
| 4,295,133 A | 10/1981 | Vance |
| 4,435,862 A | 3/1984 | King et al. |
| 4,494,259 A | 1/1985 | Miller et al. |
| 4,633,237 A | 12/1986 | Tucknott et al. |
| 4,680,790 A | 7/1987 | Packard et al. |
| 4,700,180 A | 10/1987 | Vance |
| 4,751,754 A | 6/1988 | Bailey et al. |
| 4,882,566 A | 11/1989 | Koerber, Sr. et al. |
| 4,907,845 A | 3/1990 | Wood |
| 4,953,243 A | 9/1990 | Birkmann |
| 4,998,939 A | 3/1991 | Potthast et al. |
| 5,137,033 A | 8/1992 | Norton |
| 5,161,274 A | 11/1992 | Hayes et al. |
| 5,161,535 A | 11/1992 | Short et al. |
| 5,181,288 A | 1/1993 | Heaton et al. |
| 5,184,112 A | 2/1993 | Gusakov |
| 5,195,198 A | 3/1993 | Travis |
| 5,205,004 A | 4/1993 | Hayes et al. |
| 5,239,300 A | 8/1993 | Berger et al. |
| 5,276,432 A | 1/1994 | Travis |
| 5,319,355 A | 6/1994 | Russek |
| 5,319,363 A | 6/1994 | Welch et al. |
| 5,325,551 A | 7/1994 | Tappel et al. |
| 5,393,938 A | 2/1995 | Bumbalough |
| 5,411,457 A | 5/1995 | Hartdegen, III et al. |
| 5,444,880 A | 8/1995 | Weismiller et al. |
| 5,450,639 A | 9/1995 | Weismiller et al. |
| 5,502,853 A | 4/1996 | Singleton et al. |
| 5,542,138 A | 8/1996 | Williams et al. |
| 5,559,301 A | 9/1996 | Bryan, Jr. et al. |
| 5,561,412 A | 10/1996 | Novak et al. |
| 5,592,153 A | 1/1997 | Welling et al. |
| 5,596,437 A | 1/1997 | Heins |
| 5,611,096 A | 3/1997 | Bartlett et al. |
| 5,664,270 A | 9/1997 | Bell et al. |
| 5,687,438 A | 11/1997 | Biggie et al. |
| 5,689,839 A | 11/1997 | Laganiere et al. |
| 5,699,038 A | 12/1997 | Ulrich et al. |
| 5,715,548 A | 2/1998 | Weismiller et al. |
| 5,745,937 A | 5/1998 | Weismiller et al. |
| 5,771,511 A | 6/1998 | Kummer et al. |
| 5,774,914 A | 7/1998 | Johnson et al. |
| 5,833,623 A | 11/1998 | Mann et al. |
| 5,854,454 A | 12/1998 | Upender et al. |
| 5,862,549 A * | 1/1999 | Morton .................. A61G 7/015 5/610 |
| 5,887,302 A | 3/1999 | DiMucci et al. |
| 5,926,002 A | 7/1999 | Cavanaugh et al. |
| 5,926,878 A * | 7/1999 | Morton ................ A61G 7/0514 5/624 |
| 5,971,091 A | 10/1999 | Kamen et al. |
| 6,000,076 A | 12/1999 | Webster et al. |
| 6,008,598 A | 12/1999 | Luff et al. |
| 6,014,346 A | 1/2000 | Malone |
| 6,014,784 A | 1/2000 | Taylor et al. |
| 6,047,424 A | 4/2000 | Osborne et al. |
| 6,119,291 A | 9/2000 | Osborne et al. |
| 6,163,903 A | 12/2000 | Weismiller et al. |
| 6,188,407 B1 | 2/2001 | Smith et al. |
| 6,226,819 B1 | 5/2001 | Ogawa et al. |

(56) References Cited

U.S. PATENT DOCUMENTS

| | | |
|---|---|---|
| 6,240,579 B1 | 6/2001 | Hanson et al. |
| 6,279,183 B1 | 8/2001 | Kummer et al. |
| 6,286,183 B1 | 9/2001 | Stickel et al. |
| 6,320,510 B2 | 11/2001 | Menkedick et al. |
| 6,321,878 B1 | 11/2001 | Mobley et al. |
| 6,351,678 B1 | 2/2002 | Borders |
| 6,353,950 B1 | 3/2002 | Bartlett et al. |
| 6,378,152 B1 | 4/2002 | Washburn et al. |
| 6,396,224 B1 | 5/2002 | Luff et al. |
| 6,397,286 B1 | 5/2002 | Chatenever et al. |
| 6,462,500 B1 | 10/2002 | L'Hegarat et al. |
| 6,467,111 B1 | 10/2002 | Vrzalik et al. |
| 6,473,921 B2 | 11/2002 | Brooke et al. |
| 6,481,688 B1 | 11/2002 | Welling et al. |
| 6,487,735 B1 | 12/2002 | Jacques, II et al. |
| 6,493,568 B1 | 12/2002 | Bell et al. |
| 6,529,144 B1 | 3/2003 | Nilsen et al. |
| 6,536,056 B1 | 3/2003 | Vrzalik et al. |
| 6,566,833 B2 | 5/2003 | Bartlett |
| 6,584,628 B1 | 7/2003 | Kummer et al. |
| 6,611,979 B2 | 9/2003 | Welling et al. |
| 6,658,680 B2 | 12/2003 | Osborne et al. |
| 6,668,965 B2 | 12/2003 | Strong |
| 6,671,905 B2 | 1/2004 | Bartlett et al. |
| RE38,419 E | 2/2004 | Auer et al. |
| 6,691,346 B2 | 2/2004 | Osborne et al. |
| 6,735,799 B1 | 5/2004 | Ellis et al. |
| 6,761,344 B2 | 7/2004 | Welling et al. |
| 6,781,517 B2 | 8/2004 | Moster et al. |
| 6,789,280 B1 | 9/2004 | Paul |
| 6,791,460 B2 | 9/2004 | Dixon et al. |
| 6,822,571 B2 | 11/2004 | Conway |
| 6,829,796 B2 | 12/2004 | Salvatini et al. |
| 6,865,775 B2 | 3/2005 | Ganance |
| 6,880,189 B2 | 4/2005 | Welling et al. |
| 6,892,405 B1 | 5/2005 | Dimitriu et al. |
| 6,897,780 B2 | 5/2005 | Ulrich et al. |
| 6,941,598 B2 | 9/2005 | Ferrand et al. |
| 6,957,461 B2 | 10/2005 | Osborne et al. |
| 6,978,500 B2 | 12/2005 | Osborne et al. |
| 7,010,369 B2 | 3/2006 | Borders et al. |
| 7,014,000 B2 | 3/2006 | Kummer et al. |
| 7,017,208 B2 | 3/2006 | Weismiller et al. |
| 7,038,588 B2 | 5/2006 | Boone et al. |
| 7,055,195 B2 | 6/2006 | Roussy |
| 7,081,091 B2 | 7/2006 | Merrett et al. |
| 7,086,103 B2 | 8/2006 | Barthelt |
| 7,100,222 B2 | 9/2006 | Metz et al. |
| 7,154,397 B2 | 12/2006 | Zerhusen et al. |
| 7,171,708 B2 | 2/2007 | Osborne et al. |
| 7,200,882 B2 | 4/2007 | Heimbrock |
| 7,296,312 B2 | 11/2007 | Menkedick et al. |
| 7,302,717 B2 | 12/2007 | Reinke et al. |
| 7,322,947 B2 | 1/2008 | Flick et al. |
| 7,406,731 B2 | 8/2008 | Menkedick et al. |
| 7,454,805 B2 | 11/2008 | Osborne et al. |
| 7,472,439 B2 | 1/2009 | Lemire et al. |
| 7,506,390 B2 | 3/2009 | Dixon et al. |
| 7,520,006 B2 | 4/2009 | Menkedick et al. |
| 7,533,429 B2 | 5/2009 | Menkedick et al. |
| 7,533,742 B2 | 5/2009 | Johnson et al. |
| 7,594,286 B2 | 9/2009 | Williams |
| 7,610,637 B2 | 11/2009 | Menkedick et al. |
| 7,644,457 B2 | 1/2010 | Hensley et al. |
| 7,679,520 B2 | 3/2010 | Zerhusen et al. |
| 7,690,059 B2 | 4/2010 | Lemire et al. |
| 7,699,784 B2 | 4/2010 | Wan Fong et al. |
| 7,716,762 B2 | 5/2010 | Ferraresi et al. |
| 7,761,942 B2 | 7/2010 | Benzo et al. |
| 7,779,493 B2 | 8/2010 | Lemire et al. |
| 7,805,784 B2 | 10/2010 | Lemire et al. |
| 7,836,531 B2 | 11/2010 | Girard et al. |
| 7,861,334 B2 | 1/2011 | Lemire et al. |
| 7,886,380 B2 | 2/2011 | Hornbach et al. |
| 7,962,981 B2 | 6/2011 | Lemire et al. |
| 8,117,701 B2 | 2/2012 | Bobey et al. |
| 8,344,860 B2 | 1/2013 | Collins, Jr. et al. |
| 8,393,026 B2 | 3/2013 | Dionne et al. |
| 8,413,271 B2 | 4/2013 | Blanchard et al. |
| 8,452,508 B2 | 5/2013 | Frolik et al. |
| 8,464,380 B2 | 6/2013 | Bobey et al. |
| 8,537,008 B2 | 9/2013 | Tallent et al. |
| 8,544,126 B2 | 10/2013 | Elliott et al. |
| 8,593,284 B2 | 11/2013 | Tallent et al. |
| 8,689,376 B2 | 4/2014 | Becker et al. |
| 8,701,229 B2 | 4/2014 | Lemire et al. |
| 8,717,181 B2 | 5/2014 | Tallent et al. |
| 8,720,616 B2 | 5/2014 | Kofoed et al. |
| 8,789,222 B2 | 7/2014 | Blanchard et al. |
| 8,844,076 B2 | 9/2014 | Becker et al. |
| 8,847,756 B2 | 9/2014 | Tallent et al. |
| 9,038,217 B2 | 5/2015 | Elliot et al. |
| 9,126,571 B2 | 9/2015 | Lemire et al. |
| 9,228,885 B2 | 1/2016 | Zerhusen et al. |
| 9,492,341 B2 | 11/2016 | Huster et al. |
| 9,539,156 B2 | 1/2017 | Lemire et al. |
| 9,555,778 B2 | 1/2017 | Lemire et al. |
| 9,618,383 B2 | 4/2017 | Zerhusen et al. |
| 9,642,759 B2 | 5/2017 | Stryker et al. |
| 9,815,439 B2 | 11/2017 | Lemire et al. |
| 10,403,401 B2 * | 9/2019 | Brosnan ................. G16H 40/67 |
| 2001/0011393 A1 | 8/2001 | Brooke et al. |
| 2001/0032362 A1 | 10/2001 | Welling et al. |
| 2002/0002742 A1 | 1/2002 | Osborne et al. |
| 2002/0044059 A1 | 4/2002 | Reeder et al. |
| 2002/0059679 A1 | 5/2002 | Weismiller et al. |
| 2002/0066142 A1 | 6/2002 | Osborne et al. |
| 2002/0080037 A1 | 6/2002 | Dixon et al. |
| 2002/0138905 A1 | 10/2002 | Bartlett et al. |
| 2002/0151990 A1 | 10/2002 | Ulrich et al. |
| 2004/0034936 A1 | 2/2004 | Welling et al. |
| 2004/0103475 A1 | 6/2004 | Ogawa et al. |
| 2004/0128765 A1 | 7/2004 | Osborne et al. |
| 2004/0177445 A1 | 9/2004 | Osborne et al. |
| 2004/0227737 A1 | 11/2004 | Novak et al. |
| 2005/0035871 A1 | 2/2005 | Dixon et al. |
| 2005/0165325 A1 | 7/2005 | Hornig |
| 2005/0166324 A1 | 8/2005 | Dixon et al. |
| 2005/0172405 A1 | 8/2005 | Menkedick et al. |
| 2005/0188462 A1 | 9/2005 | Heimbrock |
| 2005/0219059 A1 | 10/2005 | Ulrich et al. |
| 2006/0049936 A1 | 3/2006 | Collins, Jr. et al. |
| 2006/0053555 A1 | 3/2006 | Poulos et al. |
| 2006/0075560 A1 | 4/2006 | Osborne et al. |
| 2006/0096029 A1 | 5/2006 | Osborne et al. |
| 2006/0101581 A1 | 5/2006 | Blanchard et al. |
| 2006/0117482 A1 | 6/2006 | Branson |
| 2006/0162079 A1 | 7/2006 | Menkedick et al. |
| 2006/0168730 A1 | 8/2006 | Menkedick et al. |
| 2006/0168731 A1 | 8/2006 | Menkedick et al. |
| 2006/0271207 A1 | 11/2006 | Shaw |
| 2006/0277683 A1 | 12/2006 | Lemire et al. |
| 2006/0279427 A1 | 12/2006 | Becker et al. |
| 2007/0076852 A1 | 4/2007 | Ishikawa et al. |
| 2007/0130692 A1 | 6/2007 | Lemire et al. |
| 2007/0157385 A1 | 7/2007 | Lemire et al. |
| 2007/0163043 A1 | 7/2007 | Lemire et al. |
| 2007/0163045 A1 | 7/2007 | Becker et al. |
| 2007/0164871 A1 | 7/2007 | Dionne et al. |
| 2007/0169268 A1 | 7/2007 | Lemire et al. |
| 2007/0174964 A1 | 8/2007 | Lemire et al. |
| 2007/0174965 A1 | 8/2007 | Lemire et al. |
| 2007/0180616 A1 | 8/2007 | Newkirk et al. |
| 2007/0210917 A1 | 9/2007 | Collins, Jr. et al. |
| 2007/0296600 A1 | 12/2007 | Dixon et al. |
| 2008/0005838 A1 | 1/2008 | Wan Fong et al. |
| 2008/0010747 A1 | 1/2008 | Dixon et al. |
| 2008/0010748 A1 | 1/2008 | Menkedick et al. |
| 2008/0097177 A1 | 4/2008 | Music et al. |
| 2008/0172789 A1 | 7/2008 | Elliot et al. |
| 2008/0201847 A1 | 8/2008 | Menkedick et al. |
| 2008/0201851 A1 | 8/2008 | Menkedick et al. |
| 2008/0235872 A1 | 10/2008 | Newkirk et al. |
| 2008/0289108 A1 | 11/2008 | Menkedick et al. |

(56) References Cited

U.S. PATENT DOCUMENTS

| | | |
|---|---|---|
| 2009/0031498 A1 | 2/2009 | Girard et al. |
| 2009/0089930 A1 | 4/2009 | Benzo et al. |
| 2009/0094744 A1 | 4/2009 | Benzo et al. |
| 2009/0094745 A1 | 4/2009 | Benzo et al. |
| 2009/0094746 A1 | 4/2009 | Ferraresi et al. |
| 2009/0237264 A1 | 9/2009 | Bobey et al. |
| 2010/0000018 A1 | 1/2010 | Eleonori et al. |
| 2010/0073168 A1 | 3/2010 | Tallent et al. |
| 2010/0275376 A1 | 11/2010 | Benzo et al. |
| 2011/0144548 A1 | 6/2011 | Elliott et al. |
| 2011/0162141 A1 | 7/2011 | Lemire et al. |
| 2011/0231996 A1 | 9/2011 | Lemire et al. |
| 2011/0277242 A1 | 11/2011 | Dionne et al. |
| 2012/0025992 A1 | 2/2012 | Tallent et al. |
| 2012/0089419 A1 | 4/2012 | Huster et al. |
| 2012/0105233 A1 | 5/2012 | Bobey et al. |
| 2013/0007963 A1 | 1/2013 | Tallent et al. |
| 2013/0219628 A1 | 8/2013 | Blanchard et al. |
| 2013/0276237 A1 | 10/2013 | Bobey et al. |
| 2013/0340169 A1 | 12/2013 | Zerhusen et al. |
| 2014/0015677 A1 | 1/2014 | Tallent et al. |
| 2014/0059768 A1 | 3/2014 | Lemire et al. |
| 2014/0124274 A1 | 5/2014 | Zerhusen et al. |
| 2014/0137322 A1 | 5/2014 | Becker et al. |
| 2014/0237721 A1 | 8/2014 | Lemire et al. |
| 2014/0259410 A1 | 9/2014 | Zerhusen et al. |
| 2015/0000035 A1 | 1/2015 | Becker et al. |
| 2015/0135436 A1 | 5/2015 | Stryker et al. |
| 2015/0250669 A1 | 9/2015 | Elliott et al. |
| 2016/0095774 A1 | 4/2016 | Bobey et al. |
| 2016/0140307 A1* | 5/2016 | Brosnan .............. A61H 23/006 600/324 |
| 2016/0287459 A1 | 10/2016 | Lemire et al. |
| 2017/0027787 A1 | 2/2017 | Huster et al. |
| 2017/0124844 A1 | 5/2017 | Huster et al. |
| 2017/0172828 A1 | 6/2017 | Zerhusen et al. |
| 2017/0202728 A1 | 7/2017 | Stryker et al. |
| 2017/0224562 A1 | 8/2017 | Zerhusen et al. |
| 2018/0104122 A9 | 4/2018 | Elliott et al. |
| 2018/0161225 A1 | 6/2018 | Zerhusen et al. |
| 2020/0188204 A1* | 6/2020 | Newkirk ............. G06F 3/04847 |
| 2020/0197247 A1* | 6/2020 | Nahavandi ............. G16H 40/67 |

FOREIGN PATENT DOCUMENTS

| | | | |
|---|---|---|---|
| EP | 0838354 | B1 | 4/2002 |
| EP | 1199027 | A2 | 4/2002 |
| EP | 1354539 | A1 | 10/2003 |
| EP | 1477110 | A1 | 11/2004 |
| EP | 1616718 | A2 | 1/2006 |
| EP | 3127522 | A1 * | 2/2017 ............. A61G 7/018 |
| EP | 3127522 | B1 * | 6/2019 ............. A61G 7/005 |
| EP | 3563819 | A1 * | 11/2019 ........... A61G 7/1046 |
| GB | 2261173 | A | 5/1993 |
| JP | 7-107195 | A | 4/1995 |
| JP | 11-290395 | A | 10/1999 |
| JP | 2005-185346 | A | 7/2005 |
| KR | 200366830 | Y1 | 11/2004 |
| WO | 0175834 | A1 | 10/2001 |
| WO | 0185085 | A2 | 11/2001 |
| WO | 02084903 | A1 | 10/2002 |
| WO | 03/018087 | A2 | 3/2003 |
| WO | 2004006768 | A1 | 1/2004 |
| WO | 2004028344 | A2 | 4/2004 |
| WO | 2004093023 | A2 | 10/2004 |
| WO | WO-2007075701 | A2 * | 7/2007 ............... A61G 7/05 |
| WO | 2008/042121 | A2 | 4/2008 |

OTHER PUBLICATIONS

Partial Search Report for PCT/US2006/043290 (which corresponds to U.S. Appl. No. 11/557,349), dated Mar. 14, 2007.
PCT Written Opinion of the International Searching Authority regarding PCT/US06/043290.
Stryker Adel 500XL Childbearing Bed Service Manual, Adel Medical Ltd. 1986.
Adel Maternity Bed Model 4700 & 5012 Operations Manual, Oct. 2003.
Advantage Stretchers Stryker Patient Handling, May 1994.
Stryker Medical Labor & Delivery Model 5000 Series, Oct. 1996.
Hausted Gemini Series, Hausted, Inc., Oct. 1993.
Stryker Adel 2100EC Childbearing Bed, Stryker Patient Care, Jan. 1994.
Adel 500XL Childbearing Bed, Stryker Patient Care, May 1995.
Mar. 19, 2010 Office Action for Singaporean patent application serial No. 200803045.4, the national stage counterpart to PCT/US2006/043290 (which corresponds to U.S. Appl. No. 11/557,349).
Claims of Singapore Application No. 2008/03045.4 as of Mar. 22, 2010.
European Office Action for EP Application No. 06827596.5, dated Oct. 13, 2009 (the regional stage counterpart of PCT/US2006/043290, which corresponds to U.S. Appl. No. 11/557,349).
Gaymar AIRE-TWIN Operator's Manual for Alternating Pressure and Low-Air-Loss Therapy, and Mattress Replacement Systems, May 2005.
Plexus Medical Service Manual for 02 Zoned C4000 Portable Rotation System and CareMedx C5000 Multi-zoned Low Air Loss Therapy System, Apr. 2003.
Stryker Modular Patient System (MPS) 3000 bed, Maintenance Manual, 1994.

* cited by examiner

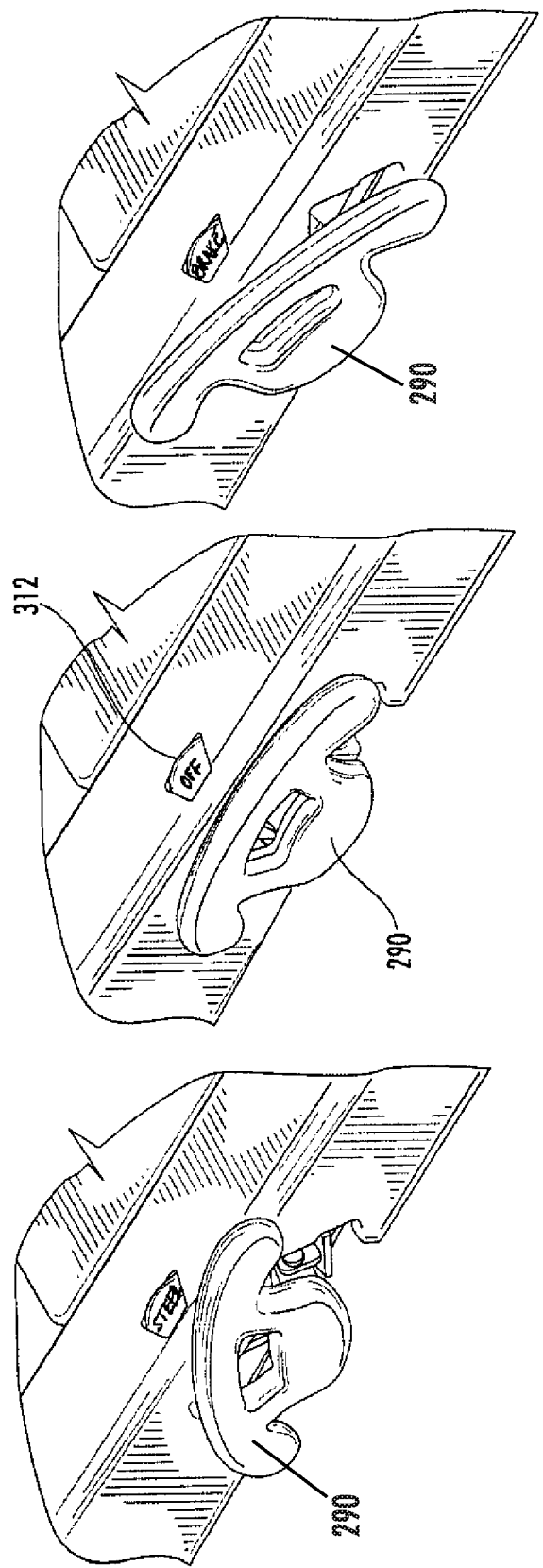

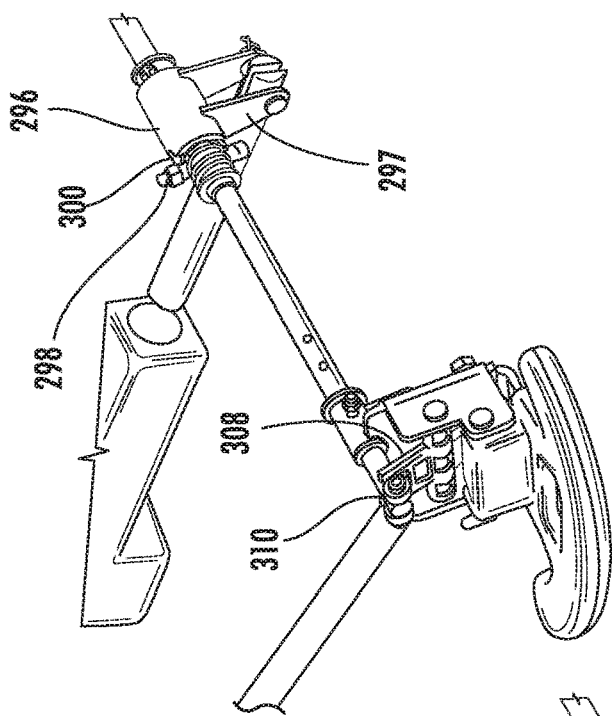
FIG. 15I
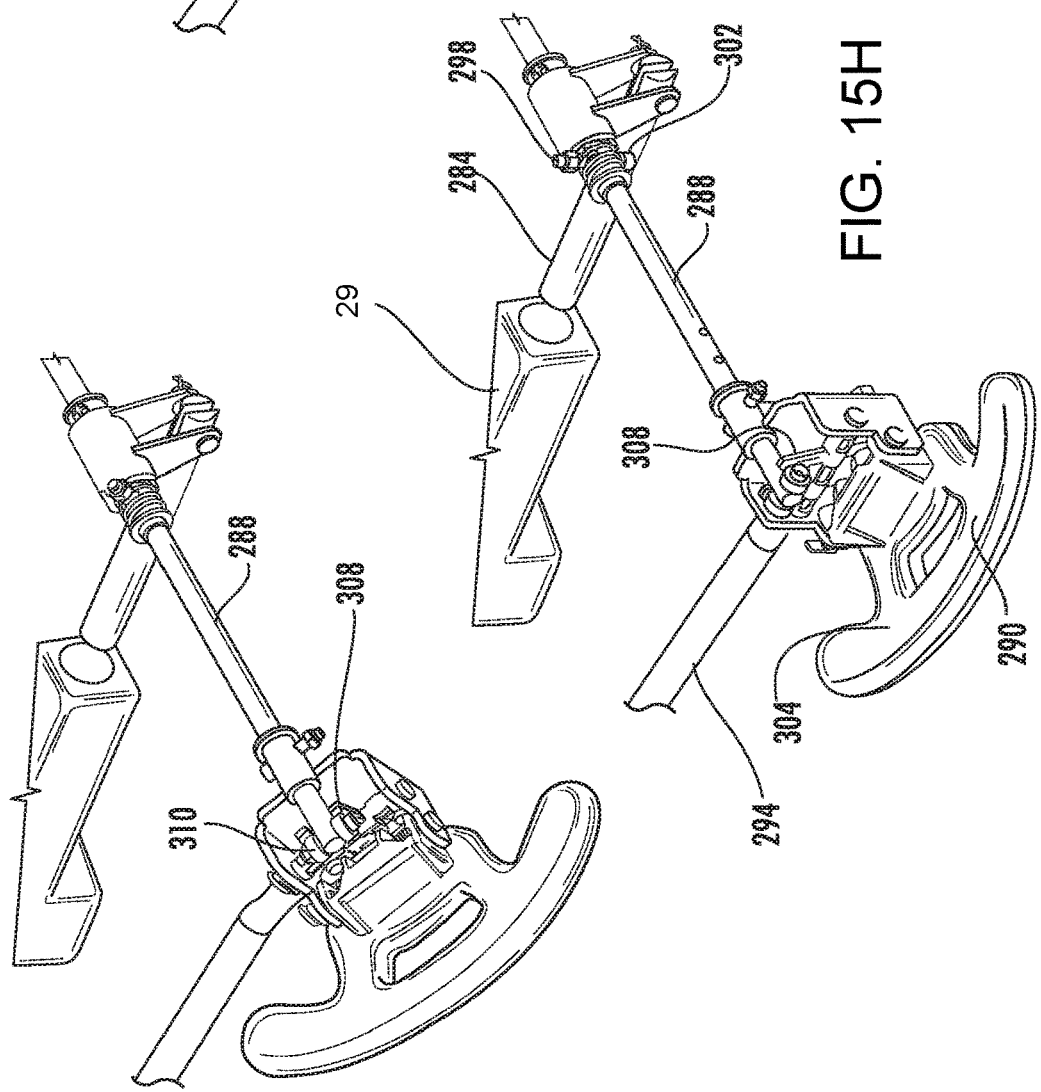
FIG. 15H
FIG. 15G

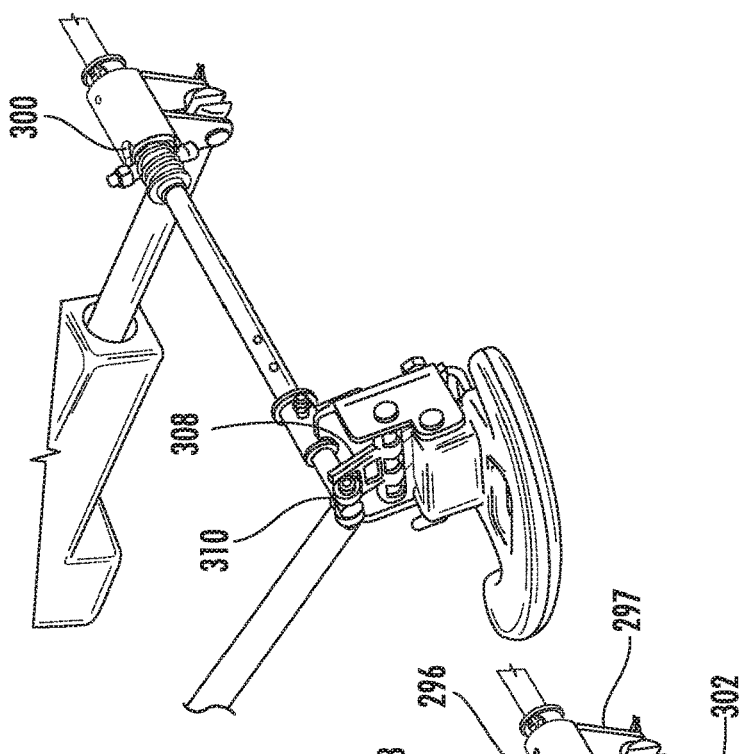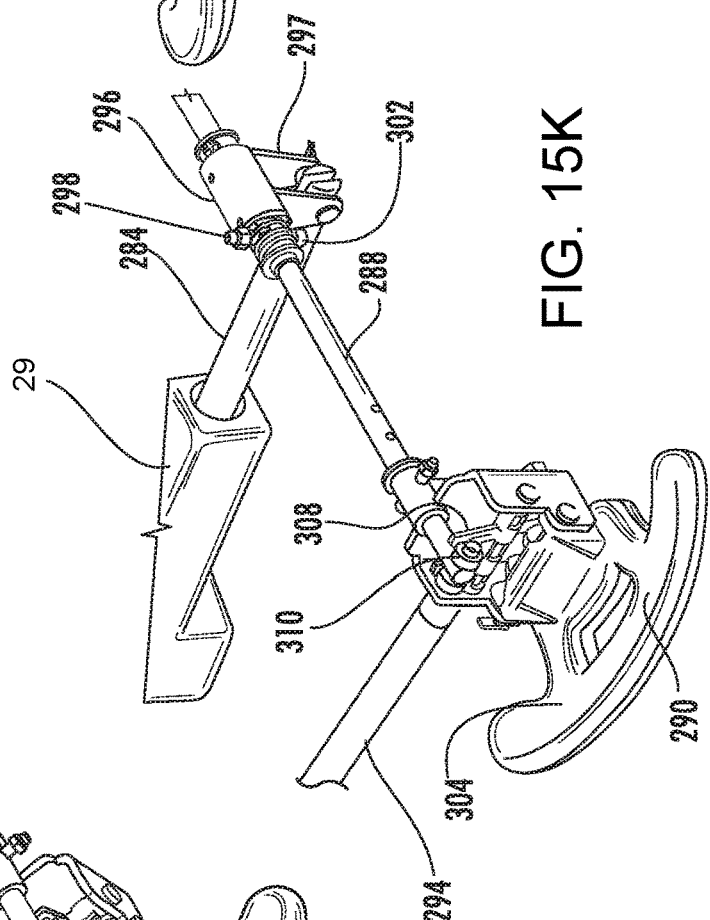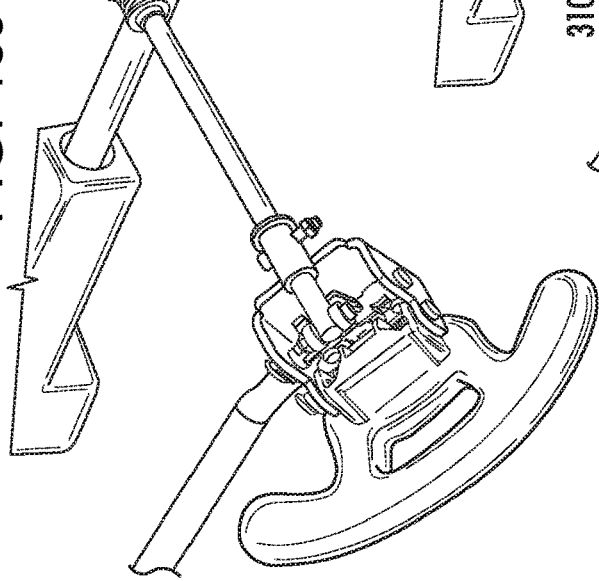

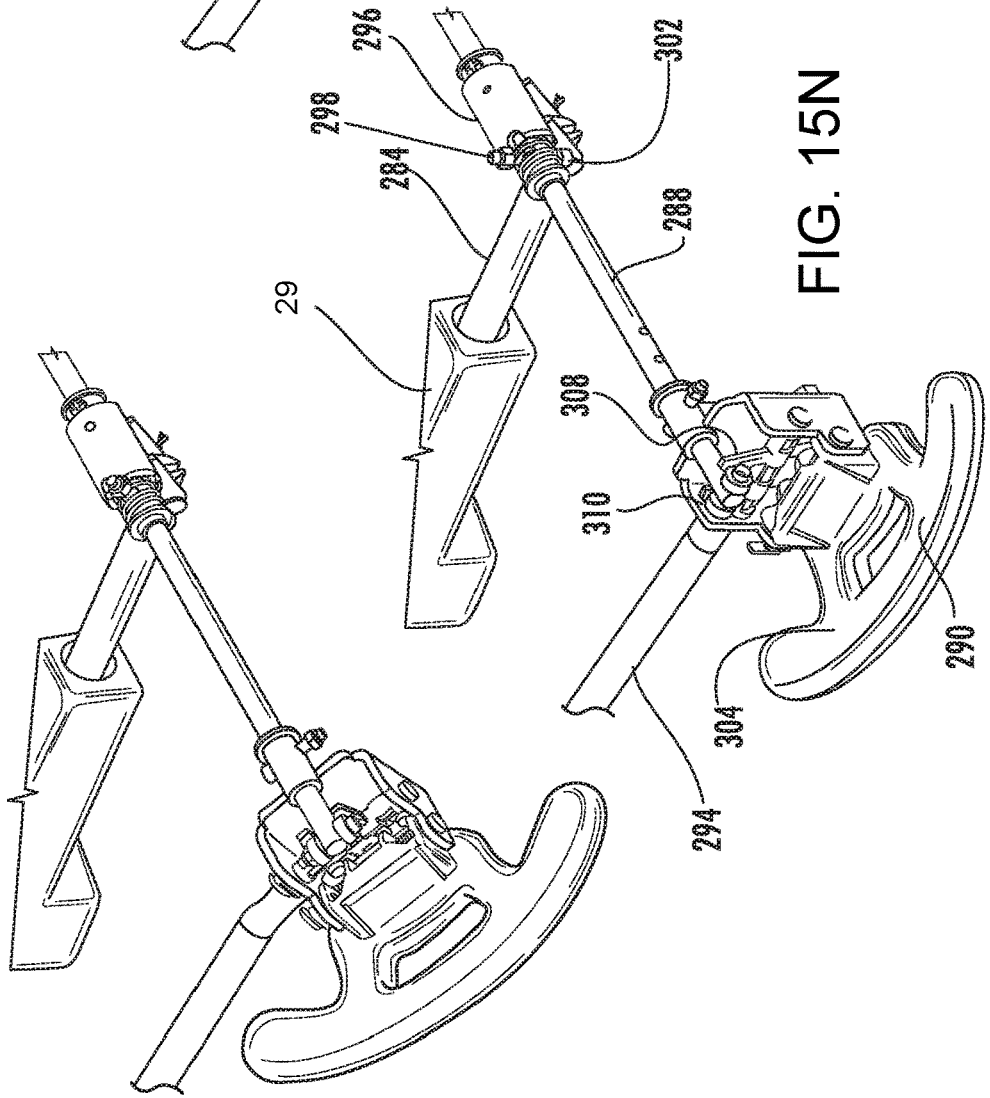

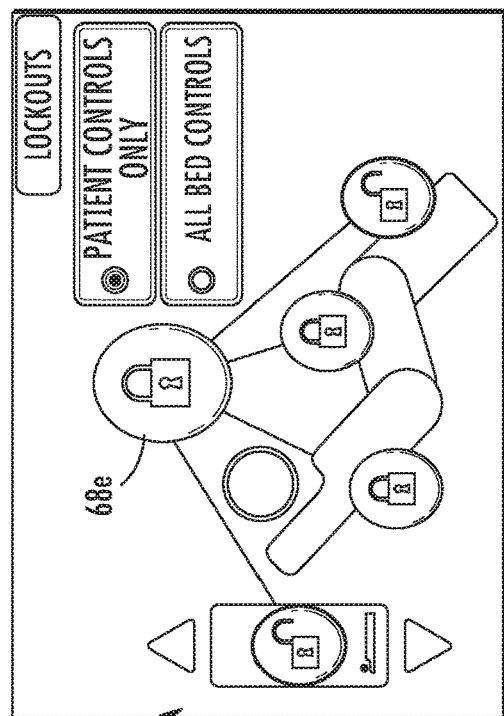
*FIG. 31B*
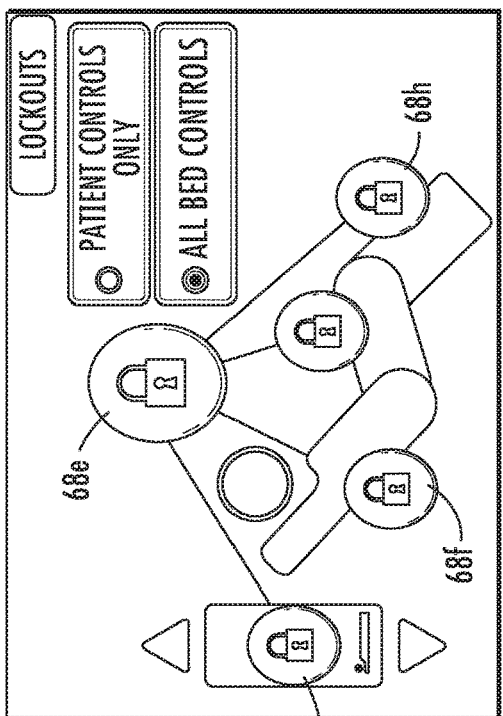
*FIG. 31D*
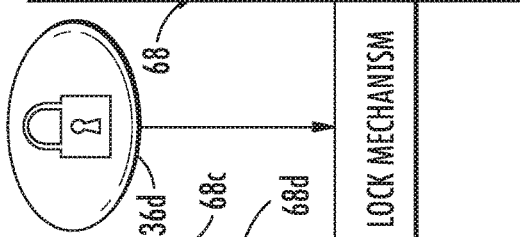
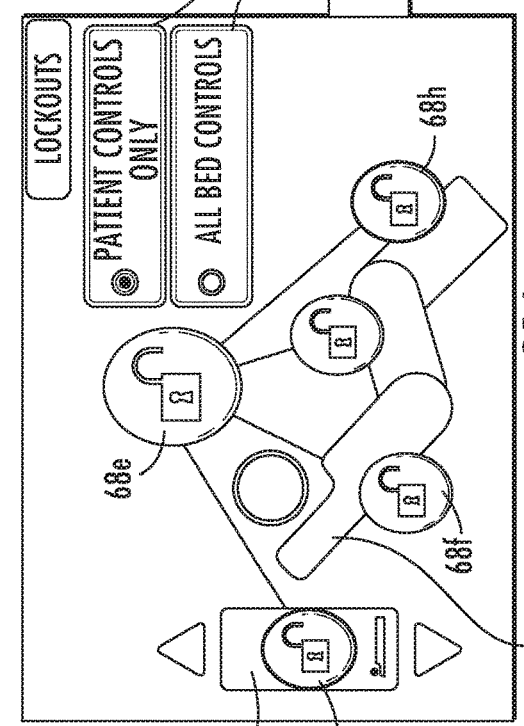
*FIG. 31A*
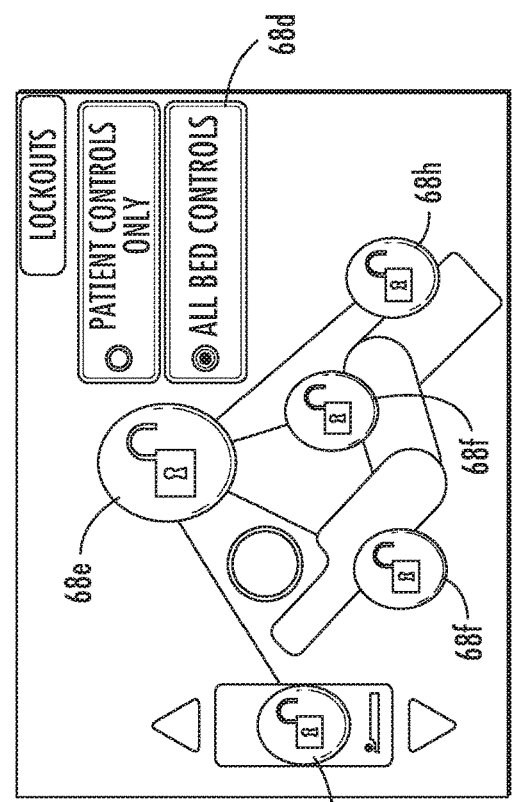
*FIG. 31C*

PATIENT SUPPORT WITH IMPROVED CONTROL

CROSS REFERENCE TO RELATED APPLICATIONS

This application is a continuation of co-pending application Ser. No. 14/719,671 (P-199B), filed on May 22, 2015, entitled PATIENT SUPPORT WITH IMPROVED CONTROL by Applicants Derick Elliot et al., which is a continuation-in-part of application Ser. No. 13/035,544 (P-102E), now U.S. Pat. No. 9,126,571 issued Sep. 8, 2015, entitled HOSPITAL BED by Applicants Guy Lemire et al., which is a continuation of application Ser. No. 11/642,047 (P-102C), now U.S. Pat. No. 7,962,981, issued Jun. 21, 2011, entitled HOSPITAL BED by Applicants Guy Lemire et al., which claims benefit of provisional application 60/874,287 (P-102), filed Dec. 11, 2006, entitled HOSPITAL BED and provisional application 60/751,770 (P-101) filed Dec. 19, 2005, entitled HOSPITAL BED; application Ser. No. 14/719,671 (P-199B) filed May 22, 2015 entitled PATIENT SUPPORT WITH IMPROVED CONTROL, is a continuation of application Serial application Ser. No. 11/941,338 (P-199), which is a continuation-in-part of application Ser. No. 11/642,047 (P-102C), now U.S. Pat. No. 7,962,981, issued Jun. 21, 2011, entitled HOSPITAL BED, which claims benefit of provisional application 60/874,287 (P-102), filed Dec. 11, 2006, entitled HOSPITAL BED and provisional application 60/751,770 (P-101) filed Dec. 19, 2005, entitled HOSPITAL BED; application Ser. No. 11/941,338 (P-199) filed Nov. 16, 2007 entitled PATIENT SUPPORT WITH IMPROVED CONTROL is a continuation-in-part of application Ser. No. 11/612,361 (P-102D), now U.S. Pat. No. 7,861,334 issued Jan. 4, 2011 entitled HOSPITAL BED, which claims benefit of provisional application 60/874,287 (P-102), filed Dec. 11, 2006, entitled HOSPITAL BED and provisional application 60/751,770 (P-101) filed Dec. 19, 2005, entitled HOSPITAL BED; application Ser. No. 11/941,338 (P-199) is a continuation-in-part of application Ser. No. 11/612,428 (P-102A), now U.S. Pat. No. 7,690,059 issued Apr. 6, 2010 entitled HOSPITAL BED, which claims benefit of provisional application 60/874,287 (P-102), filed Dec. 11, 2006, entitled HOSPITAL BED and provisional application 60/751,770 (P-101) filed Dec. 19, 2005, entitled HOSPITAL BED; application Ser. No. 11/941,338 (P-199) is a continuation-in-part of application Ser. No. 11/612,405 (P-102B), now U.S. Pat. No. 7,805,784, issued Oct. 5, 2010 entitled HOSPITAL BED, which claims benefit of provisional application 60/874,287 (P-102), filed Dec. 11, 2006, entitled HOSPITAL BED and provisional application 60/751,770 (P-101) filed Dec. 19, 2005, entitled HOSPITAL BED.

TECHNICAL FIELD AND BACKGROUND OF THE INVENTION

The present invention relates in general to the field of patient supports, such as hospital beds. In particular, the invention relates to an improved control system that provides enhanced control of the patient support and accessories mounted at the patient support and, further, provides enhanced information related to the patient support and the patient and, further, allows for improved monitoring of the patient.

SUMMARY OF THE INVENTION

Accordingly, the present invention provides a patient support that incorporates a controller that provides enhanced control over and/or information relative to one or more of the patient support functions and, further, over information relating to the patient.

In one form of the invention, a patient support includes a patient support surface, a user interface, and a controller. The controller has stored therein a plurality of prompts. The user interface is in communication with the controller and is configured to select one or more of the prompts from the prompts stored in the controller. Further, the user may generate or create a prompt to be stored in the controller. For example, the user may input or upload into the controller a prompt stored on a network or from a storage device, such as a memory stick or data card.

When a prompt is selected, the controller generates an output prompt associated with the selected prompt at the patient support in response to a passage of time or in response to an input to provide a prompt to the user. The prompts may include, for example, protocol reminders, such as to turn or rotate the patient, to weigh the patient, to check the patient's blood sugar, blood pressure, heart rate, and other vital signs, to apply DVT prophylaxis, percussion, or vibration, to check wounds, to administer oral care to the patient, to wash the patient, and to check the patient's position on the bed, to name a few. Alternately, the prompts may relate to conditions that the user selects to be informed about—for example, when the bed is wet, the patient is inactive for a selected period of time.

In one aspect, the patient support further includes a display, and the output prompt comprises a display image or text at the display. Alternately, the output may comprise an audible output.

In another aspect, the user interface includes a first user interface associated with one of the prompts and a second user interface associated with another of the prompts.

In one aspect, the display comprises a touch screen. For example, the user interface may comprise at least one touch sensitive area of the touch screen wherein the touch screen forms the user interface.

In a further aspect, the touch screen includes a plurality of sensitive areas, with the sensitive areas forming a menu for the protocols.

According to another aspect, the patient support further includes a frame that supports the patient support surface and a footboard, with the display mounted at the footboard. Further, the controller may be mounted at the footboard. In addition, the controller and the display may be a combined unit.

In yet another aspect, the patient support further comprises a second user interface, with the second user interface for selecting an alarm setting that is stored in the computer for the selected prompt. For example, the second user interface may select a time or passage of time for the selected prompt for the alarm to be triggered. When the alarm setting is selected, the controller actuates the alarm in response to the time or passage of time input for the selected prompt.

In a further aspect, the touch screen displays a first screen image and a second screen image. The first screen image displays the first user interface, and the second screen displays the second user interface. The second screen image includes a plurality of user interfaces in the form of touch sensitive areas that provide a menu of options relative to the alarm setting.

According to yet other aspects, the controller may be configured for storing and collecting data, for example, related to a protocol. Additionally, the controller may have stored therein data related to a protocol, for example, in the form of a look-up table. Further, the controller is adapted to compare collected protocol data to the stored data to verify conformance. For example, the controller may compare patient support surface movement collected by the controller to the stored data for patient support surface movement.

Other features may include the controller generating a report based on the collected data and/or the controller communicating with a remote user to allow remote monitoring of the protocols. For example, the controller may create a report on the use of a particular protocol. The controller may be in communication with a network that allows: a remote user to review the reports; generate a separate report based on the report or reports generated by the controller or based on parameters selected by the network user; view the selected protocols for a given patient support; select other protocols from the available protocols stored in the controller; and/or input a protocol to the controller, as noted above, based on input from the network user.

In another form of the invention, a patient support includes a patient support surface, a plurality of sensors associated with the patient support for sensing at least two conditions at the patient support, a patient support-based controller in communication with the sensors, which is mounted at the patient support, and a display mounted at the patient support. The controller is in communication with the display, and a user interface is also provided, which is operable to select one of the conditions. When a condition is selected, the controller monitors the selected condition and generates a display at the display when the selected condition occurs.

In one aspect, the display comprises a touch screen. Further, the controller generates and displays a screen image at the touch screen. The screen image optionally includes a region forming the user interface.

In a further aspect, the screen image includes a plurality of regions forming a menu for selecting the conditions.

In another aspect, the patient support further comprises a second user interface, which is used for selecting an alarm setting, which is stored in the computer, for the selected condition. When the alarm setting is selected, the controller actuates the alarm when the selected condition occurs.

In another aspect, the controller generates a second screen image at the touch screen, which has a plurality of regions. The regions of the second screen image provide a menu of options relative to the alarm setting.

According to another aspect, at least some of the sensors are load cells, which are in communication with the controller. The controller may use the signals from the load cells to determine whether the bed is occupied or not, including when a patient is exiting a bed, or to determine the weight of the patient. When the controller detects that a patient is exiting a bed, the controller may actuate an alarm. The alarms setting may be selected based on a pressure trigger and an elapsed time. Further, the alarm may be trigger by movement or lack of movement. For example, the load cells may be used to calculate the center of gravity of the patient and the controller then may monitor the center of gravity and when it is detected that the center of gravity has not moved over a pre-selected period of time, the controller may trigger the alarm.

Alternately, pressure sensors may be provided at the patient support surface, for example, in a mat that is placed over the patient support surface, such as the mattress, or may be located in the patient support surface. The pressure sensors may also be used to generate a pressure map of the pressure readings taken by the sensors at the patient surface. Knowing the pressure points on the patient support surface may enable the healthcare worker to know whether a particular part of the patient's body is vulnerable to forming sores and needs to be moved. When a high pressure point is detected, the patient's position may be adjusted by the care giver. Further, an alarm may be triggered when a high pressure point is detected. For example, the controller may monitor the pressure points and when it is detected that the pressure points have exceeded a pre-selected value and, optionally, for a pre-selected period of time, the controller may trigger the alarm.

Further, load cells or pressure sensors may be used to monitor the vital signs of a patient on the support. For example, the sensors may include temperature sensors for monitoring the temperature of the patient. Alternately, the patient support may incorporate a separate vital signs monitoring device, such as is available from Phillips, which is communication with the bed network and controller. The controller then may display the vital signs data collected either by the controller from the bed-based sensors or from the separate vital signs monitoring device. Vital signs that can be monitored include temperature (as noted), ECG, SpO2, blood pressure, or the like.

In another aspect, the patient support further includes a side rail. The sensors may include at least one side rail sensor for detecting whether the side rail is lowered or not. The controller uses the signals from the side rail sensor to determine whether the side rail is lowered or not.

Further, the patient support may include a brake, wherein the sensors include a brake sensor for detecting whether a brake is on or off, and with the controller using a signal from the brake sensor to determine whether the brake is on or off.

In yet another form of the invention, a patient support includes a patient support surface, a device associated with the patient support for sensing or controlling a parameter at the patient support, a patient support-based controller which is mounted in the patient support, and a display mounted at the patient support. The controller is in communication with the device and the display. A user interface is provided that is in communication with the controller, which is operable to select the parameter for display at the display. When selected, the controller monitors the device and generates a display at the display associated with the parameter.

In one aspect, the display comprises a touch screen. Further, the controller generates a screen image at the touch screen, which may include a region that forms the user interface.

In a further aspect, the screen image may include a text window for displaying the parameter.

In another aspect, the device comprises a plurality of pressure sensors, for example load cells, that are in communication with the controller and which can be used to determine the weight of the patient, the vital signs of the patient, whether the patient has high pressure points, and/or if the patient has exited the bed.

In another aspect, the device comprises an angle sensor for detecting the angle of the patient support surface.

In yet another aspect, the patient support surface includes a mattress, such as a mattress that includes a plurality of, bladders, and the device comprises a controller, for example, a mattress-based controller, which may control one or more functions of the mattress, for example, the mattress firmness or treatment provided by the mattress, including for example, percussion, vibration or patient turning.

According to another form of the invention, a patient support includes a patient support surface, a frame, which supports the patient support surface, at least one actuator for adjusting the patient support surface or the frame, and a patient support-based controller. The controller is in communication with the actuator and operable to send drive signals to the actuator and, further, is mounted at the patient support. A display is also mounted at the patient support, which is in communication with the controller. A user interface is provided that is in communication with the controller and which is operable to send an input signal to the controller. The controller communicates a drive signal to the actuator in response to the input and indicates a parameter at the display of the patient support surface or the frame associated with driving the actuator. For example, when driving an elevation mechanism actuator, the parameter may comprise the height of the patient support surface. When driving an actuator that changes the configuration of the patient support surface, the parameter may comprise the angle of the patient support surface or the angle of one section of the support surface.

In one aspect, the actuator adjusts the firmness of the patient support surface. In this case, the parameter may be the amount of firmness.

In another aspect, the actuator generates vibration at the patient support surface. For example, the vibration can be used as therapy for the patient.

In yet another aspect, the actuator adjusts the angle the patient support surface. For example, the frame optionally includes a deck frame, with the deck frame having a plurality of deck sections that support the patient support surface, with the actuator adjusting the angle of at least one deck section to thereby adjust the angle of the patient support surface.

According to yet another aspect, the actuator may adjust the elevation of the frame.

In other aspects, the display comprises a touch screen. The user interface comprises at least one sensitive area of the touch screen wherein the touch screen forms the user interface.

The display may, for example, be mounted in a footboard of the patient support.

According to another form of the invention, a patient support includes a patient support surface, a controller, and a display mounted at the patient support. The controller is in communication with the display, which includes at least one user interface operable to input an input signal into the controller.

In one aspect, the controller translates or converts the input signal into an output signal having a different format from the input signal. For example, the controller may generate an image at the display, which may display text or a numerical value at the display responsive to the output signal from the controller.

In another aspect, the output comprises an audible output, for example through a microphone at the patient support. For example, when different format comprises a different language, the output may in the form of a spoken translation or a translated text message at the display.

For example, the controller may display a plurality of selected phrases, with the user interface operable to select one of the phrases as input to the controller. Thereafter, the controller generates an output which is a translation of the phrase. In addition, the controller may have stored there in the phrase(s) in multiple languages and further allows the user to select the language. Additional features may include a collection of words and phrases so that the user may select words and/or phrase to construct a sentence, which is then translated by the controller into the language selected by the user. These constructed sentences may then be stored for later use. Examples of suitable phrases may relate to patient movement or to safety issues.

In a further aspect, the controller may be coupled to a voice recorder and player, for example an MP3 player. In this manner, a user may record a phrase or phrases at the patient support using the controller for later use. In addition, the controller may select a phrase to be played in response to a condition on the patient support. For example, the controller may be program to play the phrase "stay in the bed" or the like in response to the load cells generating signals indicative of an undesired impending bed exit by the patient.

Further, these phrases may be stored in a foreign language. For example, a user may select the output language, including for displayed text for the patient or phrases that are played at the bed.

In another aspect, the different format comprises a different scale. For example, the controller may include stored therein a formula or a look-up table for converting the input into the output.

In yet another aspect, the user interface is operable to input bed usage information to the controller. For example, the user interface may be configured to: input a room assignment for the bed; patient related data; and/or nurse related information. The user interface may comprise a keyboard, including a keyboard on a touch screen so that the user may key in the information. Further, this information may be displayed, for example, at a display at the bed (for example at the footboard display) or at a display remote from the bed, for example at a nurses' station.

Alternately, or in addition, the patient support may include a voice recognition system, which is in communication with the controller and may be used to input data or commands into the controller. For example, a user may speak into the voice recognition software microphone and state, for example, bed usage information, which is then converted into input data for the controller by the voice recognition system software. Further, functions on the bed may be triggered by input generated by the voice recognition system. For example, a user may state a command relative to a function on the bed, for example to raise the head end of the bed, which command is then converted by the voice recognition software into an input command signal, which when received by the controller will generate an actuation signal associated with the function of the command, for example a drive signal to the head end actuator. The user may be a health care provider or the patient.

According to yet another form of the invention, a patient support includes a patient support surface, a patient support-based controller mounted in the patient support, and a display mounted at the patient support. The controller has stored therein a plurality of options and parameters associated with the option. The controller is in communication with the display for displaying the options at the display. A user interface is provided that is in communication with the controller and operable to select one of the options and, further, operable to select a parameter from the stored parameters associated with a selected option for display at the display.

In one aspect, the options include an accessory control. For example, the patient accessory control may comprise a light or a television control. For the light, the parameter may comprise brightness. For the television control, the parameter may comprise a pre-selected configuration.

In another aspect, the options include a data listing. For example, the data listing may include a data listing of bed or patient parameters, including a bed height or angle history or a patient's weight history. The parameters may also include the time and date of when the data was collected.

Accordingly, the present invention provides a patient support with improved control and information relating to the patient support and/or the patient.

These and other objects, advantages, purposes, and features of the invention will become more apparent from the study of the following description taken in conjunction with the drawings.

BRIEF DESCRIPTION OF THE DRAWINGS

FIG. 15A is a right perspective view of an indicator system for the braking system of FIG. 15, shown in steer;

FIG. 15B is a right perspective view of an indicator system for the braking system, shown in neutral;

FIG. 15C is a right perspective view of an indicator system for the braking system, shown in brake;

FIG. 15G is a right perspective view of the braking system in override mode, wherein the central levering mechanism is in a steer position and wherein an override pedal is in a brake position;

FIG. 15H is a right perspective view of the braking system in override mode, wherein the central levering mechanism is in a steer position and wherein an override pedal is in a neutral position;

FIG. 15I is a right perspective view of the braking system in override mode, wherein the central levering mechanism is in a steer position and wherein an override pedal is in a steer position;

FIG. 15J is a right perspective view of the braking system in override mode, wherein the central levering mechanism is in a neutral position and wherein an override pedal is in a brake position;

FIG. 15K is a right perspective view of the braking system in override mode, wherein the central levering mechanism is in a neutral position and wherein an override pedal is in a neutral position;

FIG. 15L is a right perspective view of the braking system in override mode, wherein the central levering mechanism is in a neutral position and wherein an override pedal is in a steer position;

FIG. 15M is a right perspective view of the braking system in override mode, wherein the central levering mechanism is in a brake position and wherein an override pedal is in a brake position;

FIG. 15N is a right perspective view of the braking system in override mode, wherein the central levering mechanism is in a brake position and wherein an override pedal is in a neutral position;

FIG. 15O is a right perspective view of the braking system in override mode, wherein the central levering mechanism is in a brake position and wherein an override pedal is in a steer position;

FIG. 31A illustrates a screen image provided by the controller at the display;

FIG. 31B illustrates a screen image provided by the controller at the display;

FIG. 31C illustrates a screen image provided by the controller at the display;

FIG. 31D illustrates a screen image provided by the controller at the display;

DETAILED DESCRIPTION OF THE PREFERRED EMBODIMENTS

Figure 1:
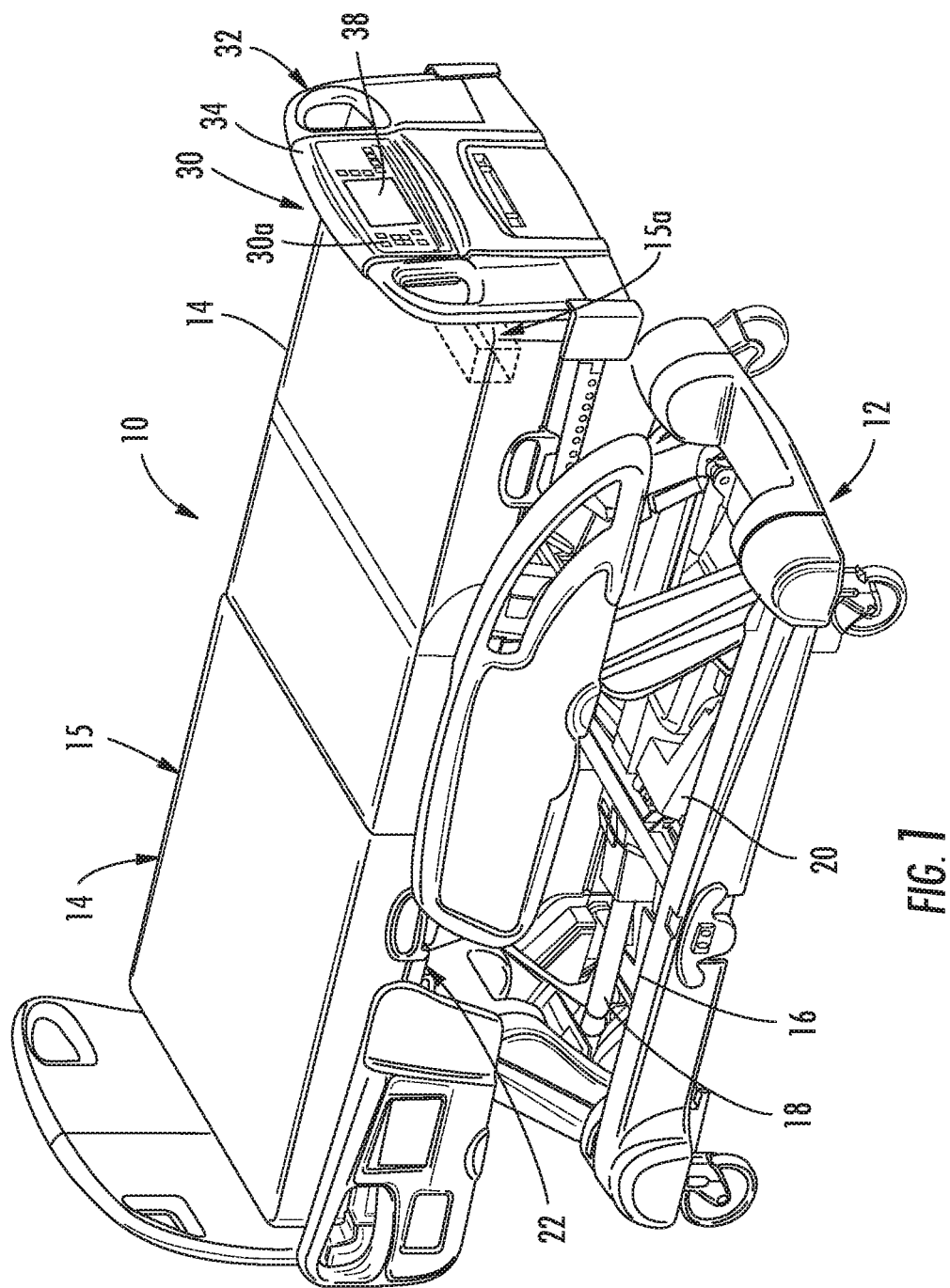
FIG. 1 is a perspective view of the patient support of the present invention.

Referring to FIG. 1, the numeral 10 generally designates a patient support of the present invention. As will be more fully described below, patient support 10 incorporates a control system with one or more controllers that enhance the ability of the user, such as a medical care provider, to control various functions on patient support 10 and, further, to input information, data, or settings into the control system to enhance the care of the patient. For the purpose of this description, patient support 10 will be described hereinafter as a bed 10; however it should be noted that the concepts of the present invention may be incorporated into other patient supports, including stretchers, cots, or the like.

Figure 3:
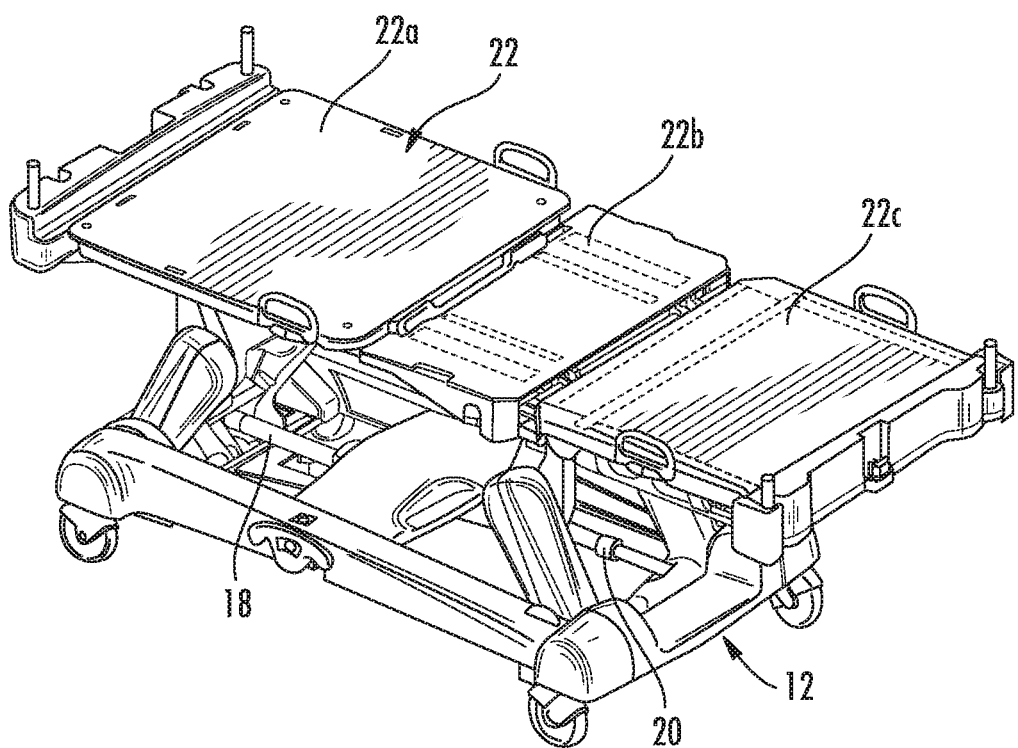
FIG. 3 is a perspective view of the patient support of FIG. 1 with the headboard, footboard and side rails removed for clarity.
Figure 6:
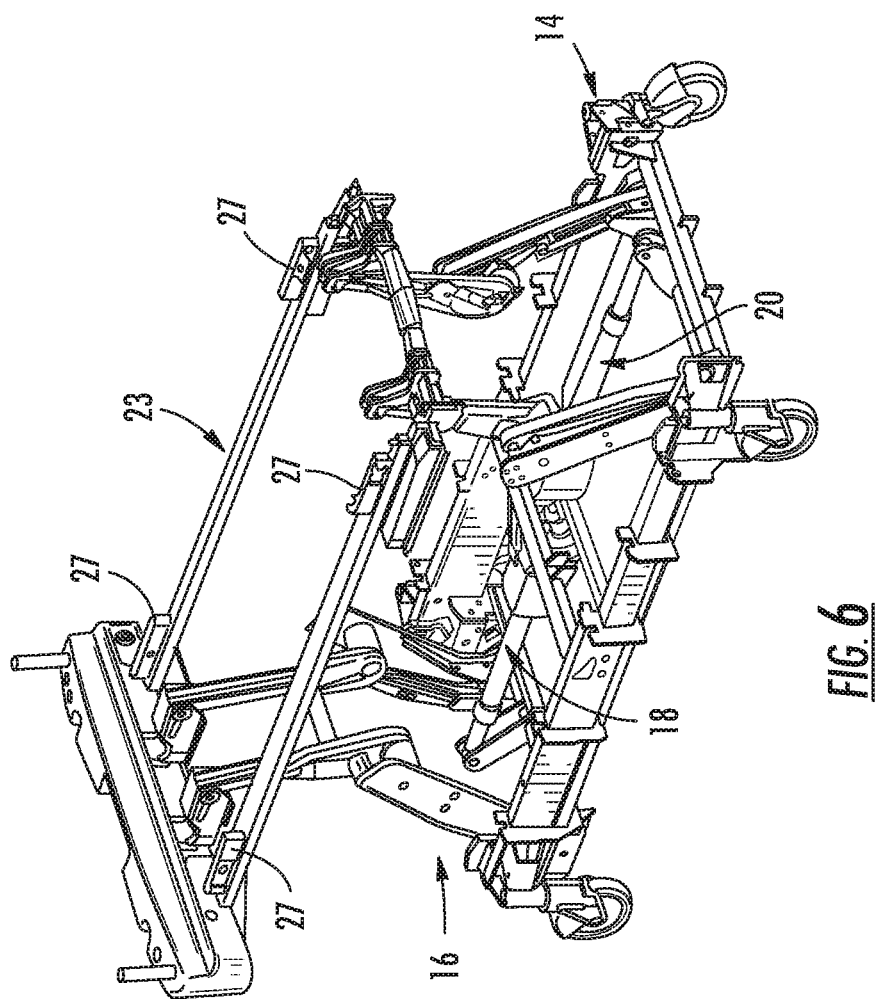
FIG. 6 is a perspective view of the base and load frame of patient support of FIG. 1 with the deck and headboard, footboard, and side rails removed for clarity.
Figure 7:
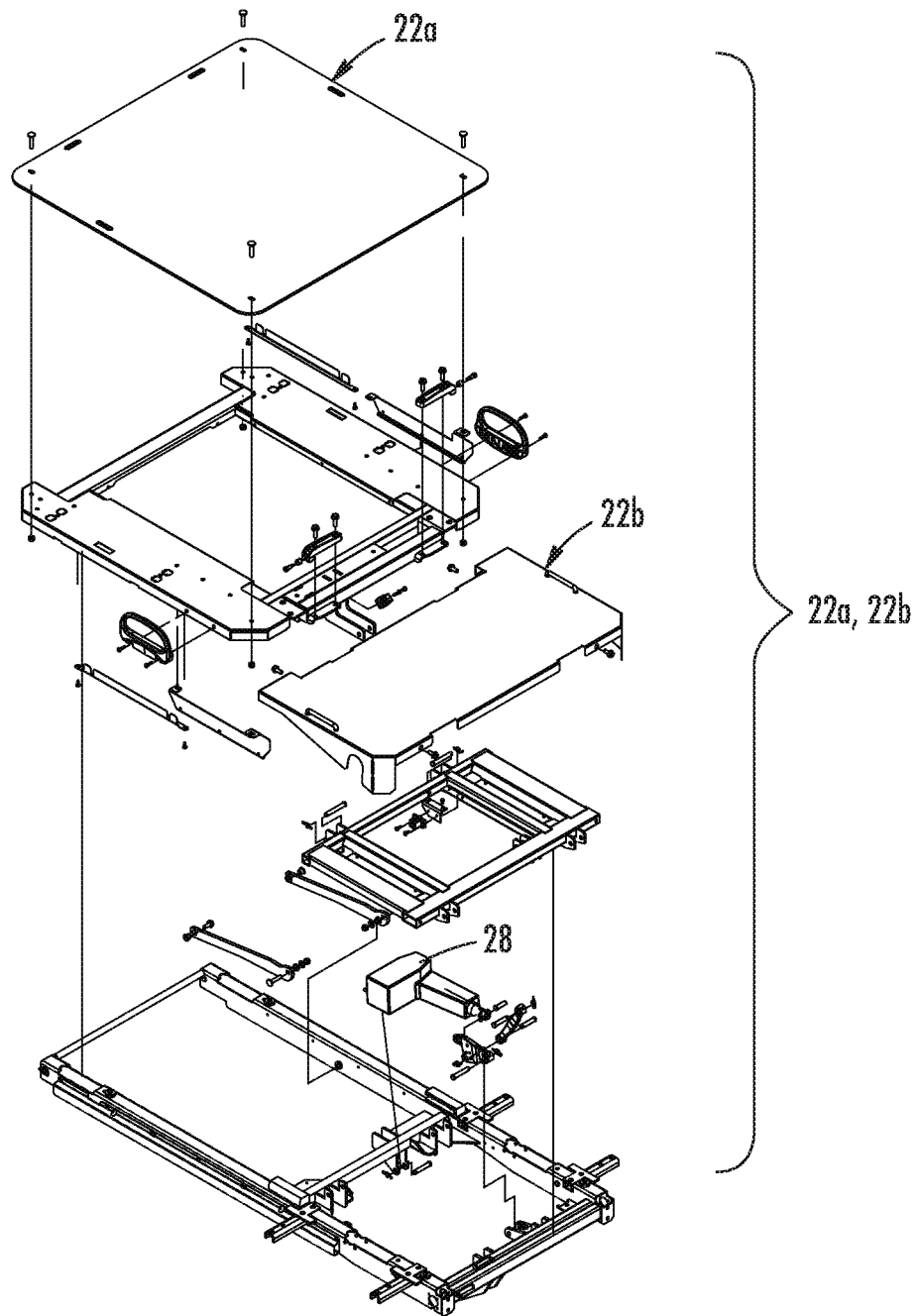
FIG. 7 is an exploded perspective view of the head and seat portions of the deck support.
Figure 8:
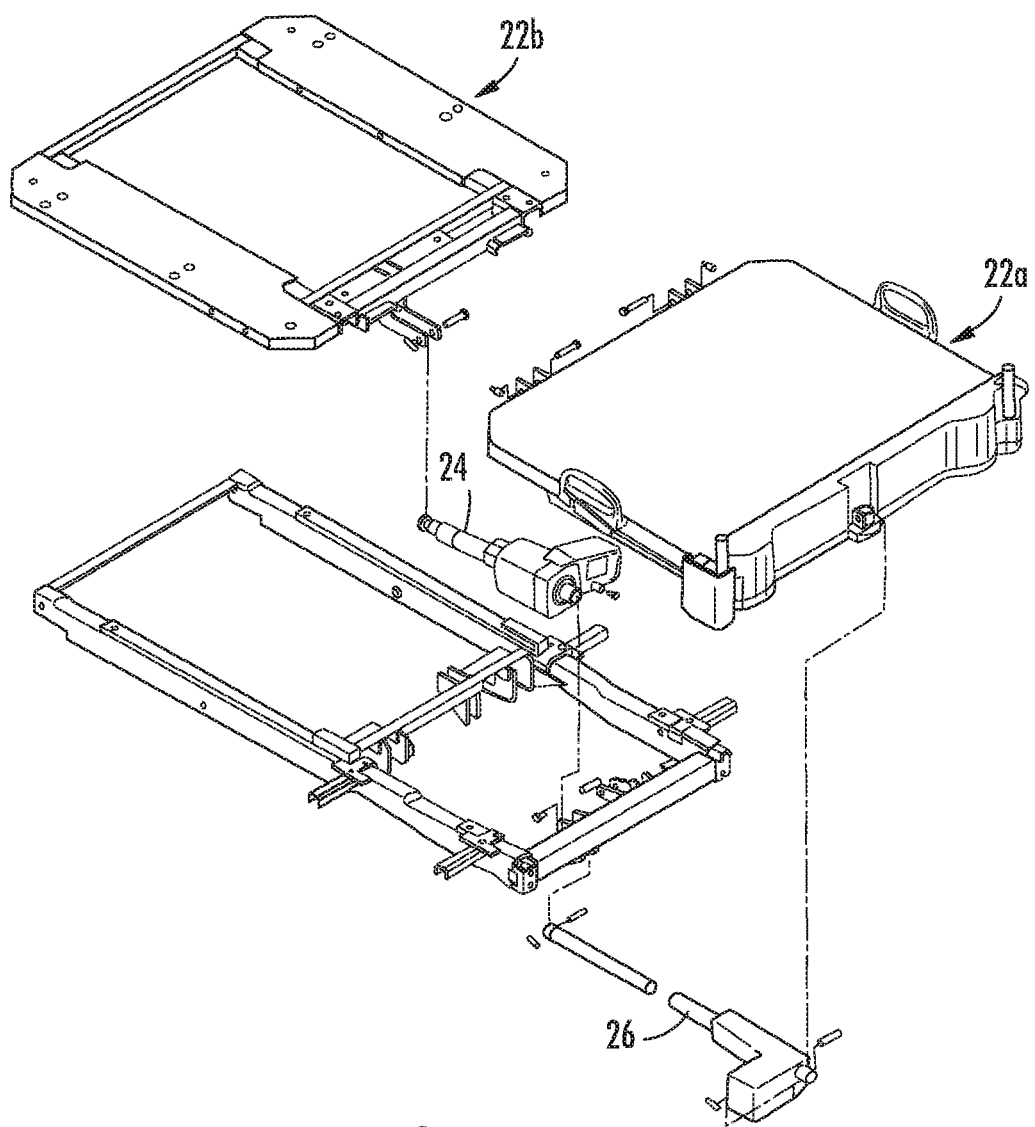
FIG. 8 is another perspective view of head and foot portions of the deck support.
Figure 9:
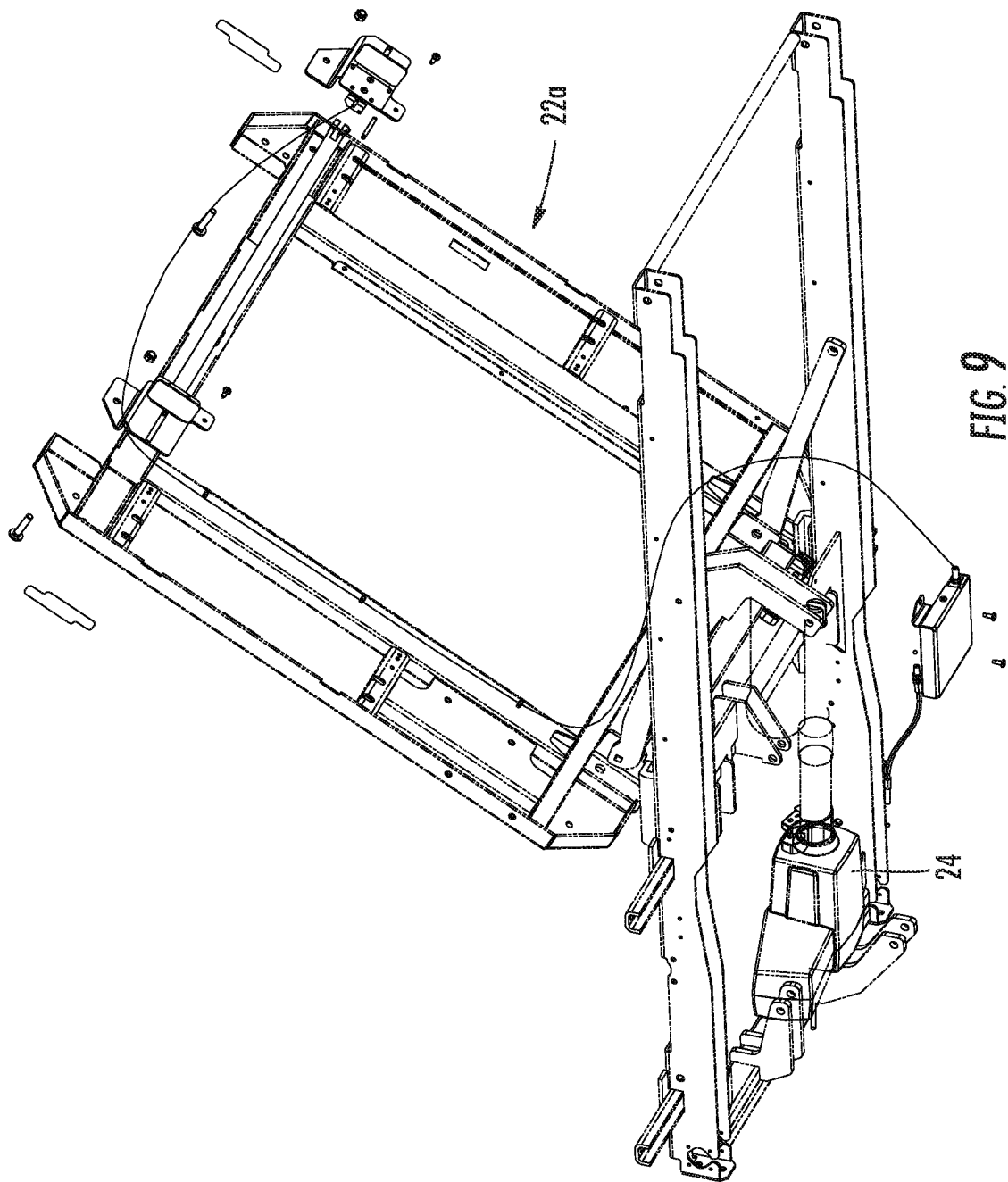
FIG. 9 is the bottom view of the actuation of the head portion of the deck support.
Figure 10:
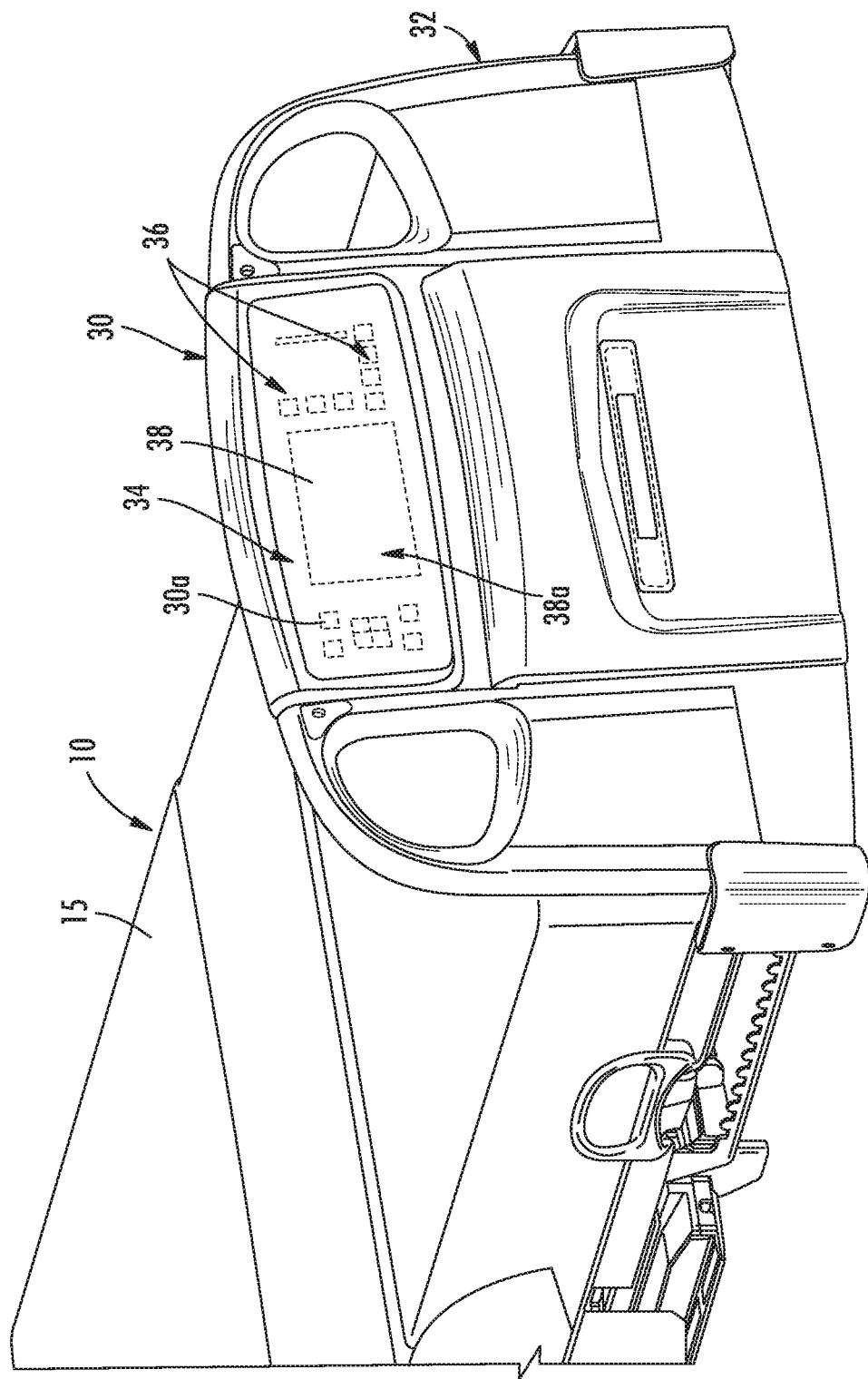
FIG. 10 is a large perspective view of the foot board of the patient support apparatus in FIG. 1.
Figure 11:
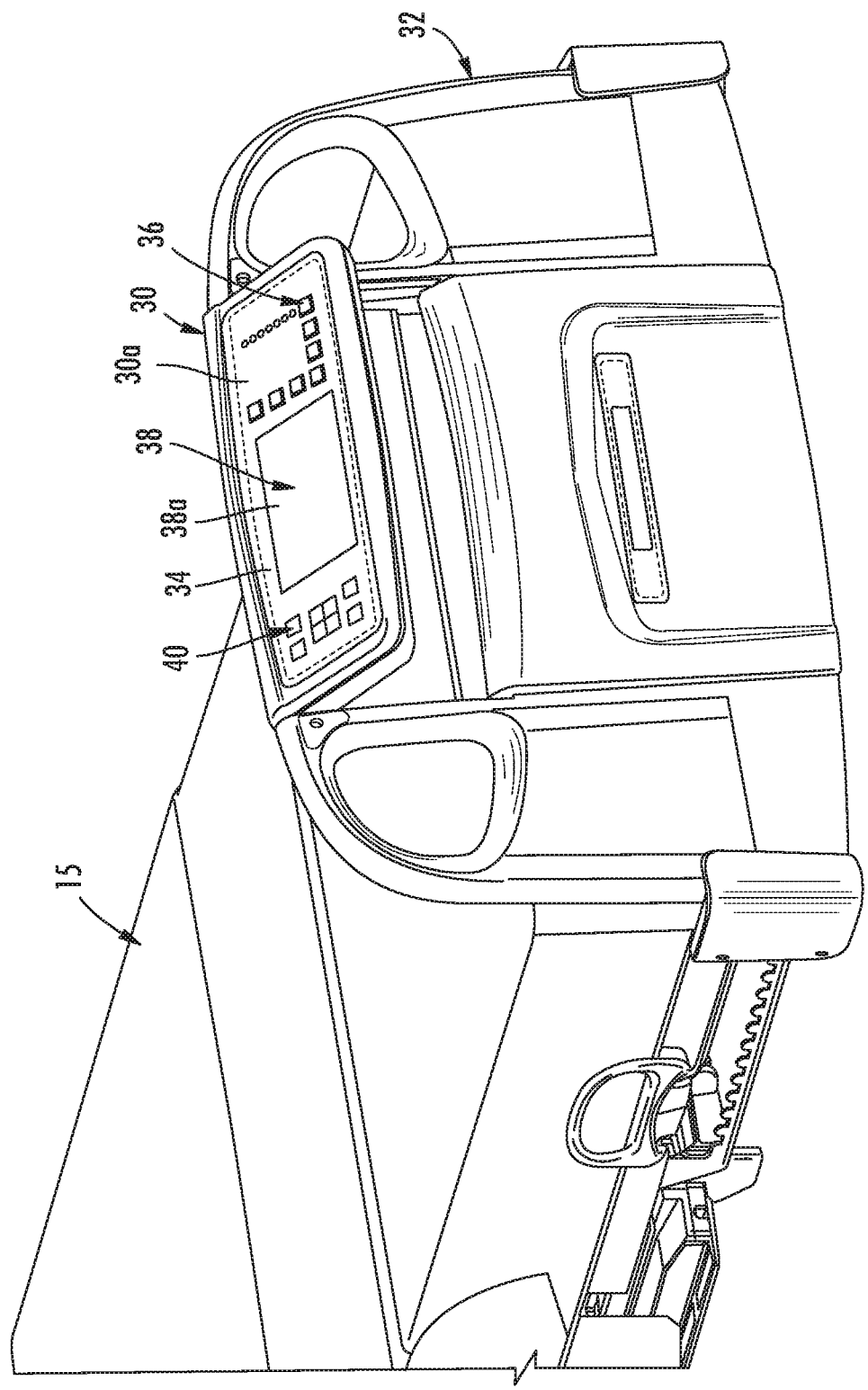
FIG. 11 is a similar view to FIG. 10 illustrating the control panel in a tilted position.
Figure 12:
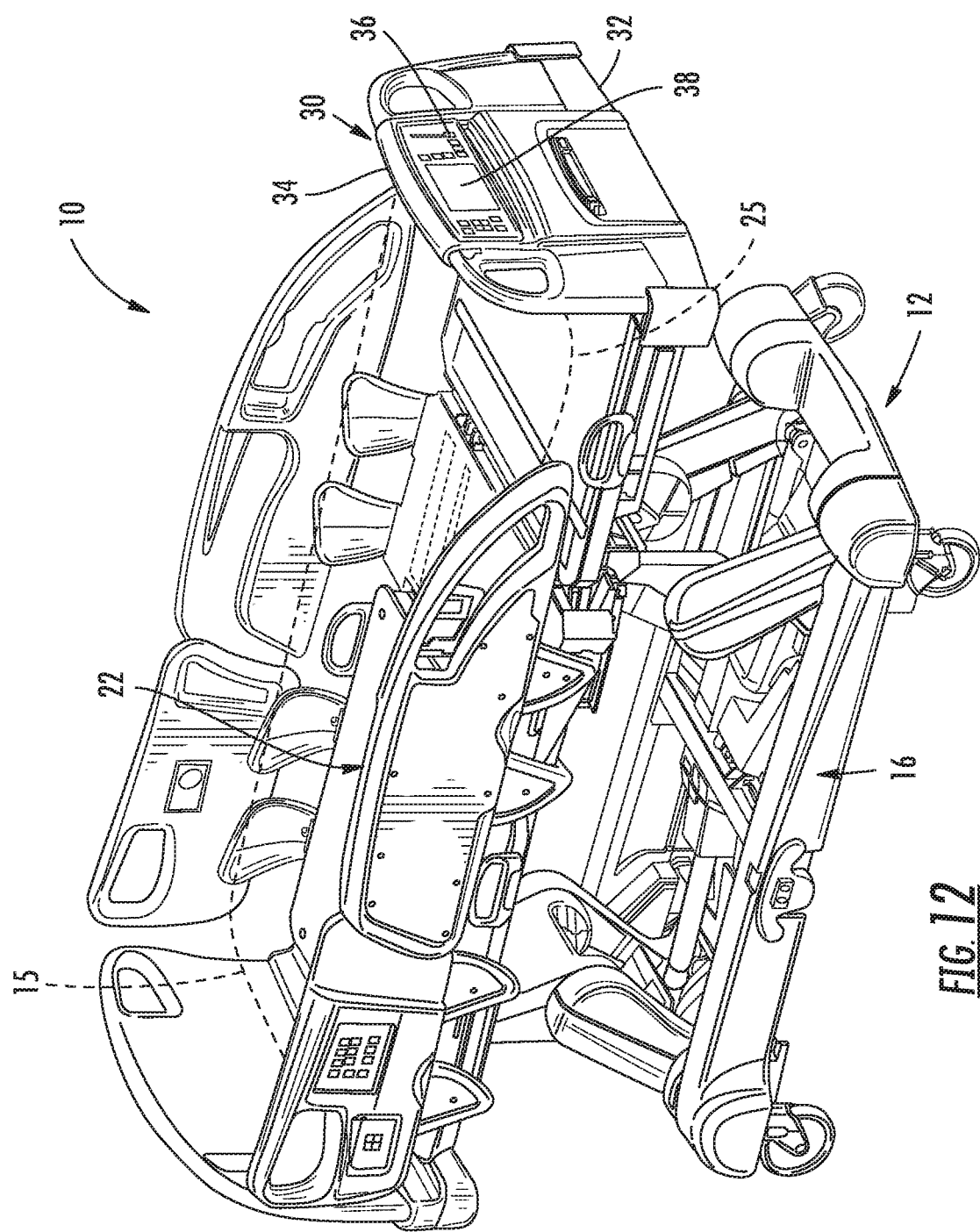
FIG. 12 is another perspective view of the patient support of the present invention with the mattress removed for clarity illustrating the side rails in a raised position.

Bed 10 includes a base 12 and a patient support surface 14, which is supported by base 12. Patient support surface 14 is mounted to base 12 for vertical movement relative to base 12 and is raised and lowered relative to base 12 by an elevation mechanism 16 (FIG. 6), which incorporates a pair of actuators 18 and 20 (FIGS. 3 and 6), more fully described in the above-referenced applications, namely, U.S. patent application Ser. Nos. 11/642,047; 11/612,361; 11/612,405; and Ser. No. 11/612,428, all entitled HOSPITAL BED and commonly assigned to Stryker Corporation of Kalamazoo, Mich. In addition to actuators 18 and 20, bed 10 includes actuators 24, 26, and 28 (FIGS. 7-9) to adjust the orientation of the patient support surface 14 and an actuator 29 (FIG. 15) to actuate brakes at the bed casters. For further details of the operation of actuator 29 reference is made below and for the other various actuators reference is made to the above incorporated patent applications.

Figure 5:
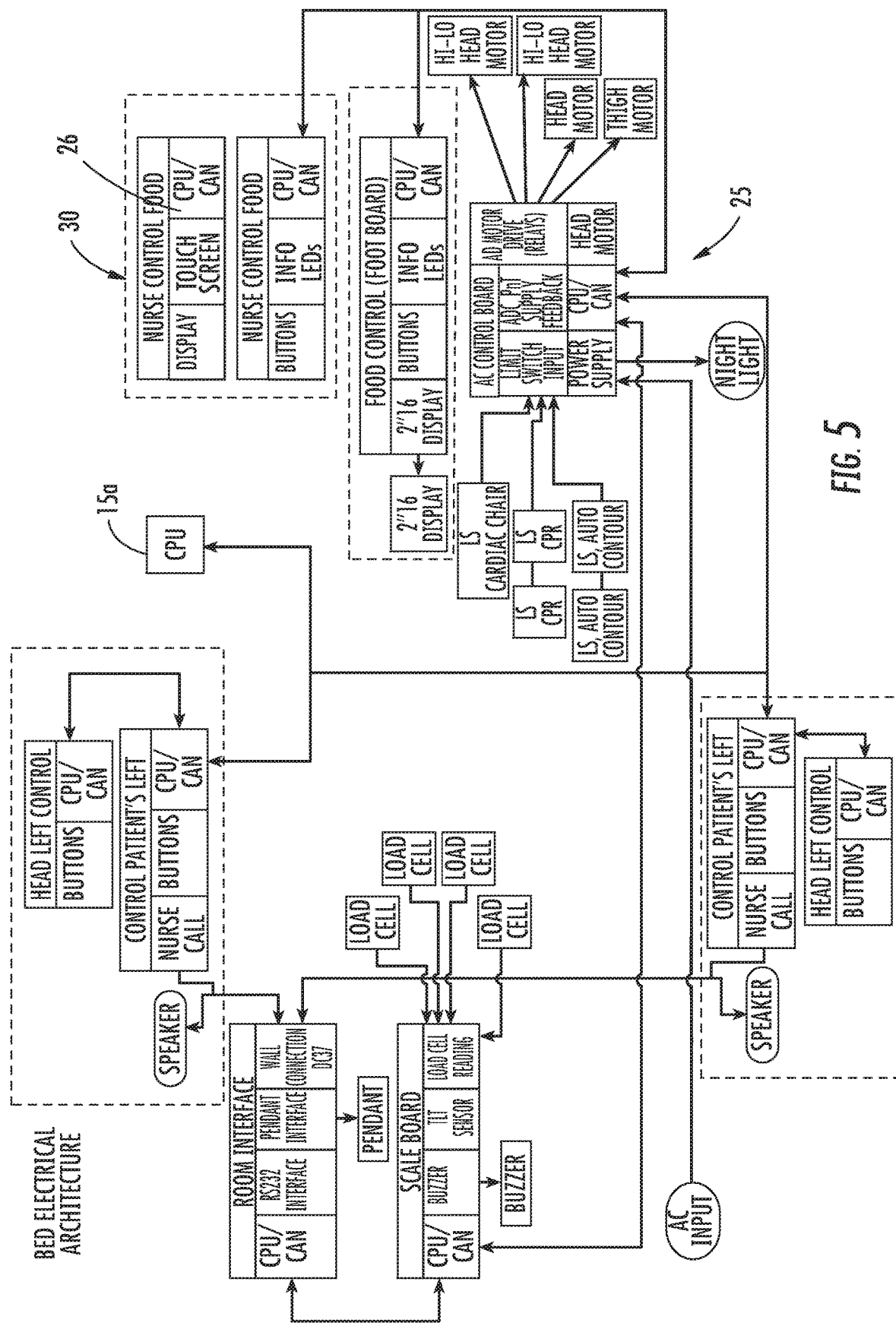
FIG. 5 is a schematic view of the patient support electrical architecture.

Referring again to FIG. 1, patient support surface 14 includes a mattress 15 and a deck frame assembly 22 (FIG. 3) with a head deck section 22a, a seat deck section 22b, and a foot deck section 22c, each of which can be adjusted to a different orientation by actuators 24, 26, and 28 to adjust the angular position of the mattress, also described in the pending applications. Mattress 15 may comprise a conventional mattress, include a foam mattress, or a mattress that incorporates one or more bladders that can be inflated by an actuator, such as a pump, to turn the patient or can be inflated and deflated to adjust the firmness of the mattress or to induce vibration for percussion treatment or the like. Further the mattress 15 may incorporate a mattress-based controller 15a (FIG. 5) in the mattress, for example a PCB board with a microprocessor and associated circuitry, for powering the various devices in the mattress, which actuates the pump and valves to inflate or deflate the bladders to control various parameters at the surface. For example, mattress-based controller 15a may be used to adjust the stiffness of the mattress and/or provide treatment at the mattress, for example, by using the inflation or deflation of the bladders to provide percussion, vibration, or turning of the patient. As described in the referenced patent applications, mattress-based controller 15a may be coupled to a pendent type display, which provides one or more user actuatable devices, such as buttons, touch screen areas, including a menu, or the like to allow a user to input command signals to the mattress-based controller to control the pump and valves and hence the flow of fluid in and out of the bladders. Further, the display may display an icon or image associated with the parameter being controlled by the mattress-based controller. Alternately, the mattress-based controller may be coupled directly to the bed-based controller described more fully below in lieu of the pendent display so that the functions or status of the mattress, as well as of the bed, may be displayed and controlled from one location at the bed. With this arrangement, the mattress may include a connector, which is electrically coupled to for example to the PCB, for coupling the bed-based controller to the mattress-based controller, which allows power and signals to be transferred to the mattress-based controller through the connector. For example, the connector may be located at the side of the mattress as shown in one or more of the referenced applications or at the foot end of the mattress.

Alternately, the bed-based controller may be incorporated into the mattress. For example, the controller may be incorporated into the pump enclosure provided in the mattress (similar to the mattress-based controller) or into another enclosure incorporated into the mattress. As described in the referenced applications, the enclosure may be located at the foot end of the mattress, for example, in a recess provided in the mattress. In this application, the bed and mattress could be provided with one or more connectors for electrically coupling the various devices on the bed to the controller through the connector or connectors. A suitable connector may include a combined power and signal connector, which includes cabling for power and cabling for signals, or may include separate power connectors and signal connectors. For example, the bed connector may be provided in the footboard or headboard, with the corresponding connector in the mattress provided at the foot end or head end of the mattress. In this manner, the mattress may be plugged in the bed (or vice versa)

Further, the footboard may be configured to accommodate the pump enclosure and/or controller enclosure, which as noted may be located at the foot end of the mattress. For example, the footboard may include a recess to accommodate the pump enclosure and/or controller enclosure. Alternately, the footboard may be configured to receive the pump enclosure and/or controller enclosure, with connections provided at the mattress for coupling the pump and valves in the pump enclosure to the bladders in the mattress.

For examples of suitable mattresses, bladders, and mattress-based controls reference is made herein to U.S. Provisional application entitled, A PATIENT LYING SURFACE WITH TURN-ASSIST, Ser. No. 60/866,206, filed Nov. 16, 2006; U.S. patent application Ser. No. 11/260,452, filed Oct. 27, 2005 entitled PATIENT SUPPORT APPARATUS; U.S. patent application Ser. No. 11/381,631, filed May 4, 2006 entitled VIBRATING PATIENT SUPPORT APPARATUS WITH A RESONANT REFERENCING PERCUSSION DEVICE; and U.S. patent application Ser. No. 11/381,669, filed May 4, 2006, entitled VIBRATING PATIENT SUPPORT APPARATUS WITH A SPRING LOADED PERCUSSION DEVICE, and U.S. Pat. Nos. 5,179,742; 5,542,136; 5,325,551; 6,699,266, all commonly assigned to Stryker Corporation of Kalamazoo, Mich., which are incorporated by reference herein in their entireties.

Figure 4:
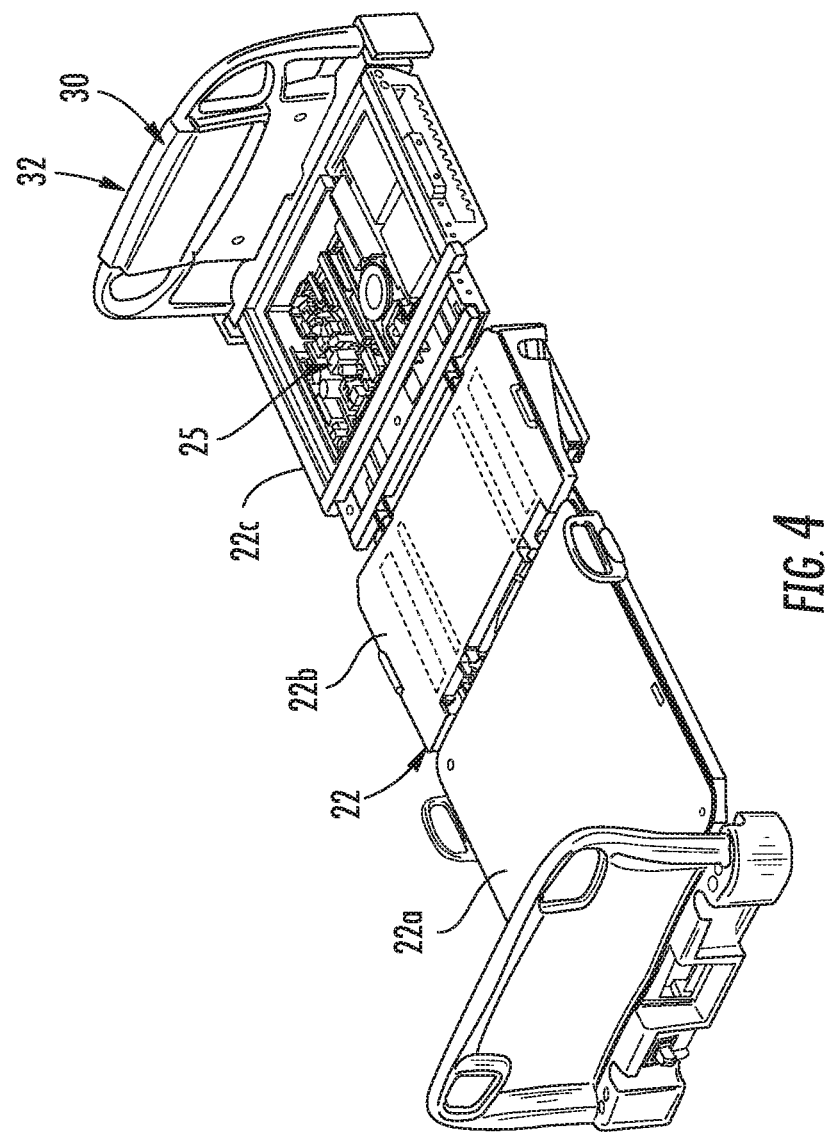
FIG. 4 is a perspective view of the deck assembly of the patient support FIG. 3 with the deck cover removed to illustrate the controller.

As noted above, bed 10 incorporates a control system with at least one controller 25 (FIGS. 4 and 5), which provides control of the various actuators on bed 10 and, further, senses the status of various bed parameters or conditions at the bed using sensors (e.g. load cells, tilt sensors, etc.) also described in the referenced applications. Additionally, as noted above, controller 25 may communicate with other devices at the bed, for example, a mattress-based controller (e.g. controller 15a) to provide and/or receive input to and/or from the mattress-based controller to control the functions of the mattress and/or to display information relative to the mattress, as will be more fully described below.

The sensors may include load sensors, side rail sensors, brake sensors, temperature sensors, moisture sensors, pressure sensors, or the like. Controller 25 may be in communication with other devices on or near the bed, for example, accessories, such as lights, a TV, speakers mounted in the bed, microphones, recording/playing devices, such as an MP3 player, or a universal serial bus (USB) device, or the like. Further, as will be more fully described below, bed 10 includes a control module 30 that allows a user, such as a healthcare worker, to input information, parameters and/or data into controller 25 and, further, to select various bed functions and protocols, which may be stored in controller 25 and then displayed at display 38 of module 30. Additionally, a USB device may be used to input information or upload data to the controller, including additional modules or the like. As would be understood, the USB device may also be used to download information from the controller.

Controller 25 is a bed-based controller and includes at least one central processor, software or programmable logic, and one or more storage or memory devices, as well as other accessories noted above. Further, controller 25 may be coupled to a USB port to allow data to be transferred to or from the controller through a memory device, as a memory stick or card, as noted above. In addition to providing the necessary algorithms to control and/or monitor functions and conditions at bed 10, including controlling the actuators and accessories at or near the bed, the software provides a graphic user interface (GUI) to organize to a multitude of functions at the bed as well as at control module 30. The GUI is configured to generate a variety of screen images at display 38, including symbols, such as icons, text, and/or numerical values, and/or text windows, in a number of different arrangements for each of the functions at the bed, including the bed status and configuration as well as to the patient status and, further, may be reconfigurable so that the screen images at display 38 may be customized and reconfigured as the user selects, all more fully described below.

Alternately, display 38 may be controlled and configured by a controller 26, which is a control module-based controller or a controller that is part of the display, which similarly includes a central processor and software and optionally one or more storage or memory devices depending on the number and complexity of functions to be controlled by the controller. Again, controller 26 may be coupled to a USB port to allow data to be transferred to or from controller 26, using for example, a memory device, such as a memory stick or memory card. Further, control module 30 may be configured to accept "plug-in" modules, which have their own processors and storage devices and which add additional features or functions to the controller. For example, a "plug-in" module may be used to expand the number of protocols, the number of phrases for translation, the number of languages into which the phrases can be translated, etc., described more fully below. Again, the software in the controller provides a GUI to organize the functions at display 38 and to generate screen images with various symbols and/or text windows and to allow the user to interface with the module based or display based controller 26.

As best seen in FIGS. 1, 2, and 10-12, control module 30 includes a control panel 30a and is mounted in the footboard 32 of bed 10. Control module 30 includes a housing 34 that is mounted for pivotable movement in footboard 32 and, further, in a manner so that the control module may be removed from the bed, as described in the reference applications. While references are made to the pending application for additional details, it should be understood that the present invention may be incorporated into other patient supports, and the references to the applications are for examples only.

Control panel 30a also includes a plurality of user interfaces 36 and a display 38, such as a touch screen display 38a. User interfaces 36, which are in communication with the controller (25 or module- or display-based controller), allow the user to select which prompts, conditions, features/accessories, or information that the user wishes to set, manage/monitor, control or review. As used herein, the term "prompt" is used broadly to mean any icon or text or indicator, including an audible indicator, that reminds the user of, for example, a protocol or a condition at the bed or a condition of a patient. Further as would be understood by those skilled in the art, the controller has stored therein a specified function associated with each user interface so that when a user interface is selected, the user interface will generate a signal to the controller, which will be identified by the controller and initiate processing on behalf of the controller associated with that function. For example, as will be more fully described below, some functions associated with the user interfaces are actuating functions, e.g. driving an actuator on the bed to raise or lower the bed or a section of the bed; others relate to storing and monitoring of parameters at the bed, e.g. the storing of patient weight or movement or other patient parameters or bed parameters, such as the bed angle or bed height, which are detected by sensors at the bed and which are monitored by the controller either continuously or when prompted by the user.

Further, user interfaces may be configured as a keyboard (including a touch screen keyboard) to enter information, for example, patient information, including bed assignment and room assignment information, the nurse assignment information, treatment protocols, if not already stored on the controller, and any other suitable information into the controller that could assist in the care and handling of the patient. Further, control panel 30a may incorporate one or more operational functions, including a translator, calculator, or conversion function.

In illustrated embodiment, user interfaces 36 comprise keypad-like buttons, which may be actuated by simply pressing the button; though, it should be understood that user interfaces 36 may comprise other user interfaces, such as areas on touch screen 38a or another touch screen provided at control panel 30a. Though reference is made to "touch" screen it should be understood that this use of "touch screen" covers screens that are sensitive to pressure or changes in magnetic field, capacitance, optical interference, or resistance. Further, the user interface may comprise a voice recognition system, including a microphone and voice recognition software, which may be stored in the controller.

When configured as a keypad (or touch screen area) optionally each user interface 36 includes an icon or text associated therewith to represent the prompt, condition, feature, or function that the user interface is associated. For example, with reference to FIG. 2 user interface 36a includes an "i" to designate the iBed™ functions of bed 10 available from Stryker Corporation of Kalamazoo, Mich. User interface 36b includes an icon in the form of a graphical representation of the patient support surface. User interface 36c includes text, namely, "Bed Controls" to indicate the type of bed control function associate with the user interface. User interface 36d includes an icon in the form of a lock to indicate a locking function. User interface 36e includes an icon in the form of a scale to indicate a weighing or scale function. User interface 36f includes text, namely, "Bed Exit", to indicate a bed exit function. User interface 36g includes text, namely, "Options", to indicate other features/accessories and functions that are associated with the user interface, including setting the time, controlling the settings, such as for a TV or light, changing the language that is displayed by the display or displays at the patient support, reviewing the bed or patient history, and maintenance functions, all more fully described below.

In addition, control panel 30a includes a second set of user interfaces 40. In the illustrated embodiment, user interfaces 40 comprise buttons 40a, 40b, 40c, and 40d, all of which provide input into controller 25 (or the module or display based controller, again, more fully describe below), which in turn processes the input. For example, the controller may, in response to the input from a button 40a, generate drive signals for one or more of the actuators on the bed to configure the bed into a commonly used configuration such as an HOB 30° orientation. In the illustrated embodiment, when button 40b is selected, the controller may generate drive signals to one or more actuators to configure the bed in another commonly used configuration, such as a vascular position configuration. When button 40c is pushed, the controller may generate drive signals to actuate, for example, the brake on the bed. Similarly, when button 40e is pressed, the controller may generate signals to deactivate the brake. Button 40d triggers the controller to generate drive signals to drive, for example a fifth wheel on the bed (see reference application for a description of a suitable bed driver).

Further control panel 30a includes a plurality of indicators 42, such as LED lights or the like, which indicate the status of various features at the bed. The indicators may, as a part of the bed indication system, indicate whether the bed is in a desired or undesired configuration, i.e. when one or more of the monitored conditions are either in an undesirable state or a desired state.

For example, the indicators may indicate the bed exit status (such as whether the bed exit system is enabled) or a bed status, such as when a side rail is down, the brake is not set, the on-board battery is low, to call maintenance, and a lock out status. When used to define whether a monitored condition is in a desired state, indicators 42 may comprise a green light to indicate the condition is in a desired configuration for that function. Where the condition is not in a desired state, an amber or red indicator light may be used. In addition to the indicator lights, an additional indicator may be provided, such as an audible alarm or warning, or the like, whether locally mounted on the bed or mounted off the bed, for example in the room. As will be more fully described below, text displayed on touch screen 38a may also provide additional information as to the condition (or conditions of the bed) when the condition (or conditions are) indicated to be not in their desired state.

As previously mentioned, the controller is in communication with both the user interfaces and the display and, further, generates a display at the touch screen 38a in response to actuation of a user interface. For example, when a user interface 36 is actuated, the controller generates a screen image at touch screen 38a that is associated with the particular user interface that is selected. As noted above, the controller may comprise a computer that has display 38 as part of the computer.

Figure 16:
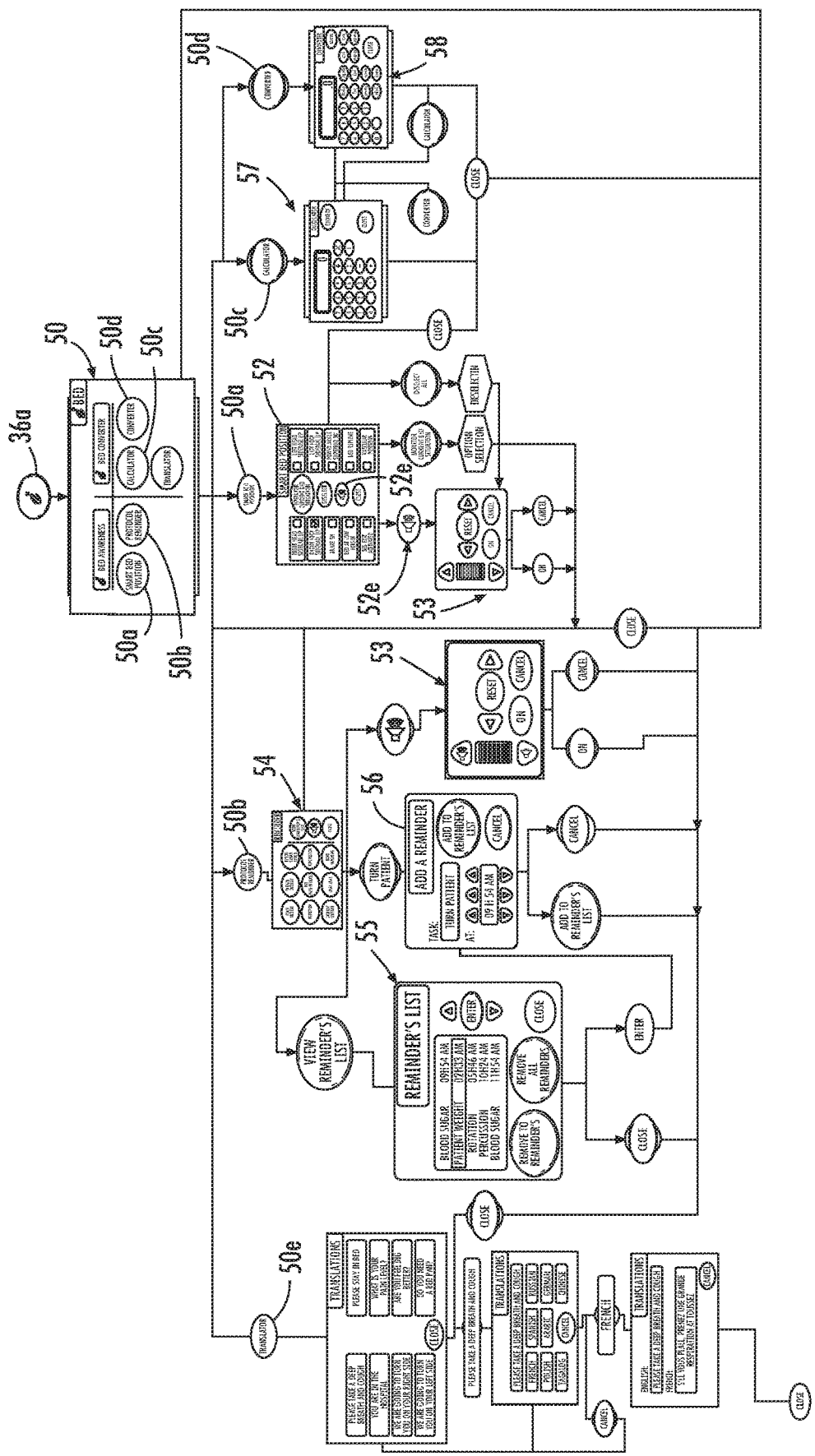
FIG. 16 illustrates a screen image provided by the controller at the display.
Figure 28:
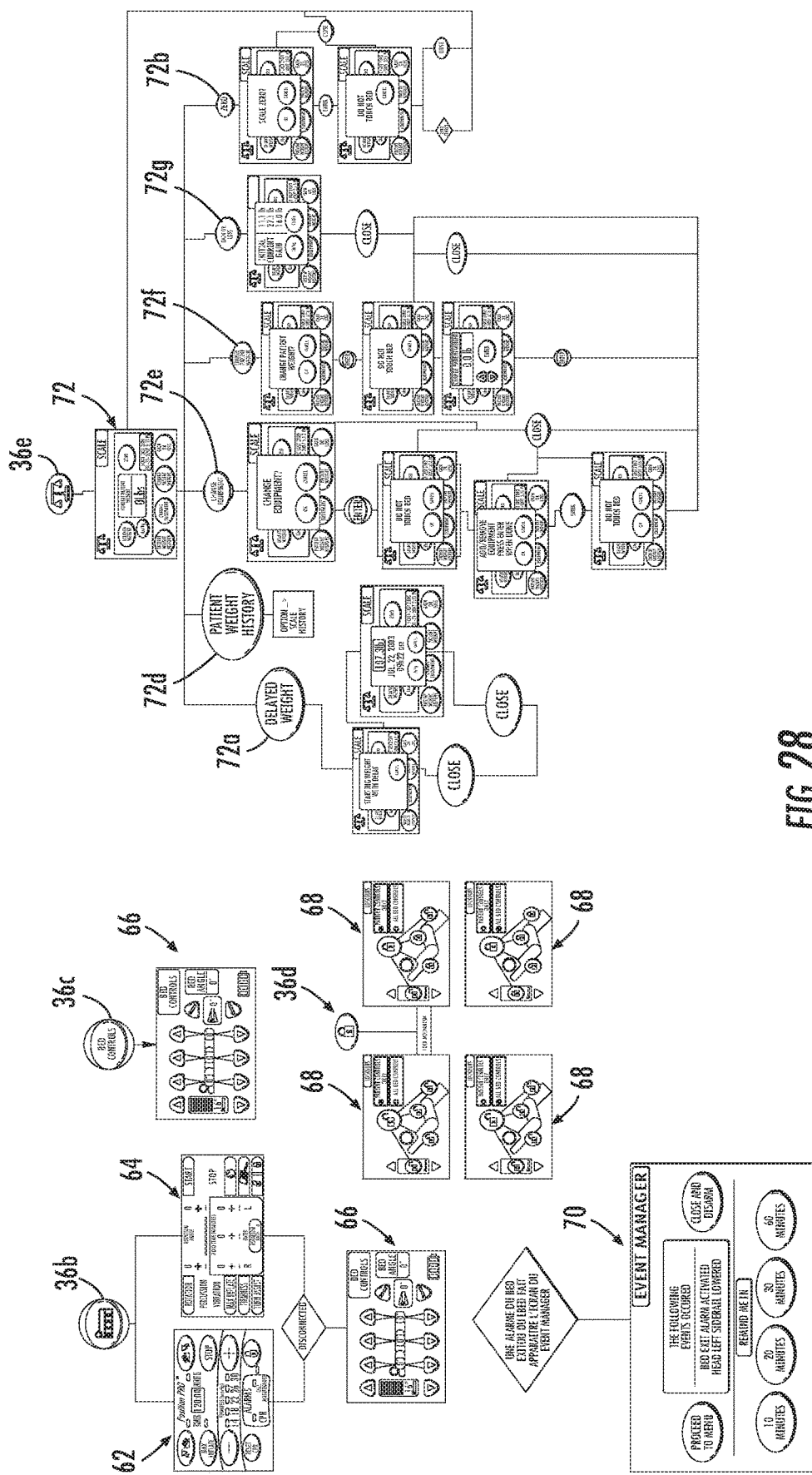
FIG. 28 illustrates a screen image provided by the controller at the display.
Figure 40:
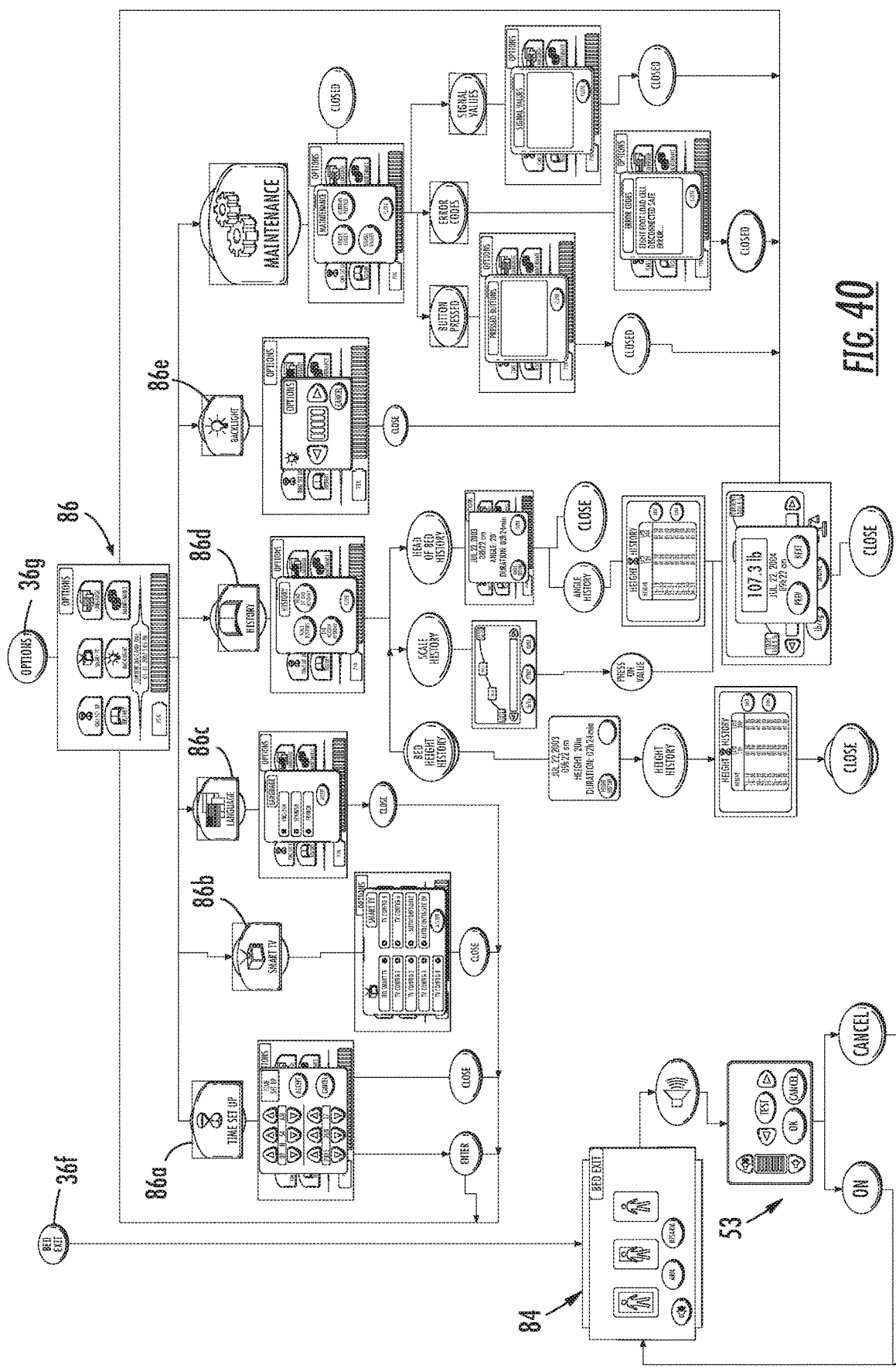
FIG. 40 illustrates a screen image provided by the controller at the display.

When any one of the user interfaces 36 is selected and actuated, by, for example, being touched, a display screen image associated with the user interface that is selected will be generated by the graphic user interface of the controller. Referring to FIGS. 16, 28, and 40, each user interface includes one or more screen images to provide enhanced functionality and care of the patient. Further, the screen images provide menus and in some cases windows for text and/or icons, which may provide a graphical representation of the function being selected.

iBed Functions

Figure 17:
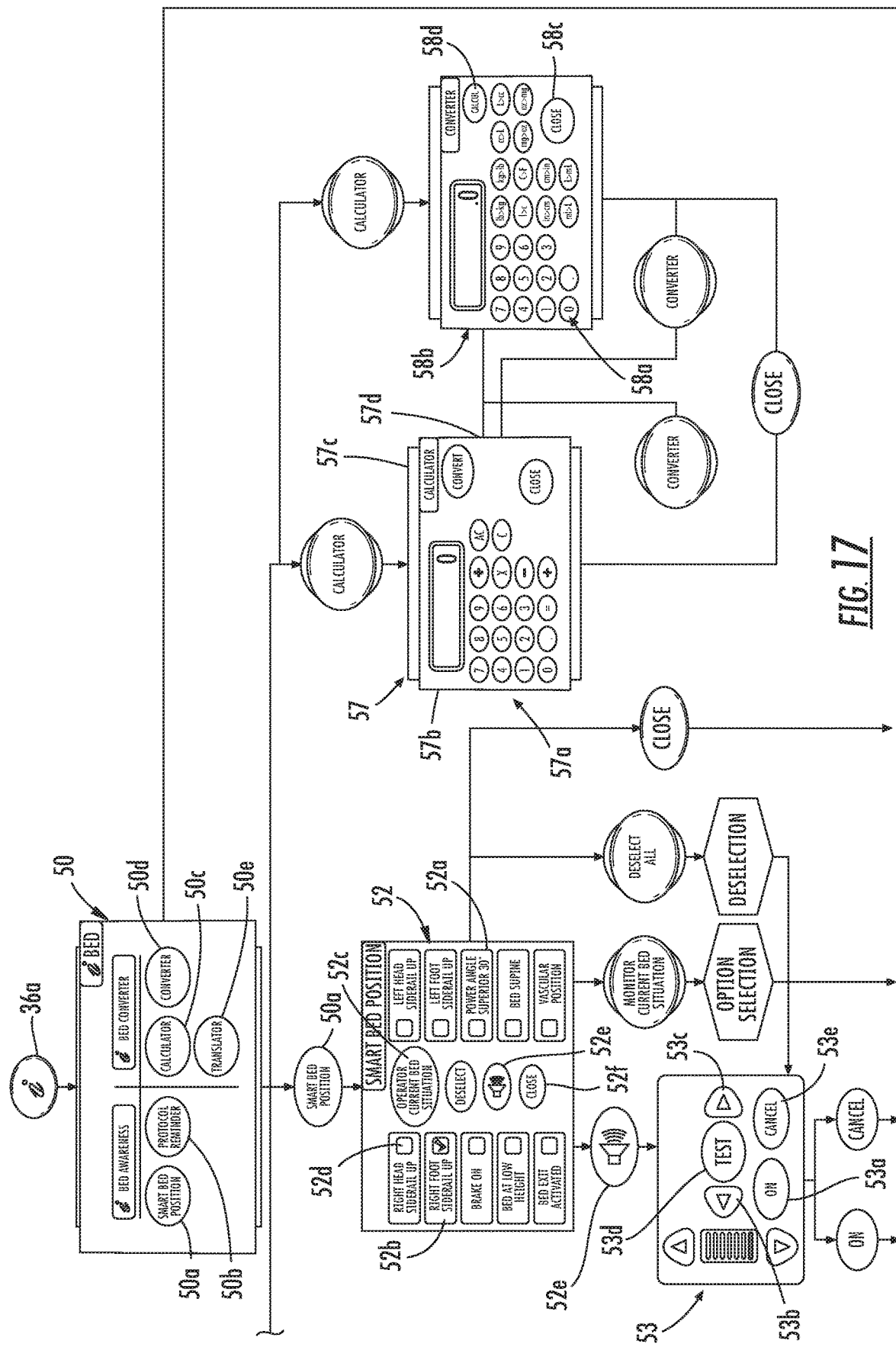
FIG. 17 illustrates a screen image provided by the controller at the display.

Referring to FIGS. 16 and 17, when the iBed user interface 36a is selected, screen image 50 will be generated by the controller and displayed at touch screen 38a. Screen image 50 provides a menu and includes a plurality of additional user interfaces in the form of touch sensitive areas of the screen image that generate and send signals to the controller to generate further screen images for further options and selections.

Figure 18:
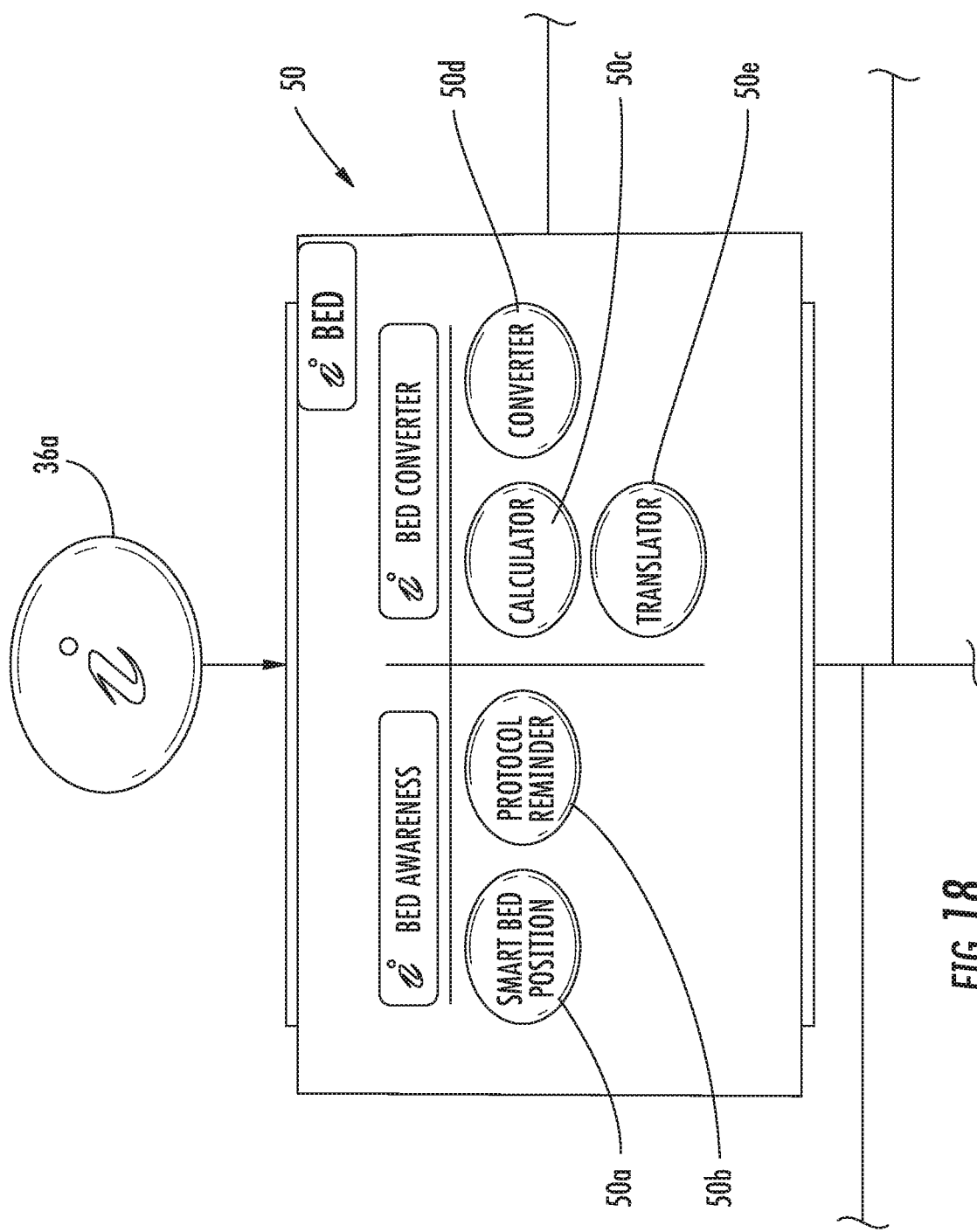
FIG. 18 illustrates a screen image provided by the controller at the display.

As best seen in FIG. 18, screen image 50 includes a touch screen area 50a for selecting options relative to the bed position, a touch screen area 50b for selecting protocol prompts or reminders, a touch screen area 50c for selecting a calculator function, a touch screen area 50d for selecting a conversion function, and a touch screen area 50e for selecting a translation function. It should be understood that when reference is made to a user interface being actuated by a user, such as by applying pressure to the user interface, the user interface generates a signal to the controller, which in turn generates a signal responsive to the user interface function. For example, where the user interface is associated with a bed position, the controller will generate a drive signal to the respective actuator.

Figure 19:
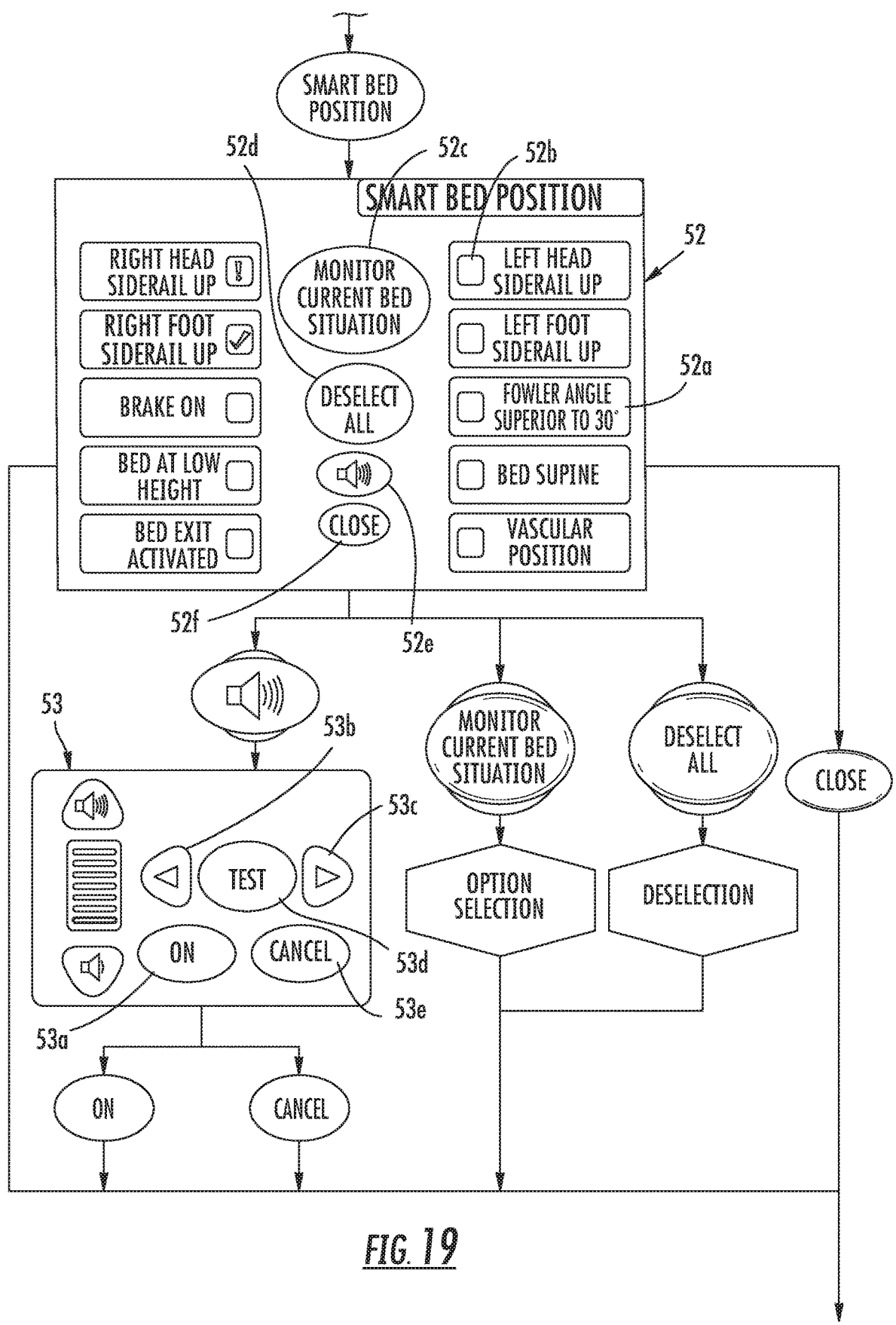
FIG. 19 illustrates a screen image provided by the controller at the display.

When touch screen area 50a is selected by a user, a bed position screen image 52 is generated the controller and displayed at display 38, which is best seen in FIG. 19. Bed position screen image 52 also includes a menu in the form of a plurality of touch screen areas 52a associated with a bed position condition, including, for example, right head side rail up, right foot side rail up, brake on, bed at low height, bed exit activated, left head side rail up, left foot side rail up, fowler angle superior to 30 degrees, bed supine, and vascular position. When a touch screen area 52a is selected by the user, an icon will appear in a window 52b indicating that the particular bed position condition associated with the screen area 52a has been selected.

Further, screen image 52 includes a touch screen area 52c which when selected allows the user to indicate to the controller when a selected bed position condition is to be monitored. Touch screen area 52d allows a user to deselect all the bed position conditions from being monitored. Further, touch screen area 52e allows a user to select an alarm, for example an audible alarm, to be activated when a bed position condition that is monitored by the controller occurs.

When touch screen area 52e is actuated, another screen image 53 is generated by the controller and displayed at display 30, which allows the user to select whether or not the audible alarm will be actuated by the controller and further to select the volume of the alarm. For example, screen image 53 includes a plurality of touch screen areas to generate signals to the controller, which in turn generates control signals relative to the alarm. For the illustrated embodiment, touch screen 53 includes a touch screen area 53a, which when pressed generates a signal to the controller, which then flags the alarm for actuation when actuate the selected bed condition being monitored occurs. Screen 53 also may include touch screen areas 53b and 53c, which are provided to signal to the controller to increase or decrease the volume of the alarm. Screen 53 further may include an area 53d to signal to the controller to test the alarm so that a user may determine whether the volume is sufficient and, further, whether it is working. In addition, touch screen image 53 may include an area 53e which when actuated generates a signal to the controller to cancel the alarm. After a preselected period of time has elapsed as measured by the controller, controller then closes screen 53 and returns display 38 to screen 52. Once returned to screen 52, a user may close screen 52 using touch screen area 52f, which returns the display to the iBed screen image 50.

Figure 22:
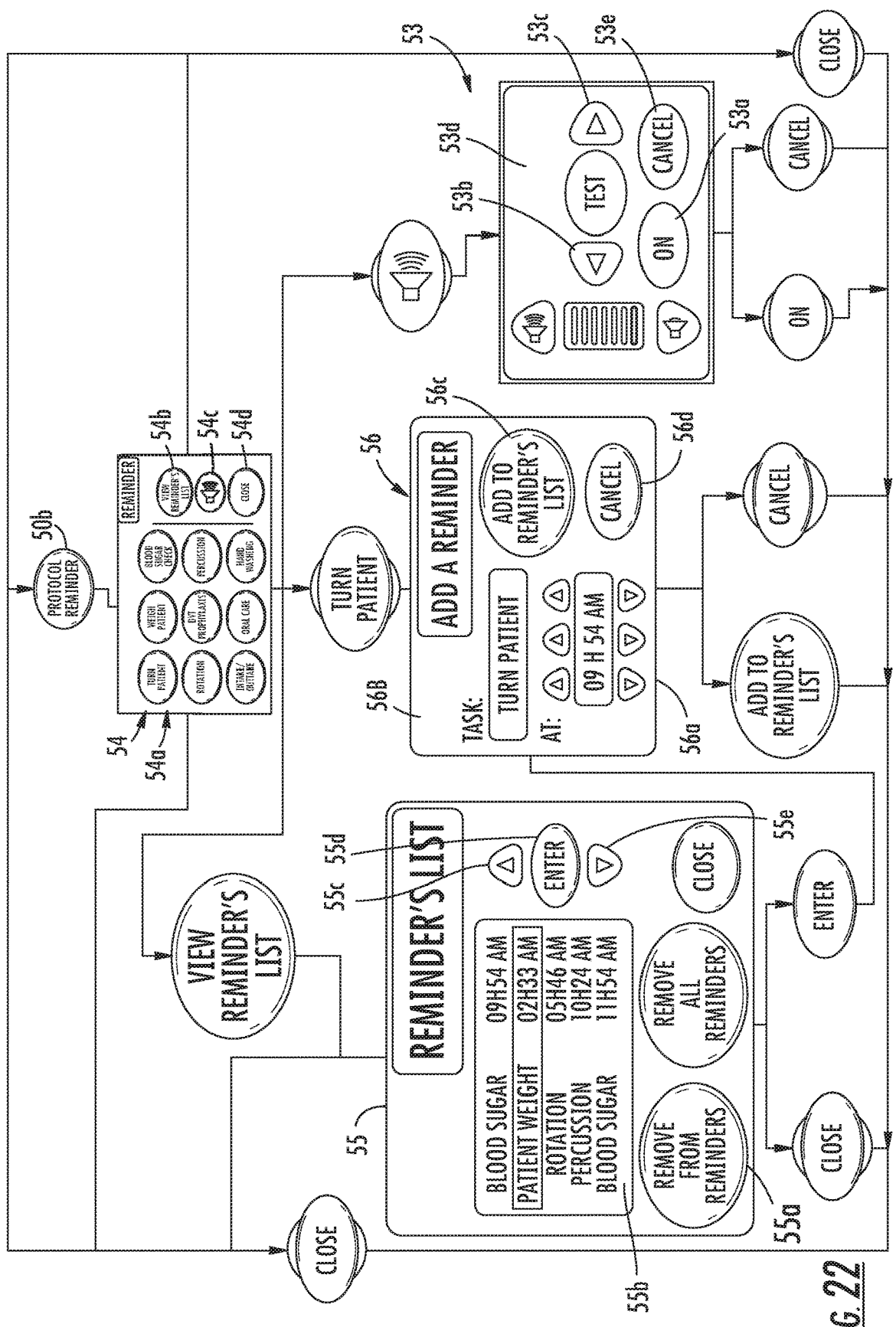
FIG. 22 illustrates a screen image provided by the controller at the display.

Referring to FIGS. 18 and 22, when region 50b is selected, the controller will generate and display a protocol reminder screen image 54 at display 38, which displays a menu of protocols that can be selected by the user. In the illustrated embodiment, screen image 54 includes a menu of nine protocols, for example, for: turning the patient, weighing the patient, checking the patient's blood sugar, rotating the patient, applying DVT prophylaxis, applying percussion, for intake/outtake, for administering oral care to the patient, washing the patient's hands. It should be understood that the number of protocols may be reduce or increased. Additional or alternate protocols that may be included include protocols relating to: infection control or wound care, such as checking a patient's dressing; checking the patient's vitals, including checking the patient's heart rate, the patient's temperature, oxygen levels; checking the cleanliness of the bed; checking the patient's restraints when the patient is restrained; and generally checking the patient's position on the bed to minimize the risk of the patient falling or getting trapped in a undesirable position on the bed. Further, as will be more fully described below, protocols may be created using the protocol reminder user interface.

Figure 23:
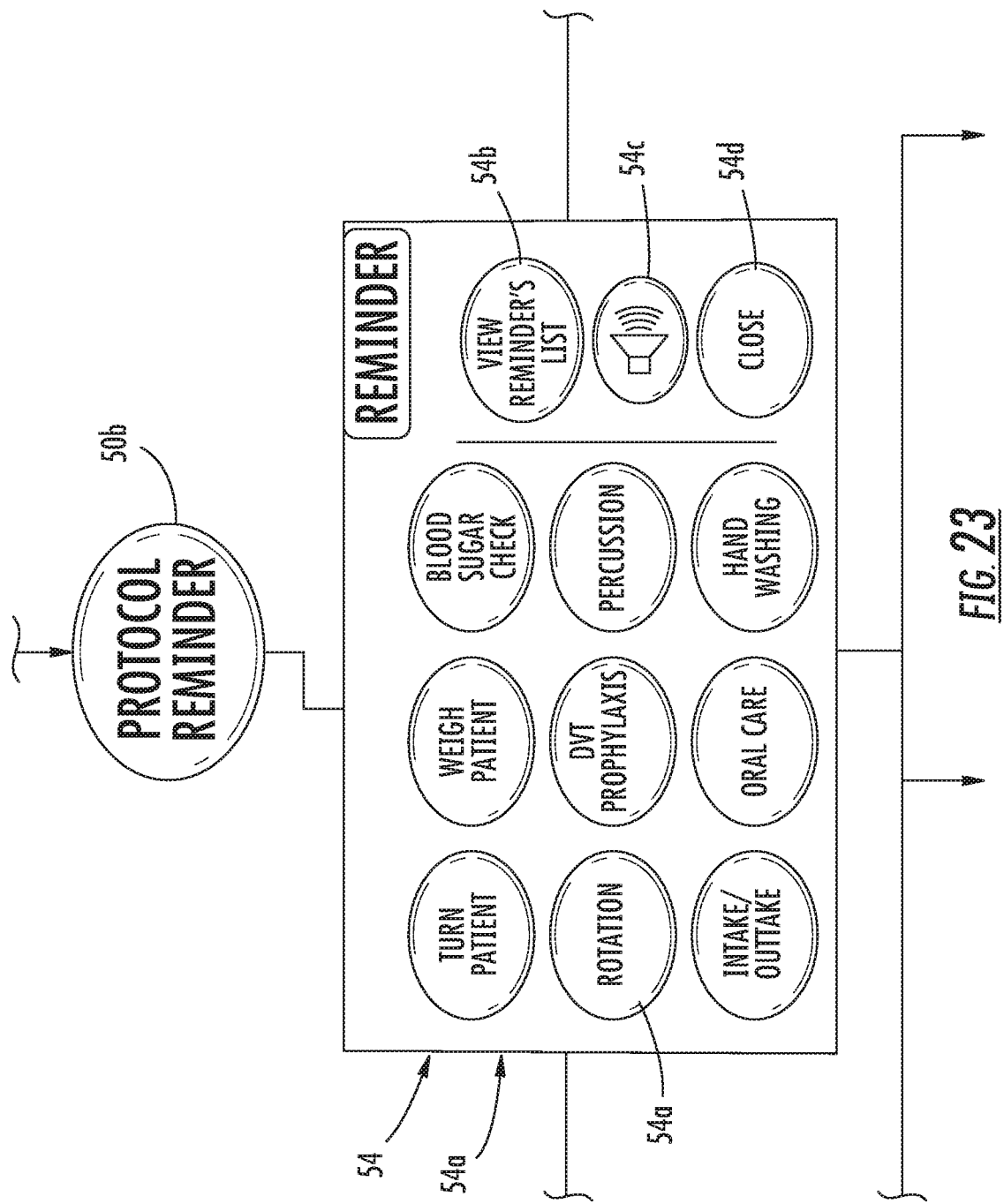
FIG. 23 illustrates a screen image provided by the controller at the display.
Figure 24:
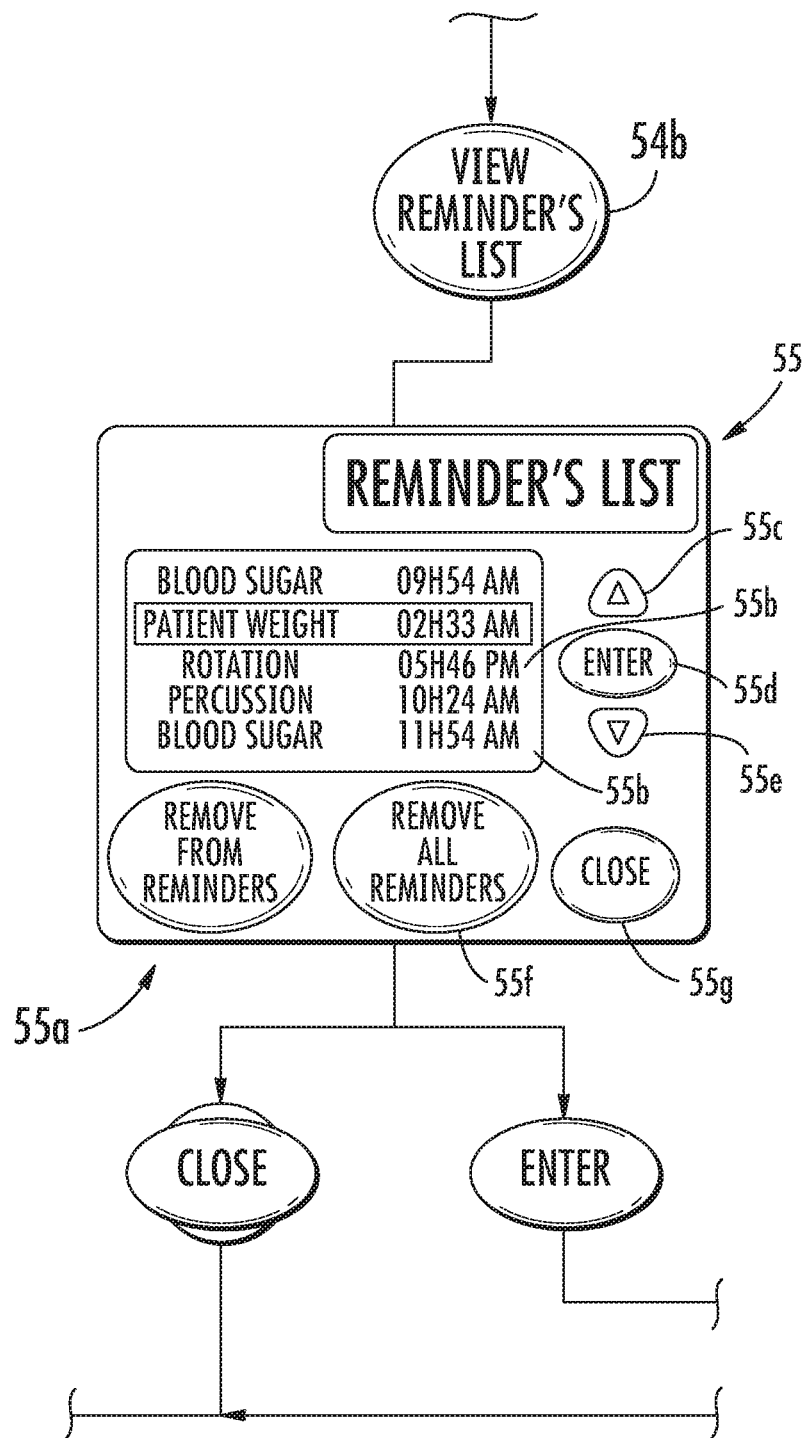
FIG. 24 illustrates a screen image provided by the controller at the display.
Figure 25:
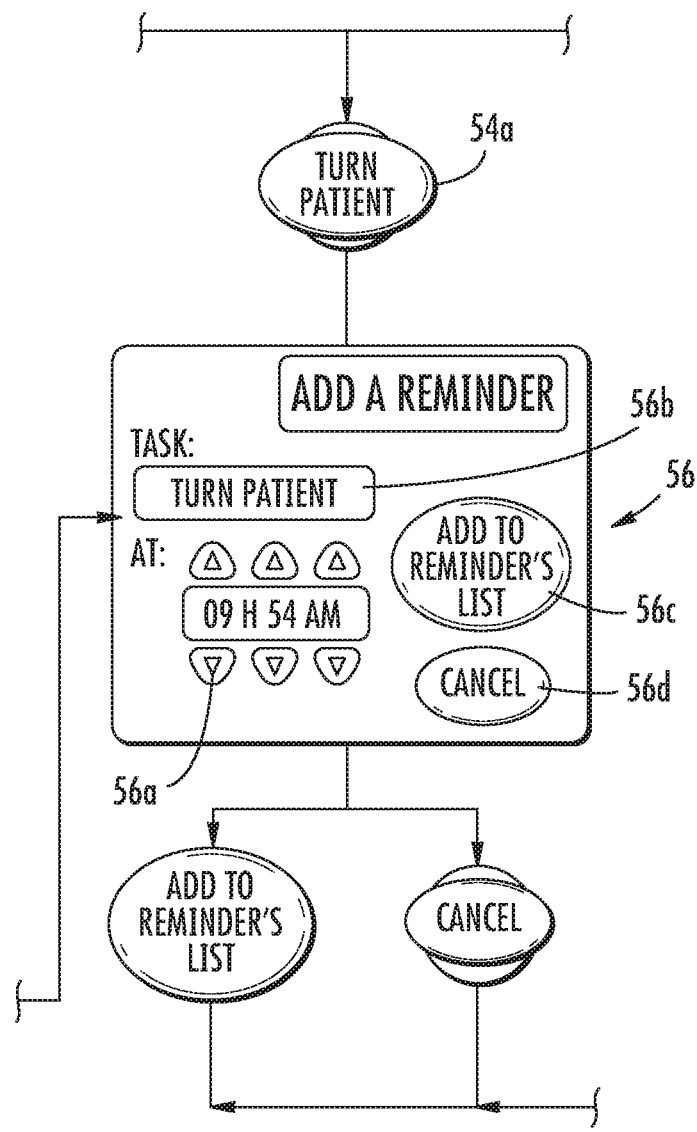
FIG. 25 illustrates a screen image provided by the controller at the display.
Figure 26:
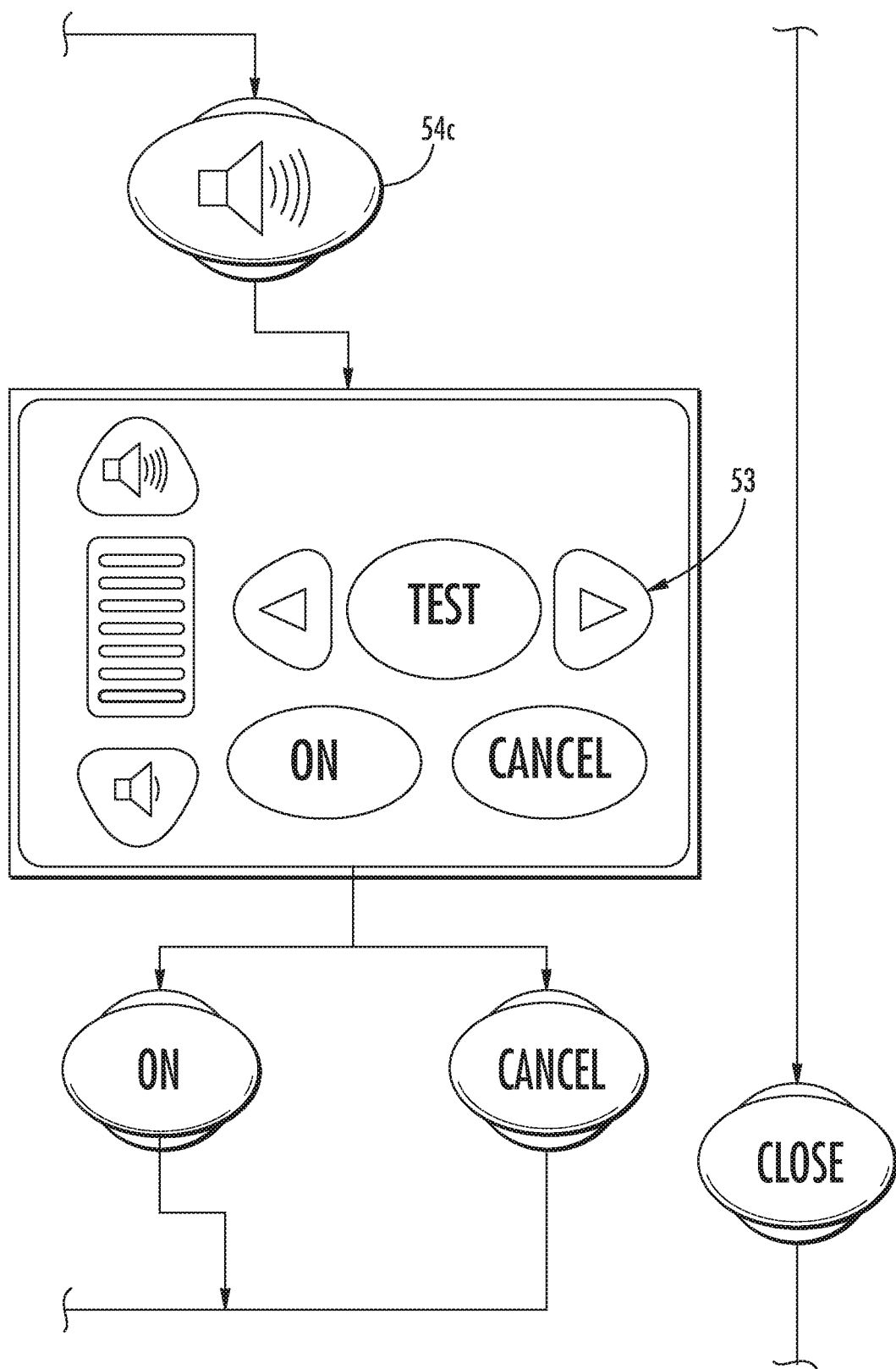
FIG. 26 illustrates a screen image provided by the controller at the display.

As best seen in FIG. 23, screen image 54 includes nine touch screen areas 54a, each associated with a protocol, such as the protocols listed above, which are stored in the controller's memory or storage device, for example in a look up table. When one of the touch screen areas 54a is selected, the protocol associated with that touch screen area (denoted in the illustrated embodiment by text—though icons could also be used) will be stored in the controller's memory or storage device as a selected protocol. Further, once a touch screen area 54a is selected, the controller will generate another screen image 56, which also has a plurality touch screen areas that allow the user to set one or more parameters associated with the protocol. For example, touch screen 56 includes touch screen areas 56a that select the time, namely hour, minutes, and AM or PM, to be associated with that particular selected protocol (identified in window 56b) and the time at which controller will generate a prompt or reminder to be generated at display 38 and/or to actuate the alarm. Further, touch screen 56 may also include a touch screen area 56c that allows the user to add the protocol and its associated reminder time to a protocol reminder list (FIG. 24) stored in the controller's memory or storage device. Once added to the list, the controller will close screen image 56 and return to screen image 54.

Referring again to FIG. 23, screen image 54 is provided a touch screen area 54b which when actuated generates a signal to the controller to display the reminder list to allow a user to view the reminder list. For example, when area 54b is selected, a reminder list screen image 55 (FIG. 24) is displayed by the controller at display 38, which includes a window 55b that displays in text form each reminder that has been selected and its associated reminder time and also a plurality of touch screen areas 55a, 55c, 55d, and 55e, which allow the user to modify the list. For example, touch screen areas 55c and 55e allow the user scroll through the list of reminders in window 55b. Using touch screen area 55d, the user can then select an entry from the list, which causes the controller to display screen image 56 (but with the selected entry displayed at display 56b), which allows the user to change the time for the selected protocol from the list in window 55b. Touch screen areas 55a, 55f, and 55g are provided that generate a signal to the controller to remove a protocol from the list when it is selected (by touch screen area 55d); remove all reminders; or close the screen image to return to the reminder screen image 54, respectively.

Screen image 54 also provides a touch screen area 54c for setting an audible alert as the reminder. When actuated, screen area 54c signals to the control system to display screen image 53, which allows the user to actuate the audible alarm setting for the selected protocols in the protocol list and, further, to set the volume of the alarm, as well as test the alarm, as noted above. In addition to providing a menu of specific protocols, the controller may initially generate a menu of categories of protocols, which when selected generate another touch screen with a menu of the specific protocols associate with the selected category. For, example, a touch screen display may list reminder groups, such as skin care, pulmonary, fall prevention, neurological, gastrointestinal, patient weight, mobility, blood, or a restraint category. Once the category is selected, the controller will then generate a list of protocols for that category—e.g. for the pulmonary group, the controller may list for example, HOB Elevation, DVT Prophylaxis, Rotation Percussion, Sedation Assessment, Daily Sedation Vacation, Stress Ulcer Prophlaxis, Oral Care, Vibration Times, etc.

Figure 20:
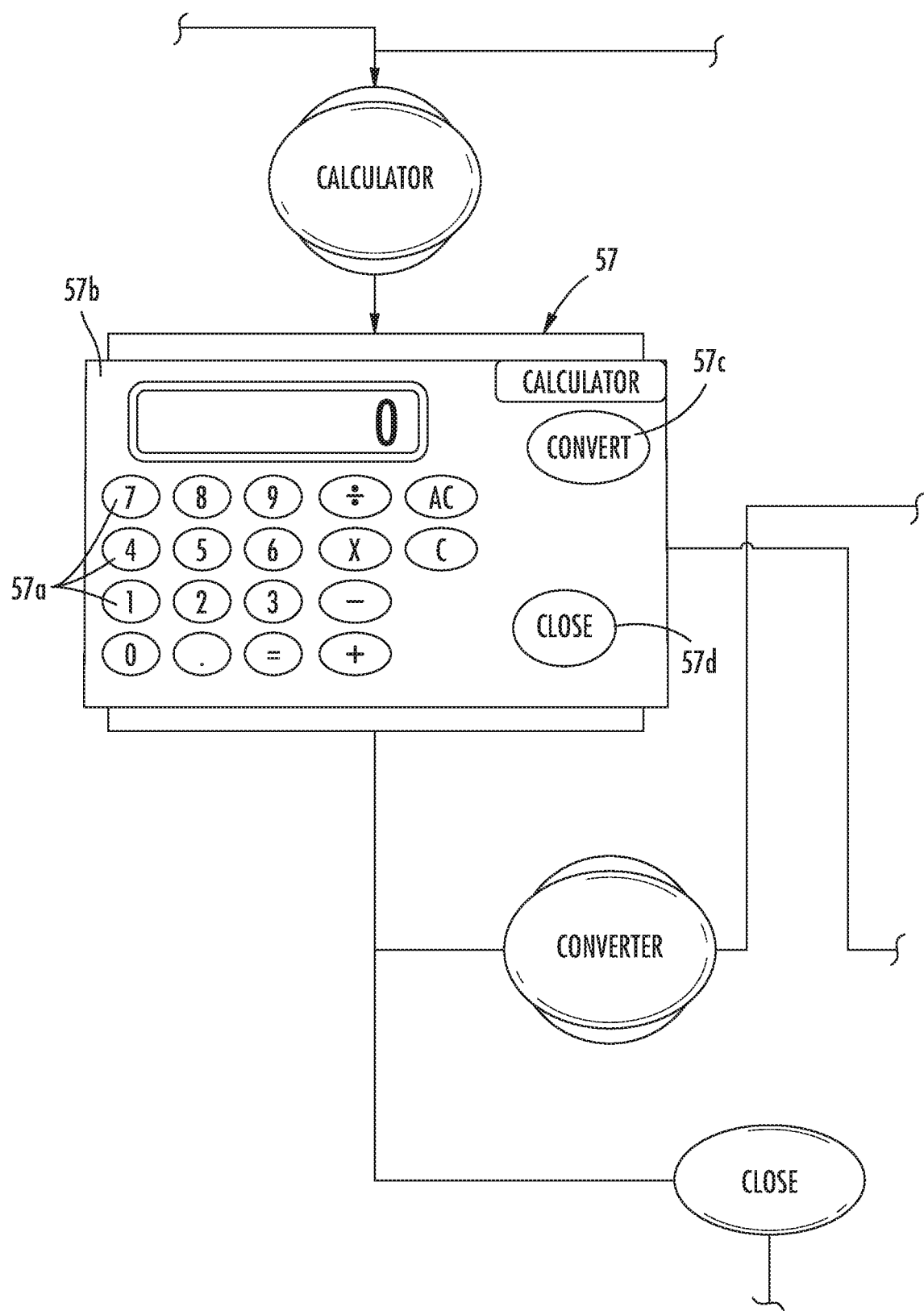
FIG. 20 illustrates a screen image provided by the controller at the display.
Figure 21:
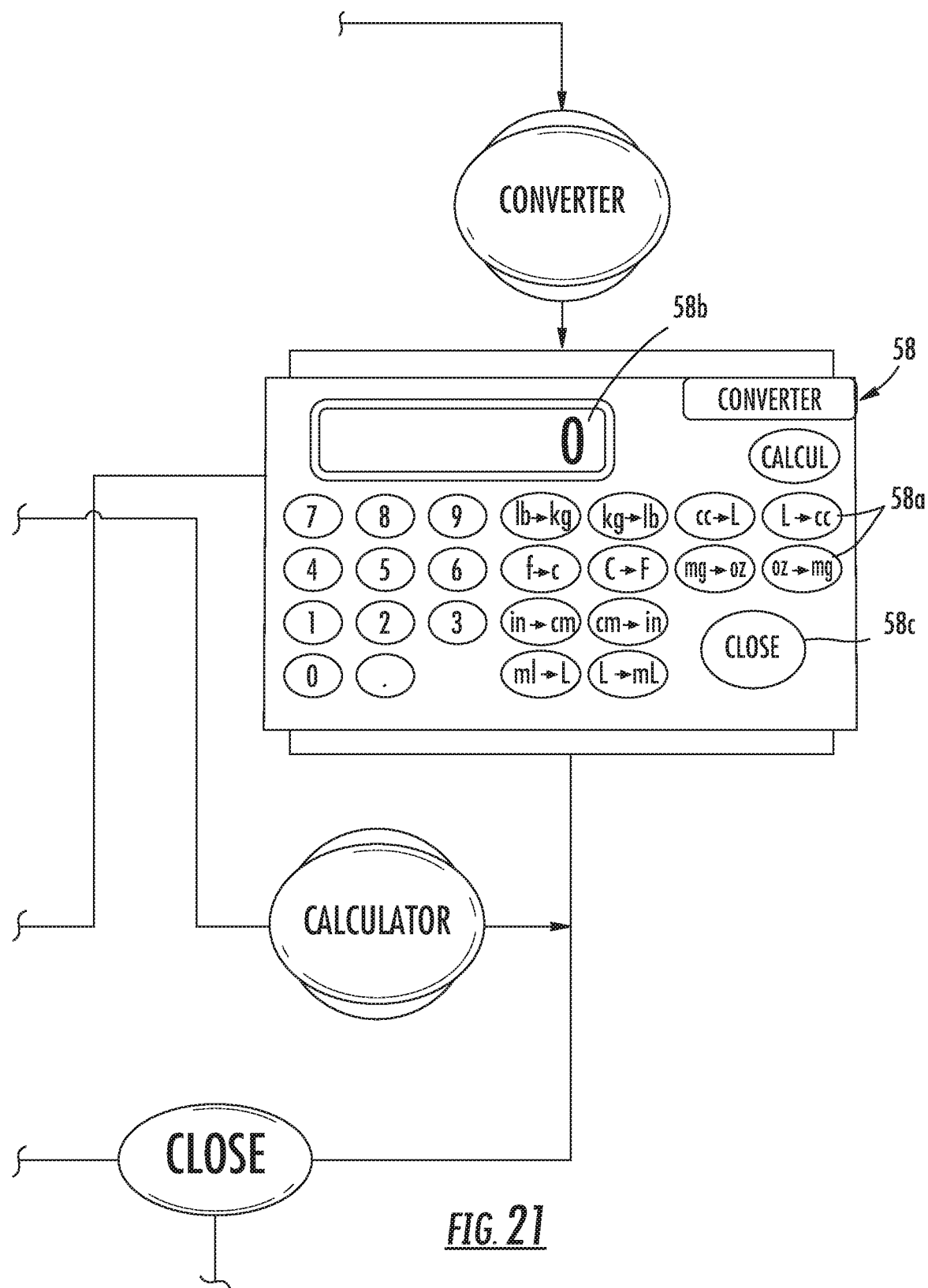
FIG. 21 illustrates a screen image provided by the controller at the display.

In addition to allowing the user to select which bed conditions or patient conditions are to be monitored and to select protocols for prompts or reminders, screen image 50 provides computational functions. As best seen in FIGS. 18, 20, and 21, when touch screen area 50c or 50d is selected, the controller will display a computer screen image 57 (FIG. 20) or a conversion screen image 58 (FIG. 21), respectively. Screen image 57 is configured as a calculator with a plurality of touch screen areas 57a for inputting numerical values into the controller and selecting the operations to be performed on the numerical values by the controller, which are input using the touch screen areas. Screen image 57 also includes a window 57b that displays the input values and the results of the operation performed the input values (into the controller) and a touch screen area 57c that allows the user to signal to the controller to switch to the conversion screen image 58. Further, screen image 57 includes a screen area 57d to send a signal to the controller to close the screen image (57) and return to screen image 50.

Screen image 58 is similarly provided with screen areas 58a for inputting numerical values and selecting the conversion operations to be performed by the controller on the numerical values that are input into the controller and a window 58b that displays the input and results. Screen image 58 also includes a touch screen area 58c for signaling the controller to close the touch screen image (58) and return to touch screen image 50. Screen 58 also includes a touch screen area 58d that allows the user to signal to the controller to switch to the calculator touch screen image (57).

Figure 27:
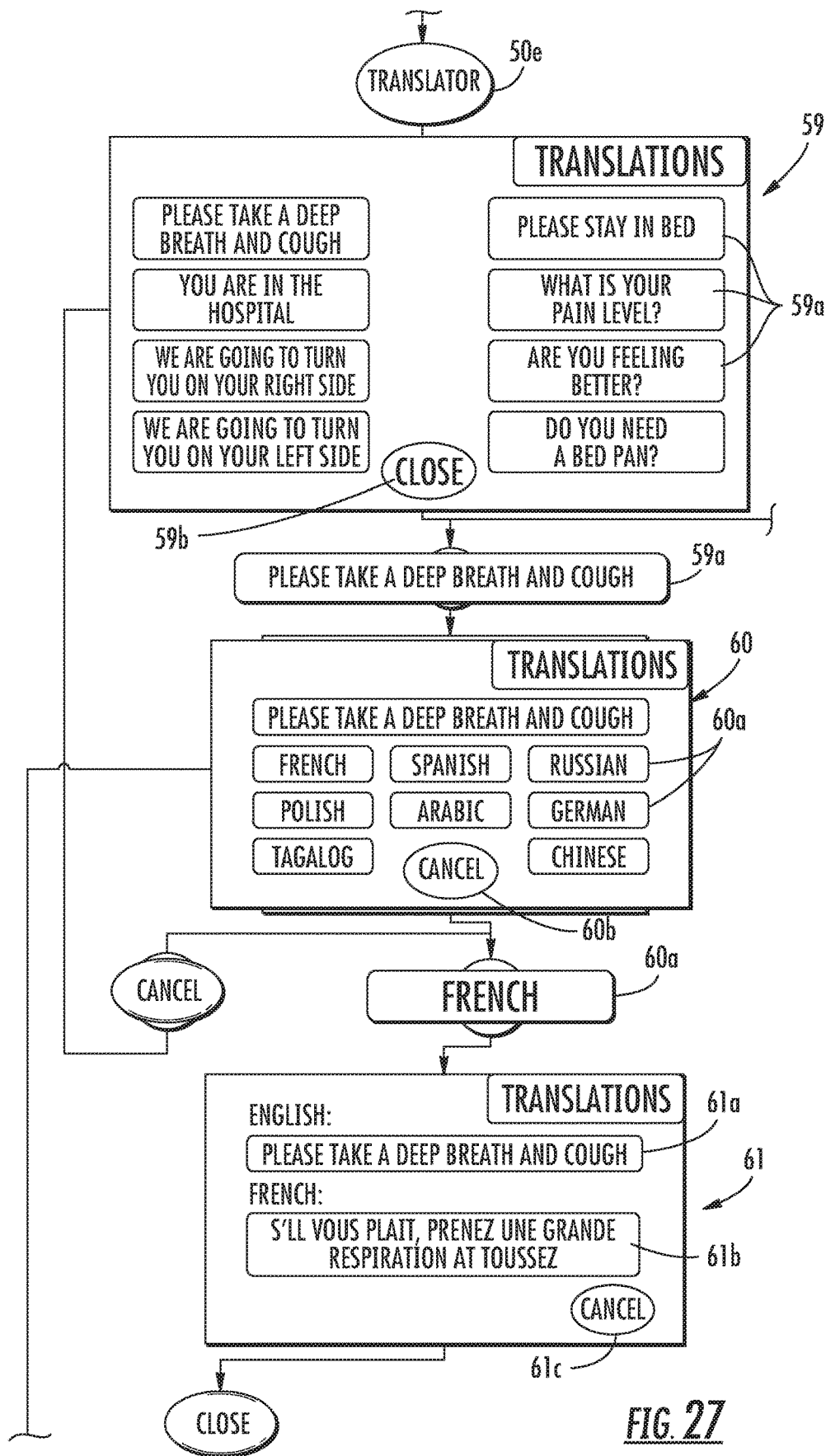
FIG. 27 illustrates a screen image provided by the controller at the display.

In addition, iBed screen image 50 provides a translation function. When touch screen area 50e is selected, translation touch screen image 59 (FIG. 27) will be generated and displayed by the controller at display 38. Screen image 59 provides a menu of phrases and includes a plurality of touch screen areas 59a, each associated with a phrase. When a phrase is selected by the user, the controller will then generate another screen image 60, which provides a menu of languages into which the phrase can be translated and includes a touch screen area 60a associated with each language. Once the user selects the language, the controller will generate yet another screen image 61 with two text windows 61a and 61b, one that displays the original phrase (61a) to be translated and the other to display the translation (61b). Each of the screen images may include a screen area (59b, 60b, and 61c) to close the respective screen image—alternately, the controller may close the screen images after a pre-selected period of time has elapsed, as measured by the controller.

Optionally, rather that the user reciting the translation, the controller may be configured to play a pre-recorded message (in for example an MP3 player or other recording/playing device) containing the phrase using the speakers at the head end of the bed or using speakers provided at the footboard, including in control module 30.

Support Surface

Figure 29:
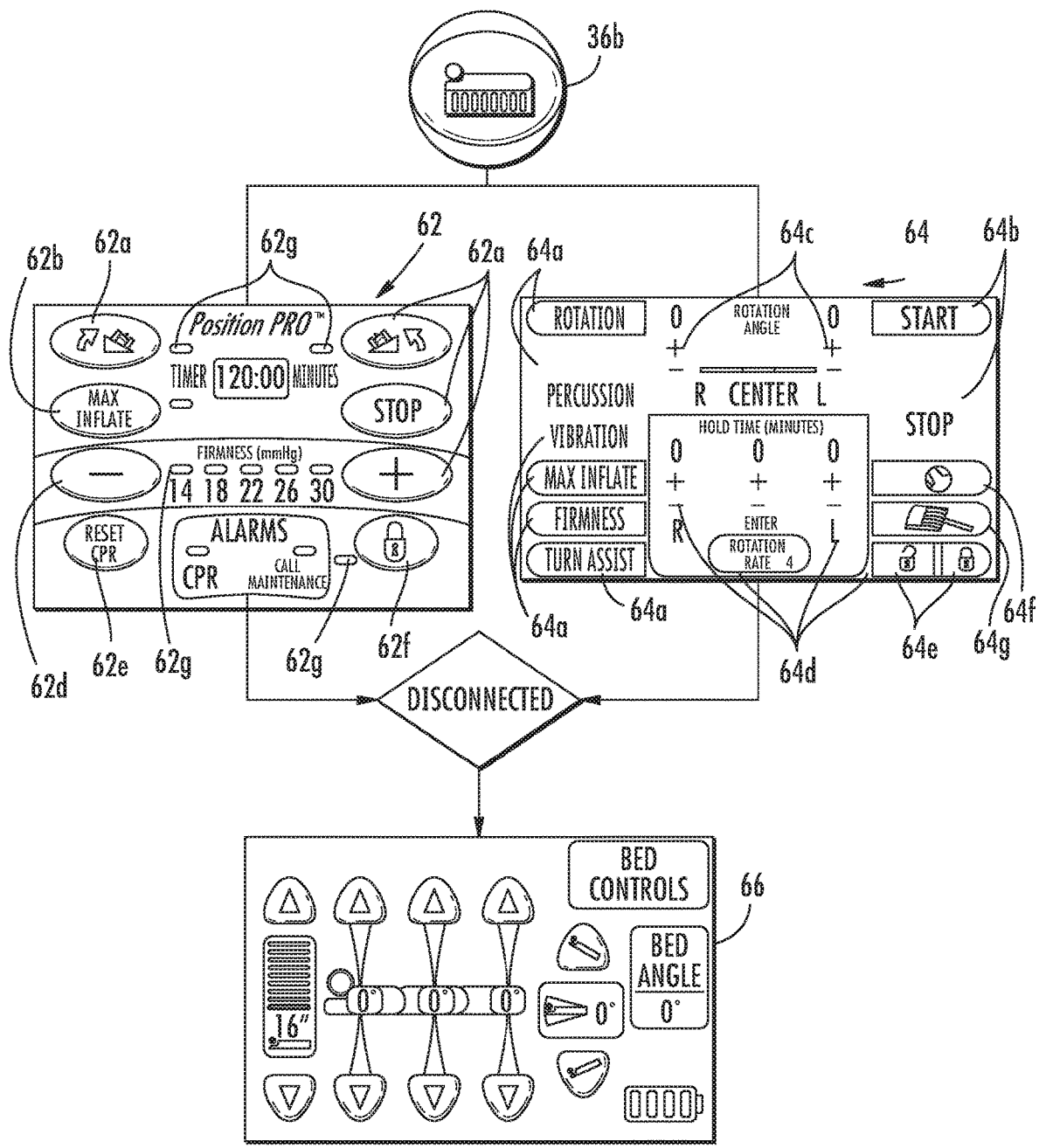
FIG. 29 illustrates a screen image provided by the controller at the display.

Returning again to FIG. 2, when user interface 36b is selected, controller will generate a touch screen image 62 (see FIGS. 28 and 30), which displays various features related to the mattress and in the illustrated embodiment includes a menu of functions relating to the patient surface, namely the mattress. In the illustrated embodiment, display image 62 (FIG. 29) includes user interfaces for generating signals to the controller to adjust the firmness of the support surface, as well as turning of the patient. To achieve this, the menu is provided by a plurality of touch screen areas 62a, 62b, 62c, 62d, 62e, and 62f, which generate a signal to the controller to turn the patient (62a), for example by actuating the inflation of bladders provided at the patient support surface, to provide maximum inflation (62b) of the bladders, to stop the inflation (62c), to increase or decrease the firmness (62d) by adjusting the air in the bladders, to reset the CPR (62e), and to lock the bed functions from access to the patient (62f).

Figure 2:
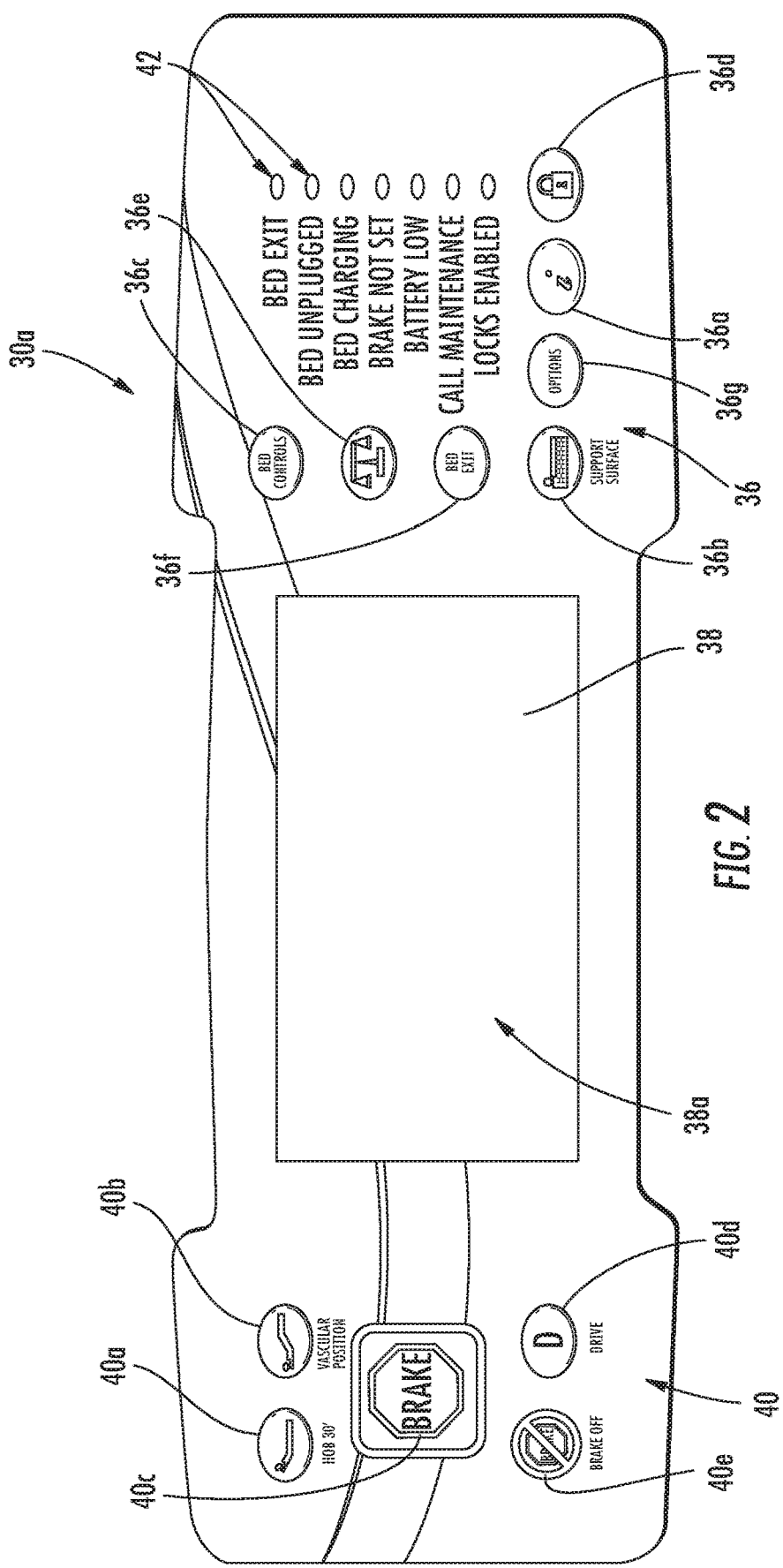
FIG. 2 is a front elevation of a patient control panel of the control module of present invention.

Further, indicators 62g, such as regions of the screen that change color, for example, may be associated with each function and indicate when a particular function is selected. In addition, indicators 62g can be provided to indicate a parameter of the function. For example, the firmness function may have a series of indicators 62g to provide an indication of the degree of firmness to thereby provide feedback to the user. Although not illustrated, screen image 62 may also include a touch screen area to allow a user to close the screen image and return to starting screen image at touch screen 38a (FIG. 2).

A second screen image 64 is generated by the controller with the selection of touch screen area 636b. Screen image 64 includes a plurality of touch screen areas 64a also associated with the patient surface of the bed, which include for example a rotation function to inflate portions of the mattress to rotate the patient, a percussion treatment function, a vibration function, a maximum inflate function, a firmness function, and a turn assist function. Additional touch screen areas are included that provide start and stop functions (64b), allow a user to select for example, the angle of rotation (64c) when the turn assist function (64a) is selected. Further, touch screen areas 64d are provided to allow a user to select a time and also the length of the treatment in the case of the vibration and or percussion treatment, as well as the level of intensity. Additional touch screen areas 64e are provided to lock or un-lock various features of the various functions of display screen image 64. Touch screen area 62f is provided to turn off the alarm at the bed, and touch screen area 64g allows the user to look up information about the patient, which may be stored in the controller.

Once the functions of screen images 63 and 64 are completed, or a pre-selected time has elapsed as measured by the controller, the controller may, rather than returning to starting screen image at screen 38a, display a bed control screen image 66, described more fully below in reference to when user interface 36c is selected.

Bed Controls

Figure 30:
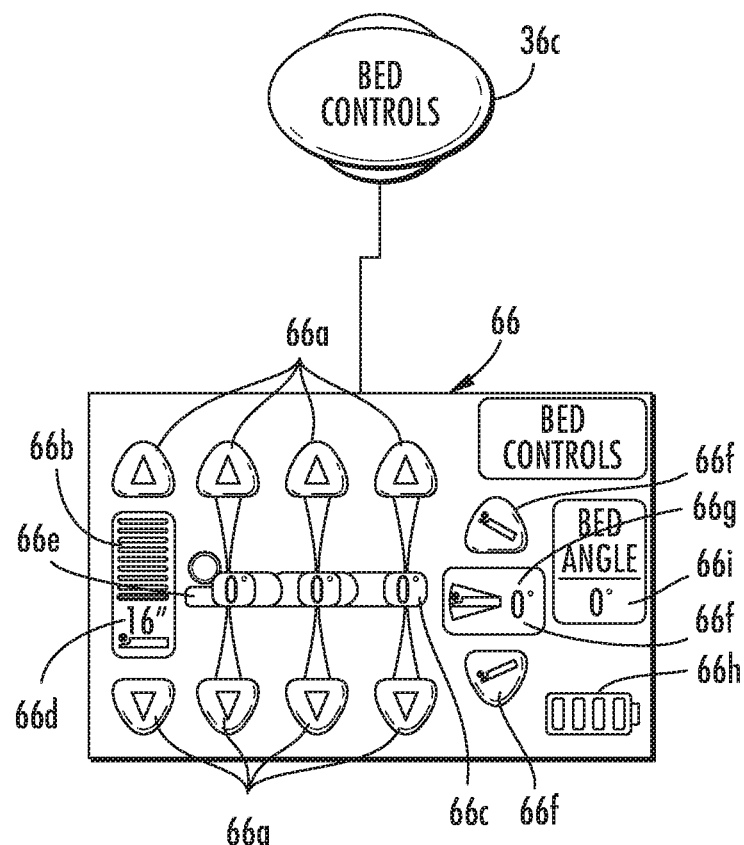
FIG. 30 illustrates a screen image provided by the controller at the display.

Referring to FIGS. 28 and 30, when user interface 36c is selected by a user, the controller will generate bed control screen image 66. Screen image 66 includes a plurality of user interfaces in the form of touch screen areas 66a, which allow a user to send a signal to the controller 25 to change the position of the deck by actuation of the deck actuators and/or the height of the patient support surface. Screen image 66 includes various icons 66b, 66c that schematically show the adjustments. For example, icon 66b schematically illustrates the raising of the support surface and further includes a text window 66d that displays a numerical value representing the height of the patient support surface relative to the ground surface. In reference to the deck position, icons 66c represent the deck sections and further include a text window 66e for displaying the angular position of the respective deck section. Further the respective deck sections are aligned with corresponding portions of the touch screen areas that actuate the respective deck sections to provide a cognitive association between the user interfaces and the sections of the deck that are moved in response to their selection.

In the illustrated embodiment, each touch screen area 66a includes an arrow, which is oriented to indicate whether the touch screen area increases or decreases the angular orientations of the respective deck section or the height of the patient support surface. Additional touch screen areas 66f may be provided that generate signals to the controller to configure the patient support surface into a pre-selected configuration, such as the Trendelenburg or reverse-Trendelenburg positions. Further, touch screen image 66 includes a window 66g with an icon that graphically represents the Trendelenburg and reverse-Trendelenburg positions and text 66h, which indicates the angle of the patient support surface. Further, touch screen image 66 may include another text window 66i to display the HOB angle. Again, after a pre-selected period of time has elapsed with no selections being made, the controller may revert to displaying another screen, such as a default screen, or may simply leave screen 66 on the display until another function is selected by user interface 36.

Lockouts

When user interface device 36d is selected, a lockouts screen image 68 will be generated by the controller. Screen image 68 may assume a number of different configurations, as shown in FIGS. 31A-31D, depending on the selection made by the user. Referring to FIG. 31A, screen image 68 includes an icon 68a, which schematically represents the three sections of the deck support of the patient support surface. A second icon 68b is provided, which schematically represents the elevation mechanism for the bed. Further, screen image 68 includes user interfaces 68c and 68d, which may be used to select whether the lockouts, to be described below, apply to all the bed controls as indicated in user interface 68d or simply to the patient controls only (68c). When the patient controls only user interface is selected (66c), the individual actuators on the bed may be blocked from use by the patient as illustrated in FIGS. 31A and 31B. For example, in the illustrated embodiment, the icon 68g associated with the bed elevation actuator indicates that the bed elevation actuator is not an actuator that can be adjusted by the patient, similar to the actuator associated with the leg section of the deck, represented by icon 68h. Further, screen image 68 includes a user interface 68e, which when selected by the user unlocks all the "unblocked" actuators as shown in FIG. 31A or locks all the "unblocked" actuators as shown in FIG. 31B. For example, as shown in FIGS. 31A and 31B, each representative deck section in the icon 68a includes an icon 68f, which indicates whether the actuator associated with that particular deck section is locked (FIG. 31B) or unlocked (FIG. 31A). Further, only those actuators not blocked are controlled by the selection of user interface 68e.

Referring to FIGS. 31C and 31D, when the all bed controls user interface 68d is selected, selection of user interface 68e will control each of the actuators on the bed. As shown in FIG. 31C, when user interface 68e is selected such that it displays the unlocked icon, each of the respective user interfaces 68f, 68g, and 68h will indicate an unlocked condition for their respective actuators. In contrast, referring to FIG. 31D, when lockout user interface 68e is selected to display a locked condition, each of the respective user interfaces 68f, 68g, and 68h will indicate a locked condition for their respective actuators.

The controller will then return the display to the main menu display 38 after a period of time, as measured by the controller.

Event Manager

Figure 32:
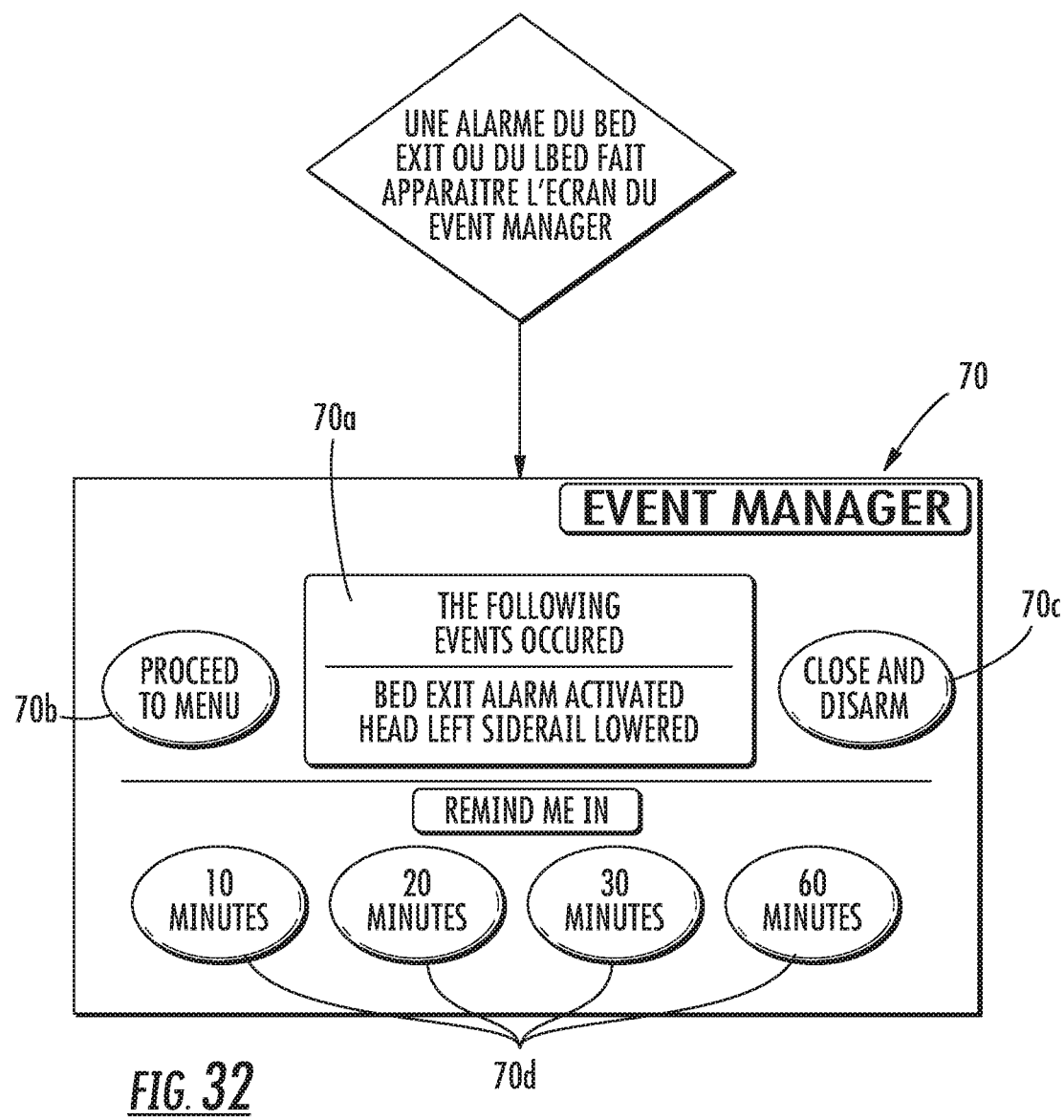
FIG. 32 illustrates a screen image provided by the controller at the display.

In addition to displaying screen images in response to input by users at user interfaces, display 38 may display bed conditions. In the illustrated embodiment, an event manager screen image 70 is displayed in response to triggers from a condition at apparatus 10. For example, referring to FIG. 32, screen image 70 is displayed when an event occurs, such as the bed exit alarm is activated or when a side rail is lowered, including for example the head left or right side rail being lowered. Other alarm conditions that may be included for example, include when the patient support surface is wet, when the patient has not moved over a selected period of time, or for example when the patient has moved excessively over a predetermined period of time, with each of these alarm conditions occurrences being preprogrammed into the controller.

In the illustrated embodiment, screen image 70 includes a text window 70a, which identifies the event that has occurred. For example, in the illustrated embodiment, the bed exit alarm was activated and head left side rail was lowered, which triggered the controller to generate screen image 70. Although the events are illustrated as being conveyed in a text message format, it should be understood that other message formats or prompts can be used, such as icons or audible messages using the speakers on the bed, for example.

In addition screen image 70 includes a user interface 70b to allow a user to proceed to a menu of the events that can be monitored and generate notifications. Additionally, screen image 70 includes a second user interface 70c, which allows the user to close and disarm the event or alarm setting. Further, screen image 70 includes a plurality of additional user interfaces 70d, which allow the user to input a reminder request to the controller and, further, specify the time period for the reminder or prompt. For example, each user interface 70d may include a time associated therewith, which may be indicated by text or by graphical images or a combination of both. After the close and disarm user interface has been selected or after a reminder period has been selected, the controller will return the display to the initial screen image at touch screen 38a.

Scale Functions

Figure 33:
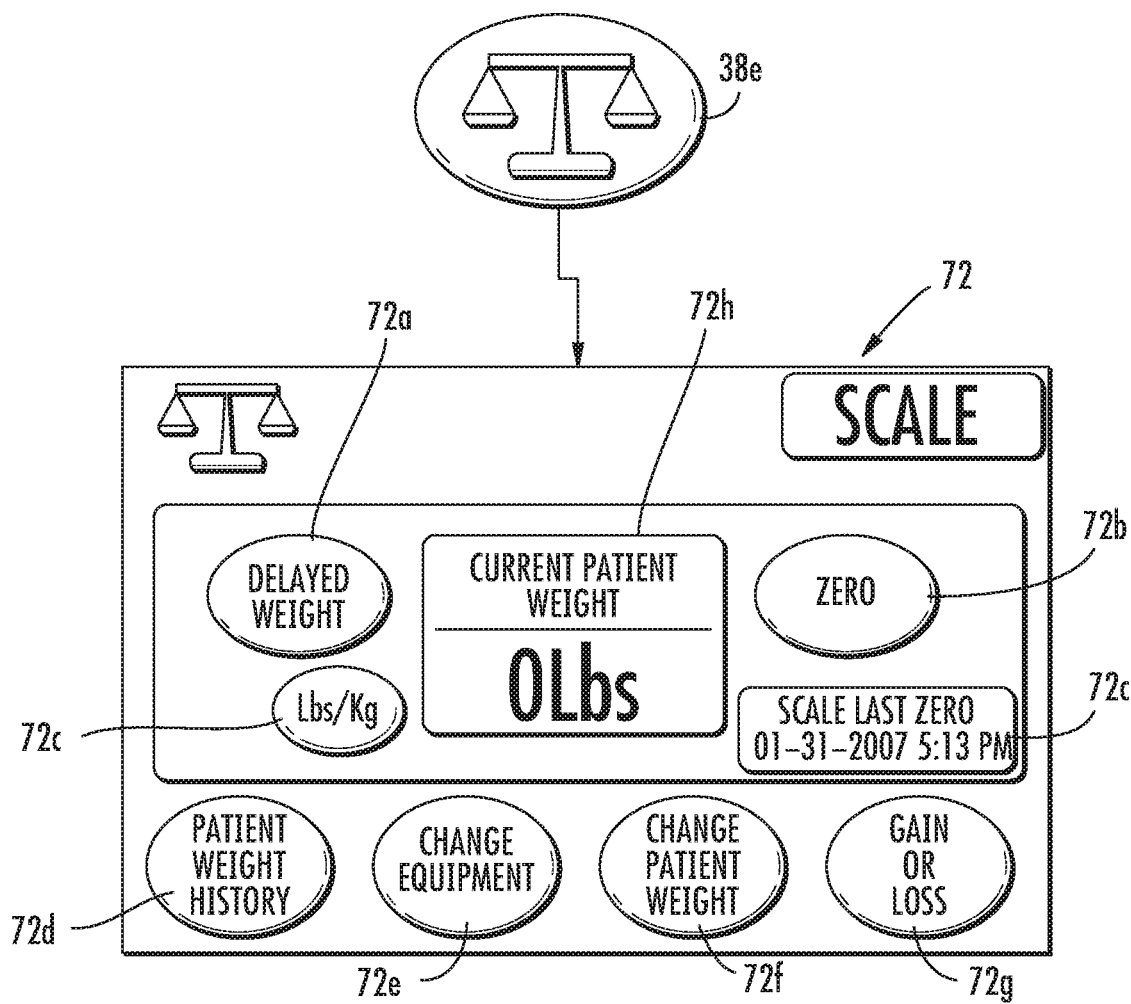
FIG. 33 illustrates a screen image provided by the controller at the display.

When user interface 36e is selected, a scale screen image 72 will be generated and displayed, such as illustrated in FIGS. 28 and 33. As will be more fully described below, when user interface 36e is selected, the controller will provide a plurality of overlay screen images with user interfaces to guide a user through the patient weighing process. Referring to FIG. 33, the initial display 72, which is displayed when user interface 38e is selected, includes a plurality of user interfaces 72a, 72b, 72c, 72d, 72e, 72f, and 72g. Further, display 72 includes a text window 72h, which displays the current patient weight in the scale selected by user interface 72c, which is used to select between pounds and kilograms. Further, an additional text display 72i may be provided that includes text relating to the date and time that the scale was last zeroed.

Figure 34:
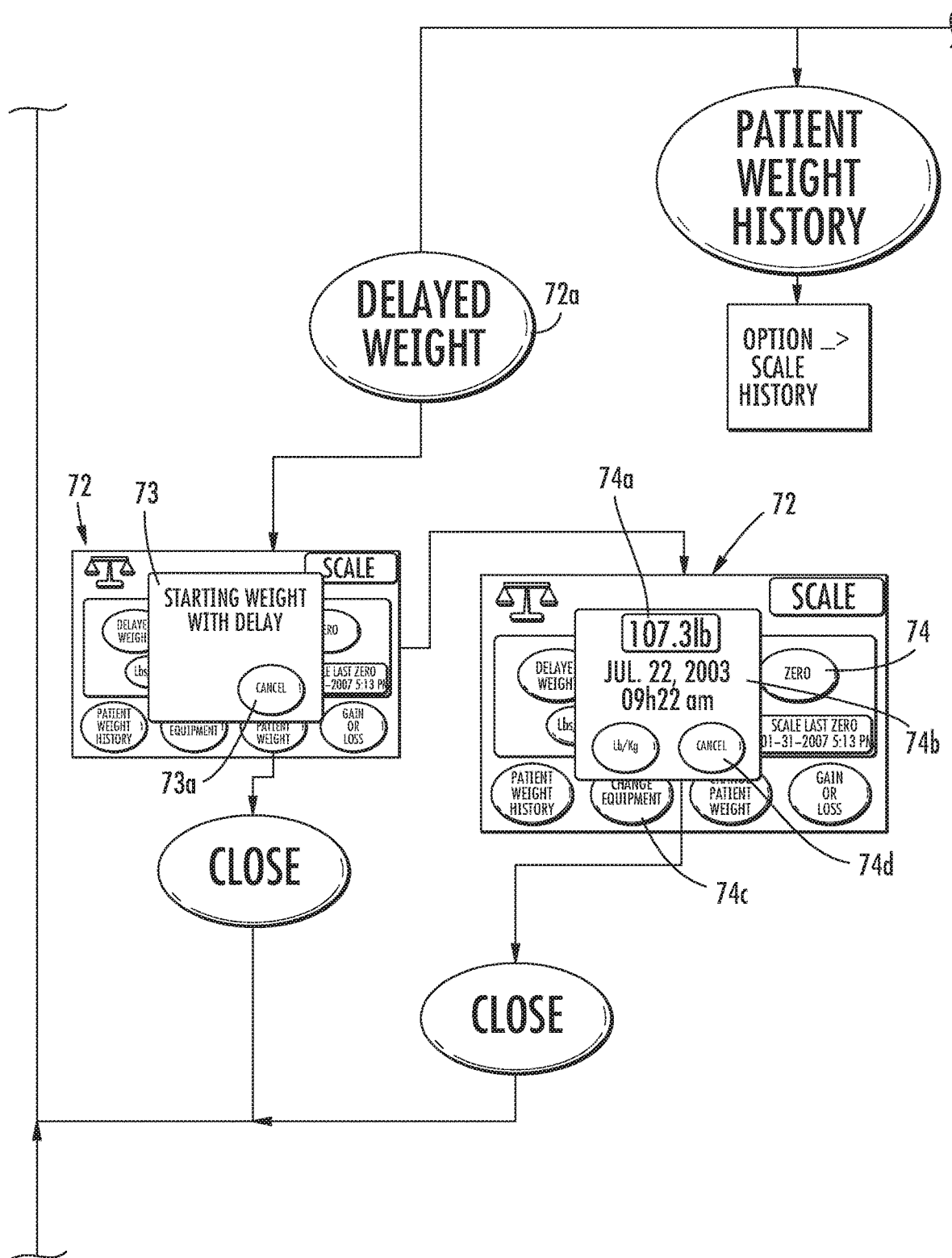
FIG. 34 illustrates a screen image provided by the controller at the display.

When the patient is to be weighed, the user will select user interface 72a. Referring to FIG. 34, when user interface 72a is selected, the controller will generate an overlay display 73, which acknowledges the selection and, further, includes text letting the user know that the bed will weigh the patient after a delay. Display 73 further includes a user interface 73a, which allows the user to cancel the weighing sequence. After a timed delay, which is stored in the controller, display 72 will generate second overlay display 74, which includes a text window 74a for displaying the weight of the patient and, further, optionally displays text 74b indicating the time and date of when the patient's weight was taken. Further, display 74 includes a user interface 74c to allow the user to select between pounds and kilograms. Similarly, a user interface 74d is provided that allows the user to close the screen image 74 and return to the main scale screen image 72.

Figure 35:
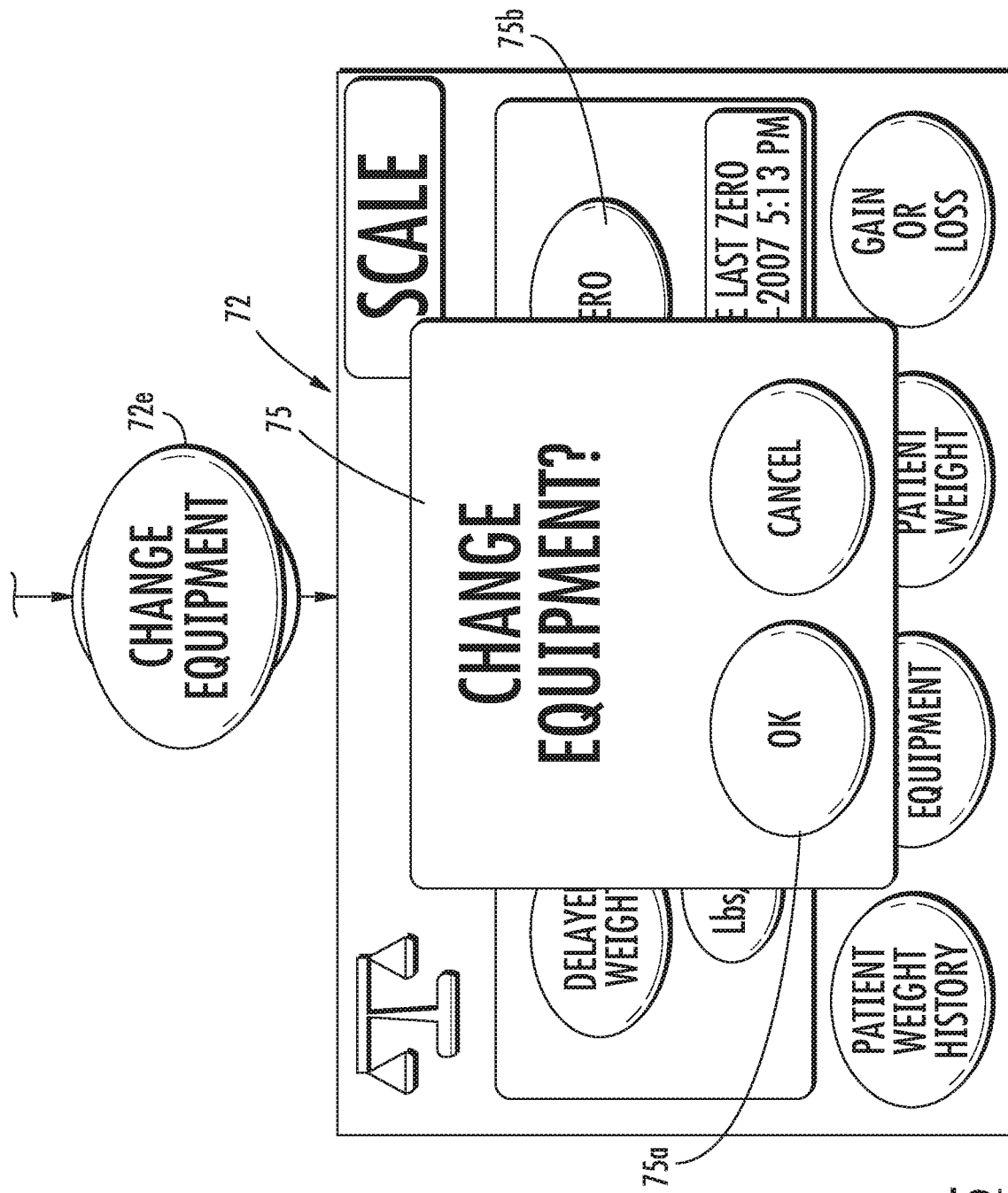
FIG. 35 illustrates a screen image provided by the controller at the display.

As described in the referenced applications, the controller calibrates the weight of the patient based on equipment mounted to the bed. Therefore, should additional equipment be added or removed, in order to get an accurate reading on the patient's weight, the change of equipment must be taken into account. Therefore, when changing equipment, whether adding or removing equipment, the user can select user interface 72e to indicate that equipment is being changed on the bed. When user interface 72e is selected, another overlay screen image 75 (FIG. 35) will be generated by the controller, which prompts the user to acknowledge that a change of equipment is going to occur by selecting user interface 75a. If no change of equipment is going to occur or the selection was made in error, the user may select user interface 75b to cancel the procedure.

Figure 36:
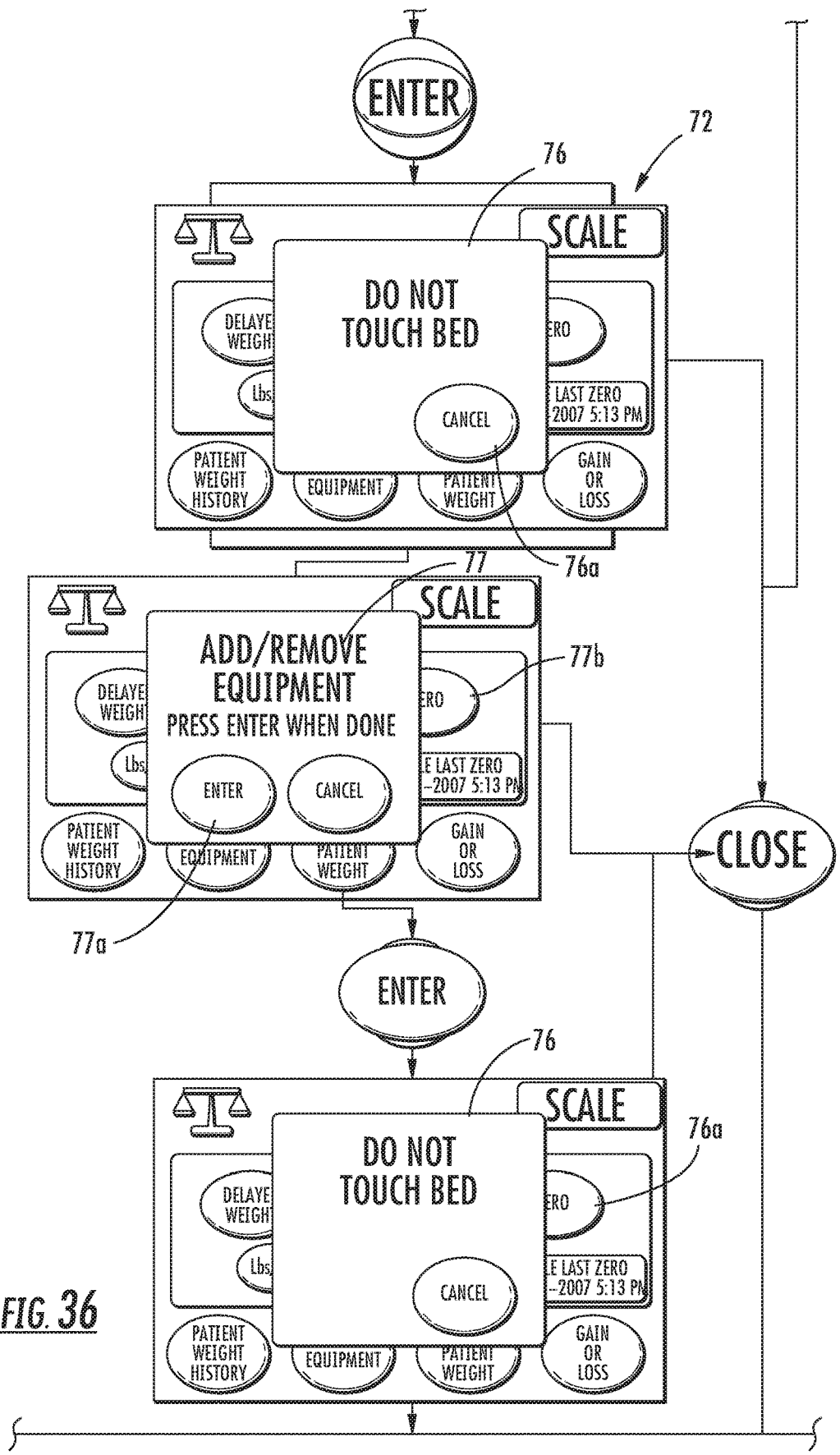
FIG. 36 illustrates a screen image provided by the controller at the display.

In response to user interface 75a being selected, the controller generates another overlay screen image 76 (FIG. 36), which instructs the user not to touch the bed so that the weight of the bed prior to adding equipment can be precisely determined. Overlay screen image 76 may include a user interface 76a to allow the user to cancel the process and return the screen image to the main scale screen image 72 (FIG. 33). After a preselected predetermined time, which is stored in the controller, the controller will then generate yet another screen image 77 with instructions to the user to add or remove the equipment and, further, to select user interface 77a when the equipment change is complete. Optionally, screen image 77 includes another user interface 77b to once again allow the user to cancel the process and return to screen image 72.

After the user interface 77a is selected, which indicates to the controller that the equipment has been removed or added, the controller will again generate overlay screen image 76, which warns the user not to touch the bed, so that the computer will have time to measure the change in weight at the bed. Again, screen image 76 includes a user interface device 76a that will allow a user to cancel the process.

Figure 37:
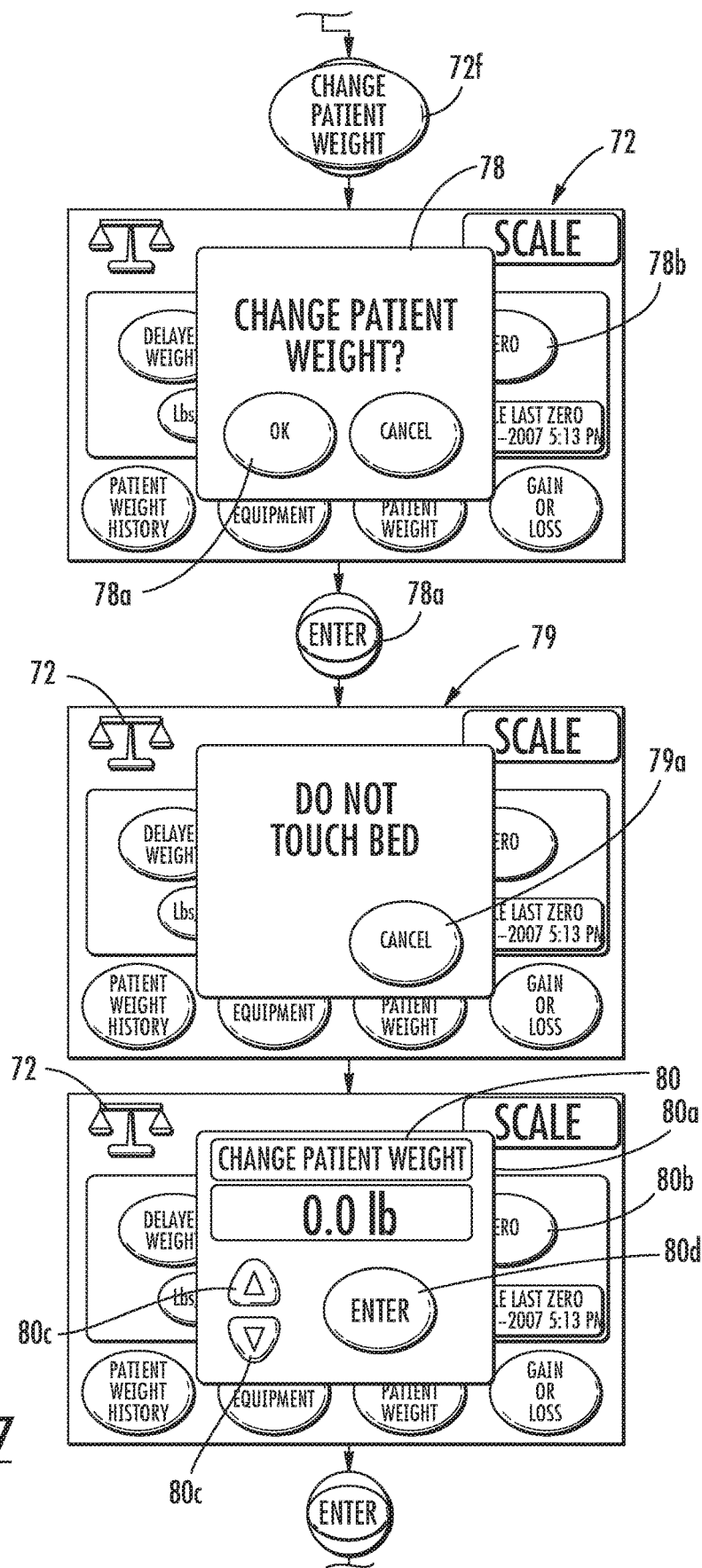
FIG. 37 illustrates a screen image provided by the controller at the display.

Referring again to FIG. 37, after any necessary equipment change adjustment has been complete, and display 38 returns to screen image 72, a user may select the change patient weight user interface 72f to allow the user to change the patient's weight. When user interface 72f is selected, the controller will generate an overlay screen image 78, which requests whether the user wishes to change the patient's weight and includes a user interface 78a that, when selected, confirms that the patient weight is to be changed and a second user interface 78b so that the user may cancel the process. When user interface 78a is selected, the controller will generate another overlay screen image 79, which instructs the user not to touch the bed and, further, optionally includes a user interface 79a to allow the user to cancel the process.

After a predetermined time stored within the controller, the controller will generate another screen image overlay 80, which includes a text window 80a to confirm that the patient weight is being changed and a second text window 80b, which displays a combination of alphanumeric text to indicate the patient's weight. Further, screen image 80 includes user interfaces 80c, which allow the user to increase or decrease the weight of the patient. Once the weight is adjusted using user interfaces 80c, the user may enter the patient's weight into the controller using user interface 80d. Once entered, the controller will remove the overlay image 80 to allow the user to view the full screen of screen image 72.

Figure 38:
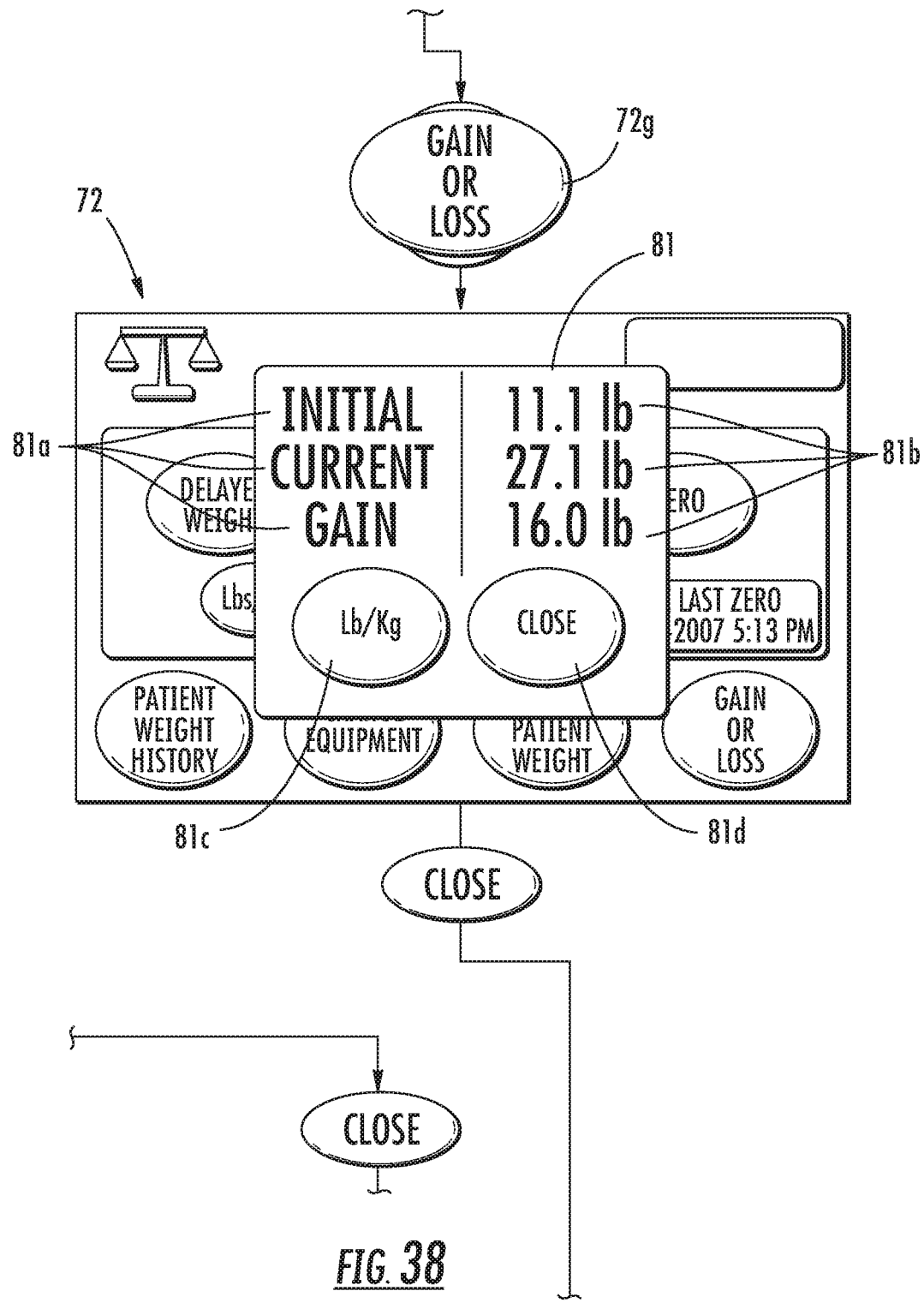
FIG. 38 illustrates a screen image provided by the controller at the display.

Referring again to FIG. 33, should the user select user interface 72g, the controller will generate yet another overlay screen image 81 (FIG. 38), which includes text 81a and text windows 81b to identify what the initial weight of the patient is, the current weight of the patient, and the change in weight (gain). Further, screen image 81 includes an interface 81c that allows the user to select between pounds and kilograms. Further, screen image 81 includes a user interface 81d to allow the user to close the screen image and return to the main scale screen image 72.

Figure 39:
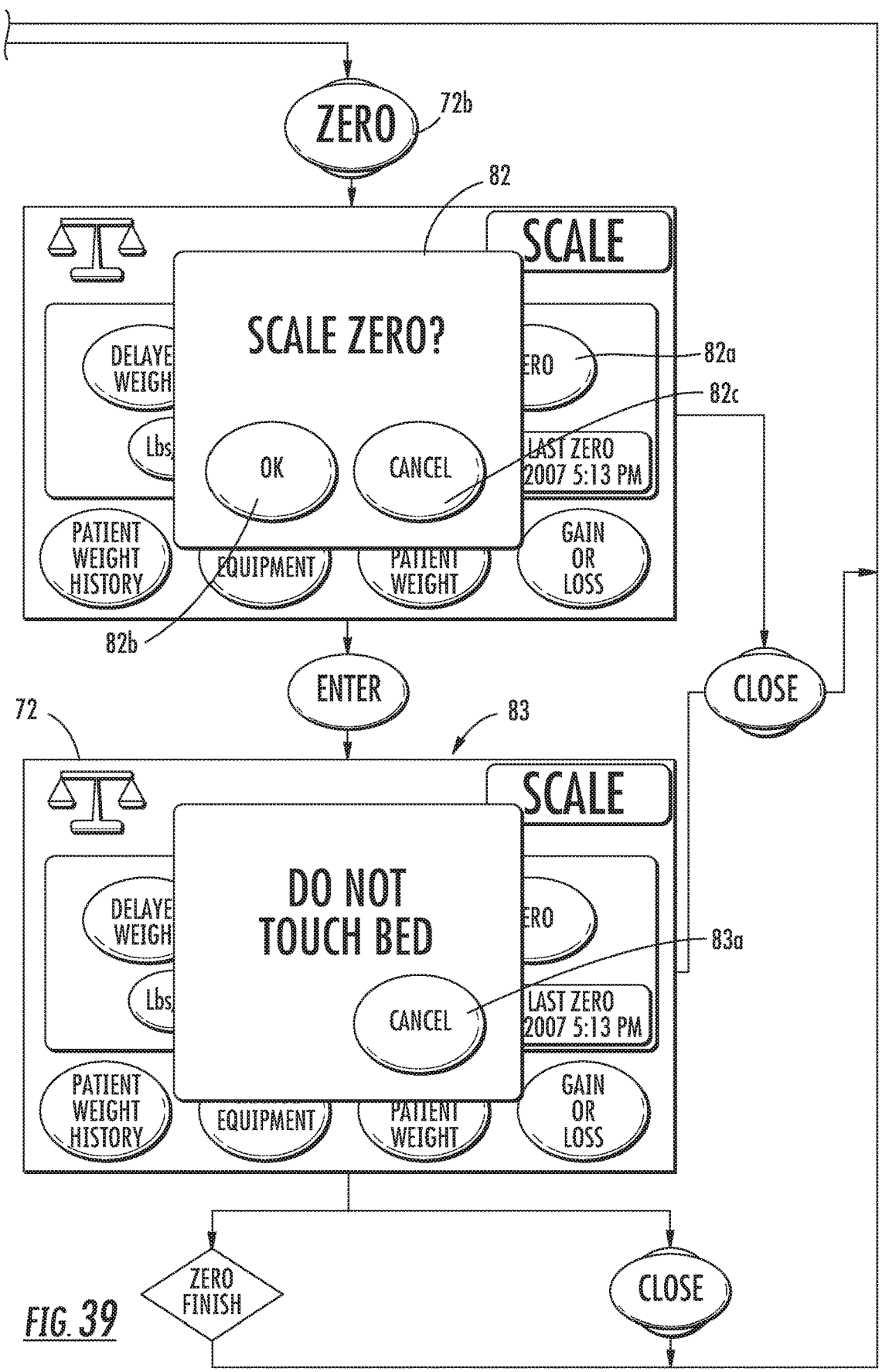
FIG. 39 illustrates a screen image provided by the controller at the display.

A further function provided by screen image 72 is to allow a user to set the scale to zero, for example, when a patient has exited the bed. When a user selects user interface 72b, control system will generate an overlay screen image 82 (FIG. 39), which displays a text message 82a, which requests the user to confirm whether the scale should be set to zero and, further, includes a user interface 82b to allow the user to affirm the selection. Additionally, a user interface 82c is provided to allow the user to cancel the process.

Once the user selects user interface 82b, the controller will generate an overlay screen image 83 instructing the user not to touch the bed, which further includes a user interface 83a to allow the user to cancel the process. Once the controller has set the scale to zero, the control system will remove the overlay screen image 83 to return the display to screen image 72.

Bed Exit

As noted above, patient support apparatus 10 may incorporate a bed exit system. Bed exit system may be used to provide information regarding the patient's location on the patient support surface. Further, the position of the patient can be graphically displayed on display 38 or at a remote monitoring station, for example, wherein the position can be displayed in a color-coded position or pressure diagram. Based on the patient's bed position, the controller may be configured to determine the likelihood of a patient exiting the bed and initiating an appropriate alarm if bed exiting has occurred or is likely to occur. Further, based on the evaluation of the patient's position, movement of the patient can be evaluated, thereby providing a means for issuing an alarm due to patient inactivity or activity, for example when an ICU patient is awakening.

As described in the referenced application, the bed exit system uses a load cell system that is incorporated into patient support 10. For the bed exit system, the load cell system is typically mounted below the deck sections (22a, 22b, and 22c) and on the load frame 23 that mounts the deck to the base. Signals from the load cells 27 are monitored and processed by, for example, controller 25 and, as noted above, may be used to measure the patient's weight and, further, to determine the weight on the individual load cell, which may correspond, for example to the foot left or right left load cell or head left or head right load cells. An example of a suitable bed exit system is described in U.S. Pat. No. 5,276,432, commonly owned by Stryker Corporation, which is incorporated herein by reference in its entirety.

Figure 41:
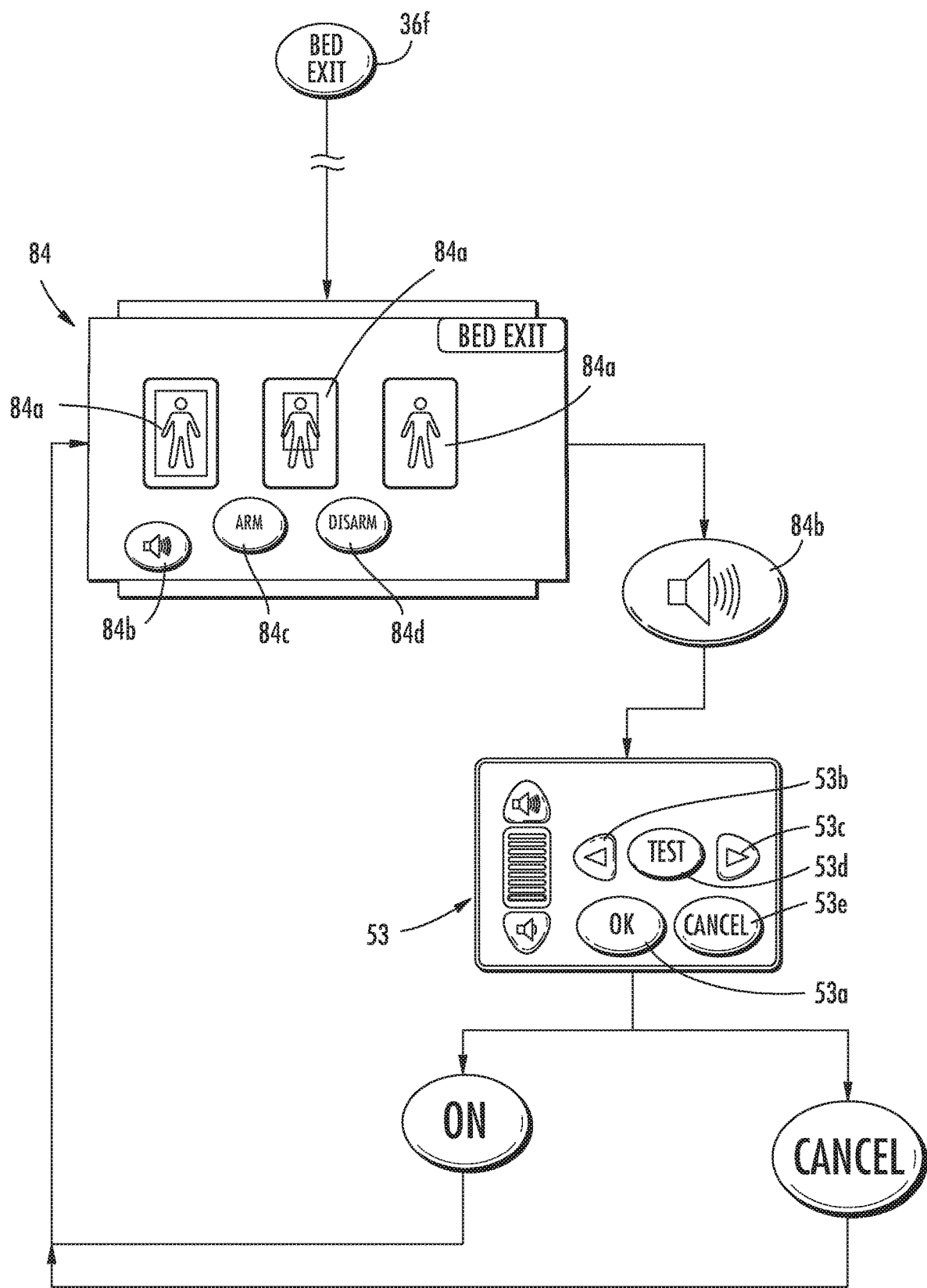
FIG. 41 illustrates a screen image provided by the controller at the display.

When bed exit user interface 36f (FIG. 41) is selected, the controller will generate a screen image 84 that includes a plurality of icons 84a that represent whether the bed exit system is armed or disarmed. Further, screen image 84 includes user interfaces 84b, 84c, and 84d to allow a user to select the alarm, to arm the bed exit system, or disarm the bed exit system. When the alarm user interface 84b is selected, screen image 53 (described previously) will be generated by the controller, which allows the user to set the alarm, adjust the volume of the alarm, and test the alarm.

Other Options

Figure 42:
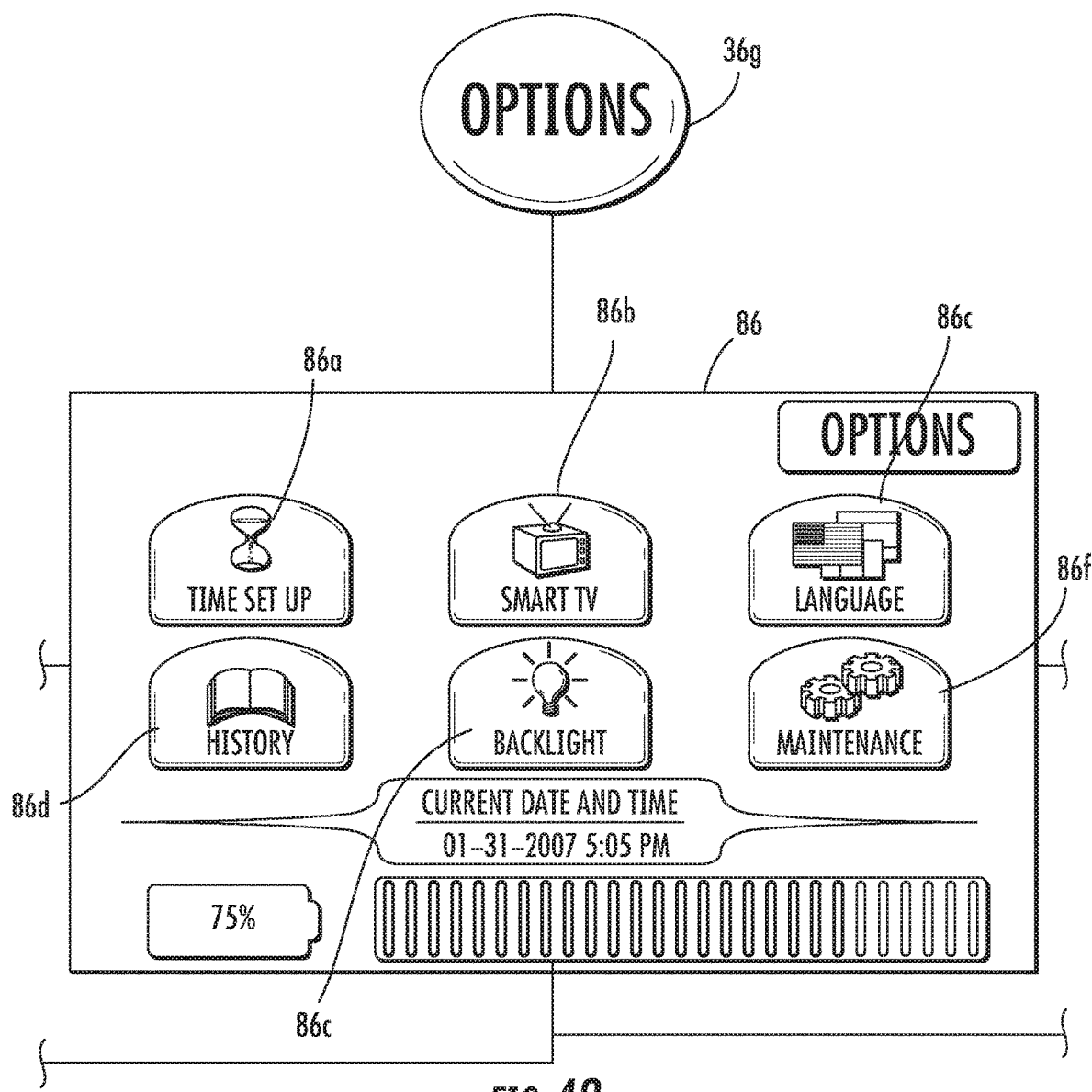
FIG. 42 illustrates a screen image provided by the controller at the display.

Referring again to FIG. 2, control assembly 30 includes a user interface 36g, which allows a user to select a plurality of bed related features or functions. Referring to FIG. 42, when user interface 36g is selected, the controller will generate an options screen image 86, which includes a menu of options. To select from the menu of options, screen image 86 includes a plurality of user interfaces 86a, 86b, 86c, 86d, 86e, and 86f. It should be understood that additional options may be provided and, further, associated with a respective user interface provided at screen image 86. In the illustrated embodiment, user interface 86a is associated with setting the time on the controller. User interface 86b allows a user to select a configuration of the TV. User interface 86c allows a user to select a language for the controller so that text is displayed in the selected language. User interface 86d allows the user to view historical data that may be stored in the controller. User interface 86e allows a user to adjust the brightness of a backlight provided at the patient support, and user interface 86f allows a user to initiate a maintenance check on the patient support.

Figure 43:
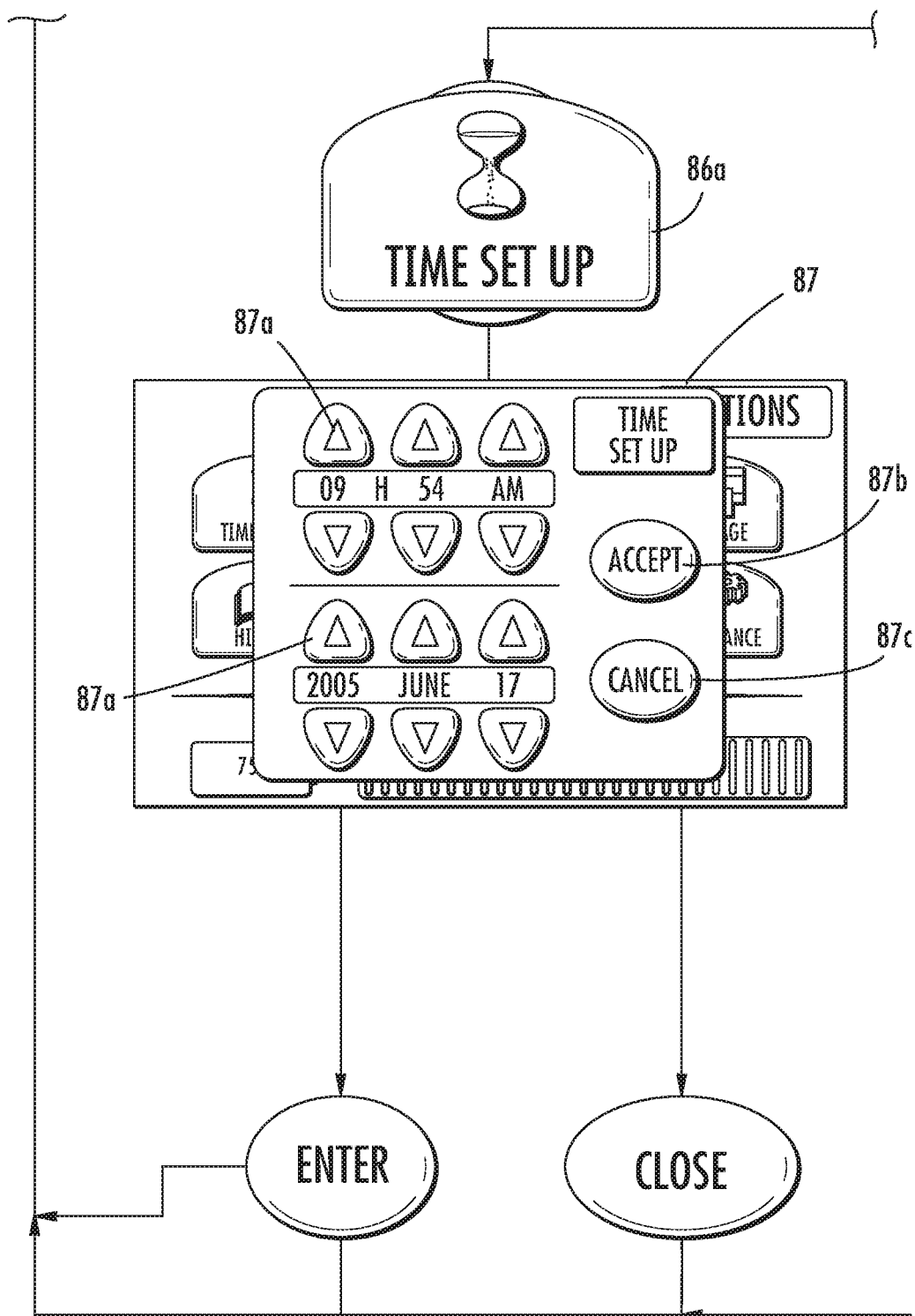
FIG. 43 illustrates a screen image provided by the controller at the display.

Referring to FIG. 43, when user interface 86a is selected, the controller will generate an overlay screen image 87, which includes a plurality of user interfaces 87a to allow the user to select the time and date. Further, screen image 87 includes a user interface 87b to enter the selected time and a second user interface 87c, which allows the user to cancel the time setup. After the new time is entered into the controller or the time setup process is cancelled, the controller will close screen image 87 to display screen image 86.

Figure 44:
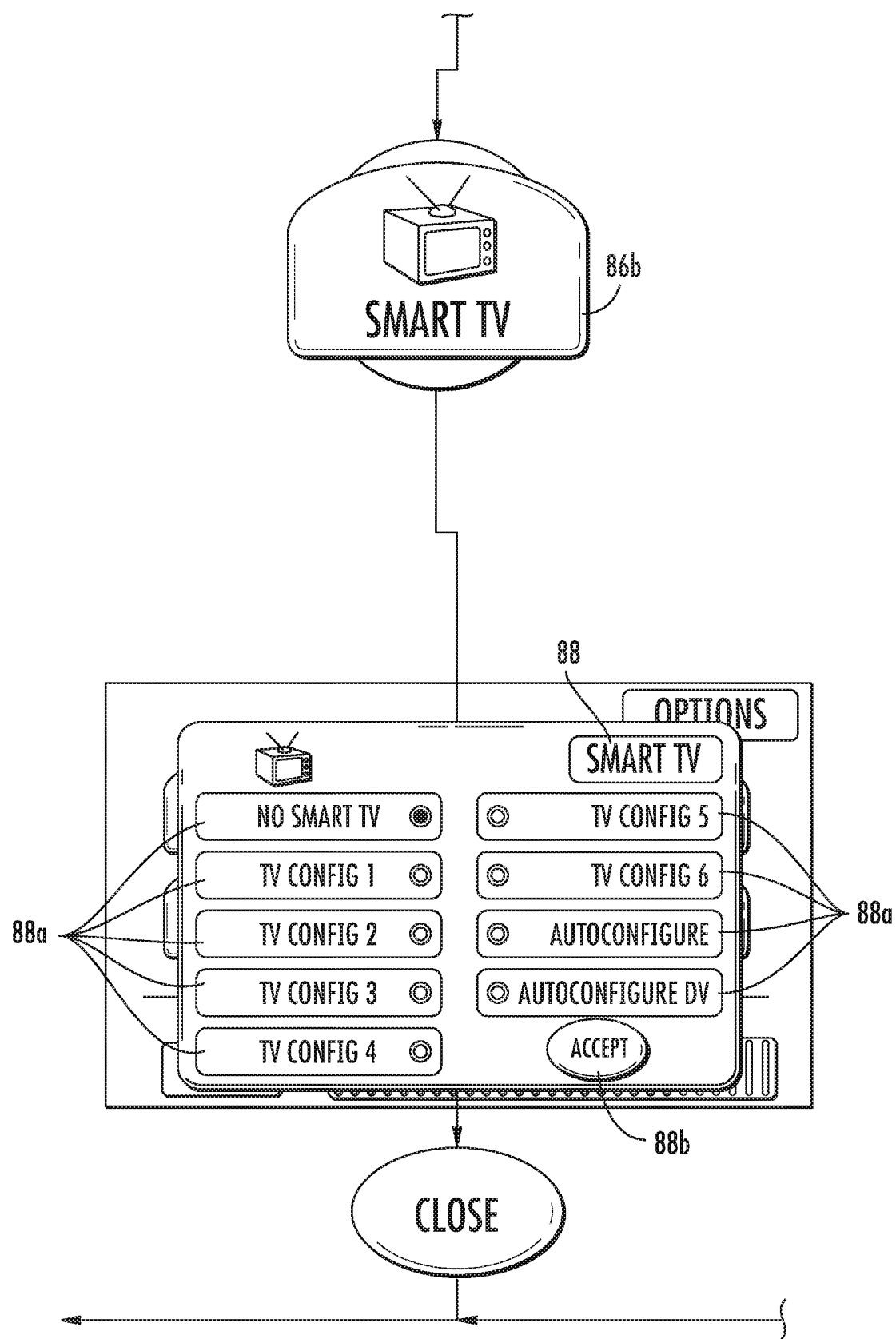
FIG. 44 illustrates a screen image provided by the controller at the display.

Referring to display screen image 86, if the user wishes to change the configuration of the TV, the user may select user interface 86b, which triggers the controller to generate an overlay screen image 88 (FIG. 44) with various TV options. For each option, screen image 88 includes a user interface 88a that allows the user to choose between the various configurations for the TV, including an auto configuration, which is stored in the computer system. Further, touch screen image 88 includes a user interface 88b to allow the user to enter and store the selected configuration in the controller. Once the configuration is entered into the controller, the controller will remove the overlay display to return to the options display 86.

Figure 45:
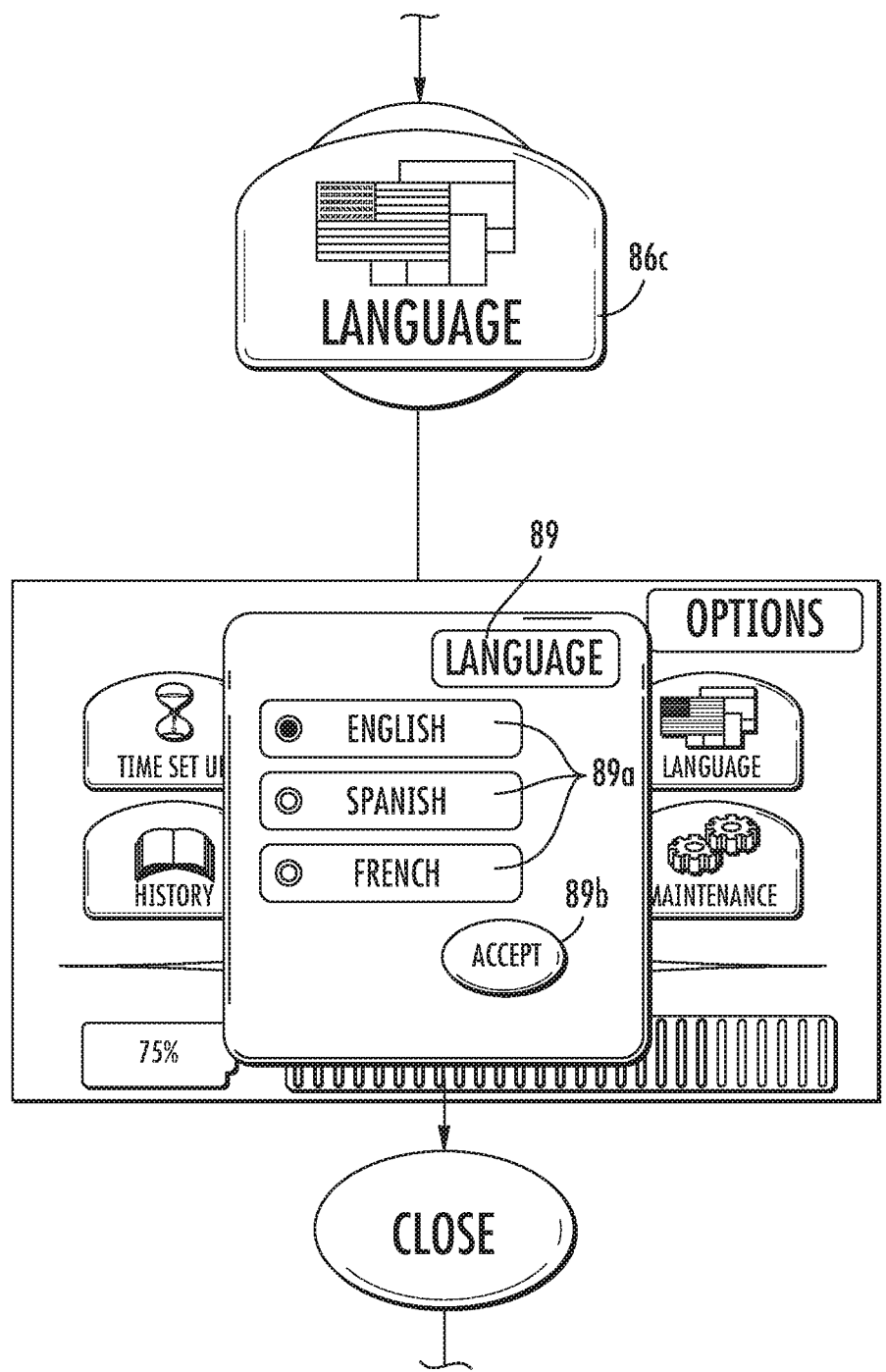
FIG. 45 illustrates a screen image provided by the controller at the display.
Figure 46:
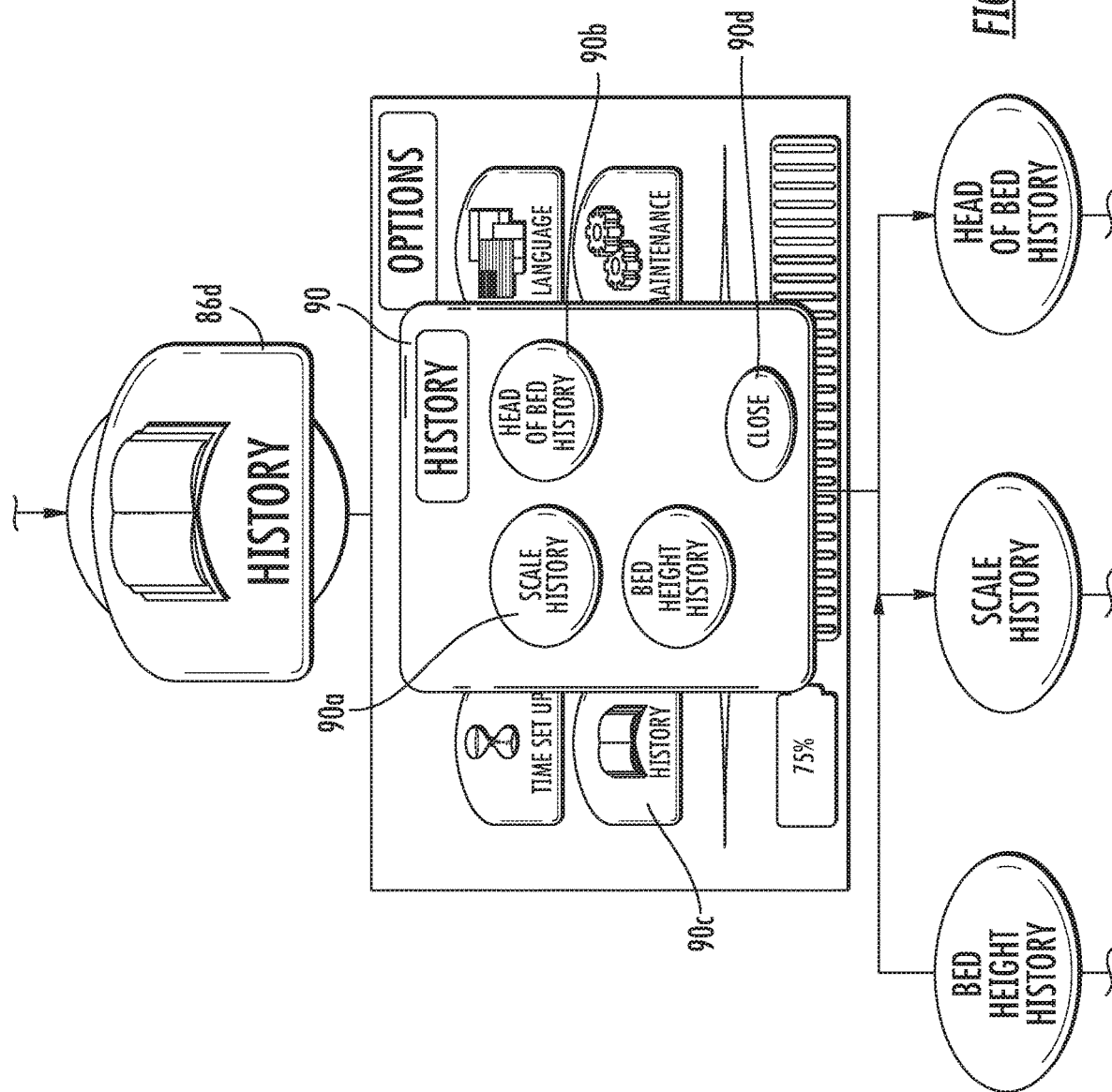
FIG. 46 illustrates a screen image provided by the controller at the display.

As noted above, screen image 86 includes a user interface 86c to select the language of the text displayed at control module or other displays on the bed. As best seen in FIG. 45, when user interface 86c is selected, the controller will generate a language overlay display image 89, which includes a plurality of user interfaces 89a for selecting between language choices, such as English, Spanish, and French. Once the language is selected using user interfaces 89a, the user can enter the selection using user interface 89b. Once the selection is made, the controller will close screen image 89 to return to screen image 86. It should be understood that the number of language options may be increased and/or changed.

Referring again to FIG. 42, when a user selects user interface 86d, the controller will generate a history overlay screen image 90, which allows the user to view various histories, including the scale history, which is actuated by user interface 90a, the head of bed history, which is selected by actuating user interface 90b, bed height history, which is selected by actuating user interface 90c. Furthermore, screen image 90 includes a user interface 90d to allow the user to close the screen image and terminate the process.

Figure 47:
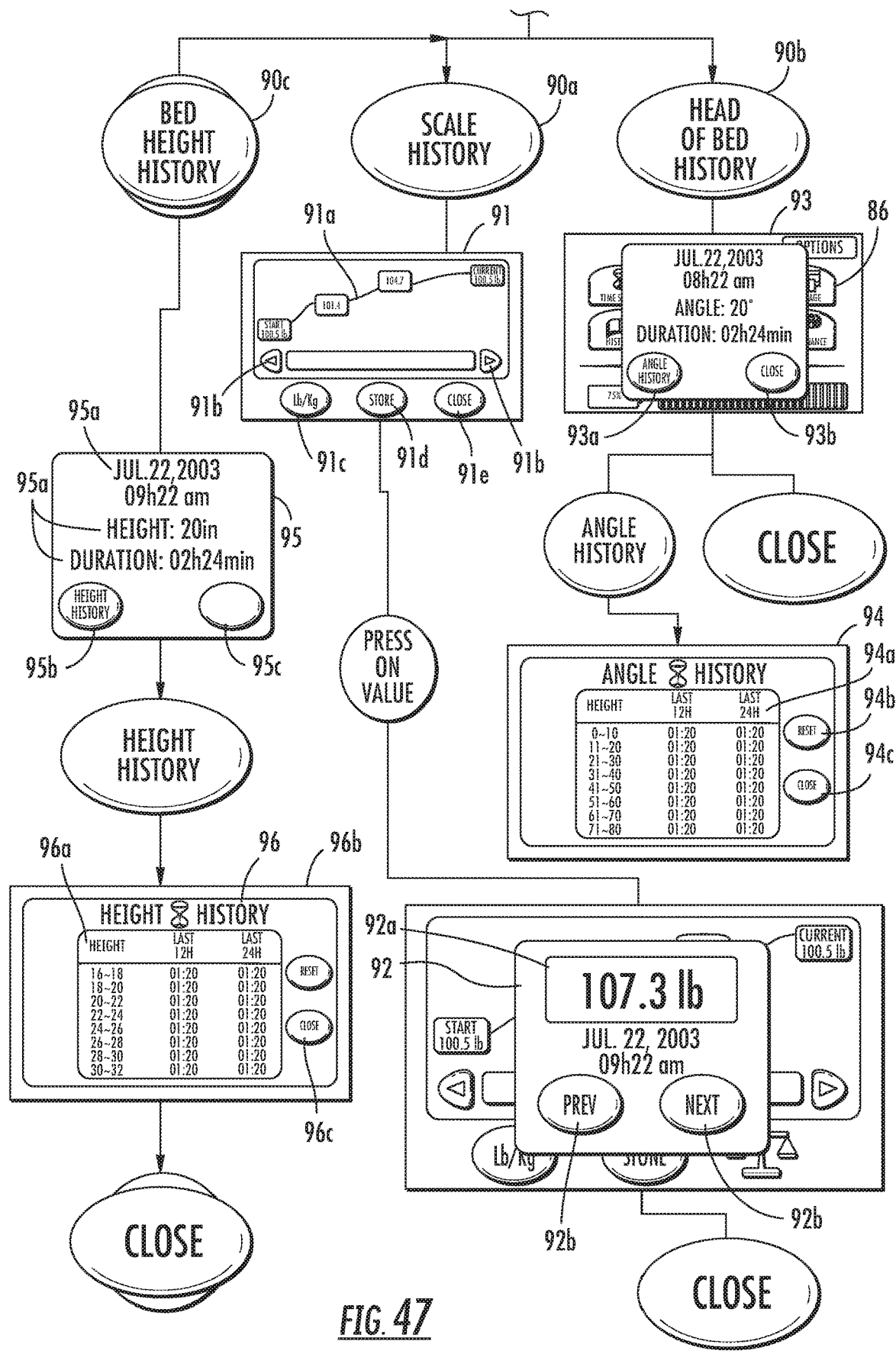
FIG. 47 illustrates a screen image provided by the controller at the display.

Referring to FIG. 47, when a user selects user interface 90a, the controller will generate a scale history screen image 91, which includes a graphical representation 91a of the patient's weight starting from the starting weight of the patient to the current weight of the patient. Further, screen image 91 includes user interfaces 91b to allow a user to select between the various data points to check the weight of the entire history of the patient. Further, screen image 91 optionally includes a user interface 91c for converting the scale from, for example, pounds to kilograms. In addition, screen image 91 optionally includes a user interface 91d, which when selected initiates the controller to store a selected weight using user interface 91b. Further, as in the case of any of the screen images, screen image 91 may incorporate a user interface to close the screen image to terminate the function.

When user interface 91d is selected, the controller will generate an overlay screen image 92, which includes a window 92a for displaying the weight selected using user interfaces 91b. Further, screen image 92 will include a text area that displays the date and time of the weight associated with window 92a. Also, overlay screen image 92 includes a pair of user interfaces 92b to allow the user to look at the previous or next weight entries that stored in the controller.

Similarly, when a user selects user interface 90b, the controller will generate an overlay screen image 93 that will allow a user to check the angle history of the head of the bed. For example, overlay screen image 93 includes a user interface 93a, which when selected causes the controller to generate another screen image 94, which includes a display area 94a that lists in the illustrated embodiment in tabular form the angle history of the head of the bed. For example, display 94 can include the various angle ranges the last time that the head of the bed fell within that angle range within the last twelve hours and, optionally, the last time the head of the bed fell in those specific angular ranges in the last twenty-four hours. Further, screen image 94 includes a user interface 94b that allows a user to indicate to the controller to reset the angle data. Touch screen image 94 also includes an additional user interface 94c, which allows the user to close the screen image 94 to return to screen image 93.

Screen image 93 may additionally include date and time and the current angular position of the head with the bed including the duration of time in the form of a text display. Once image 93 is closed using user interface 93b, the control system will return the display to screen image 86.

When the user selects user interface 90c, the controller will be triggered to display the bed height history. For example, in the illustrated embodiment, the controller will generate a screen image 95 (FIG. 47) that displays information relating to the bed height. Specifically, in the illustrated embodiment, screen image 95 displays the bed height in alphanumeric text 95a, the duration of the bed at the height using alphanumeric text and, further, optionally the date and time that a user accesses the bed height history information. Further, screen image 95 includes a user interface 95b, which allows a user to view the history over an extended period of time. When user interface 95b is selected, the controller will generate another screen image 96 with a tabulation of the height history similar to screen image 94, which may include, for example, the ranges of height, the last time in the last twelve hours that the bed was in that range, and the last time the bed was in that range in the last twenty-four hour period.

Further, screen image 96 includes a user interface 96b that allows the user to reset the data in control system 25 and, further, a user interface 96c to allow the user to close screen image 96 to return to screen image 95. Similarly, screen image 95 includes a user interface 95c, which allows a user to signal to the controller to return to screen image 86.

Figure 48:
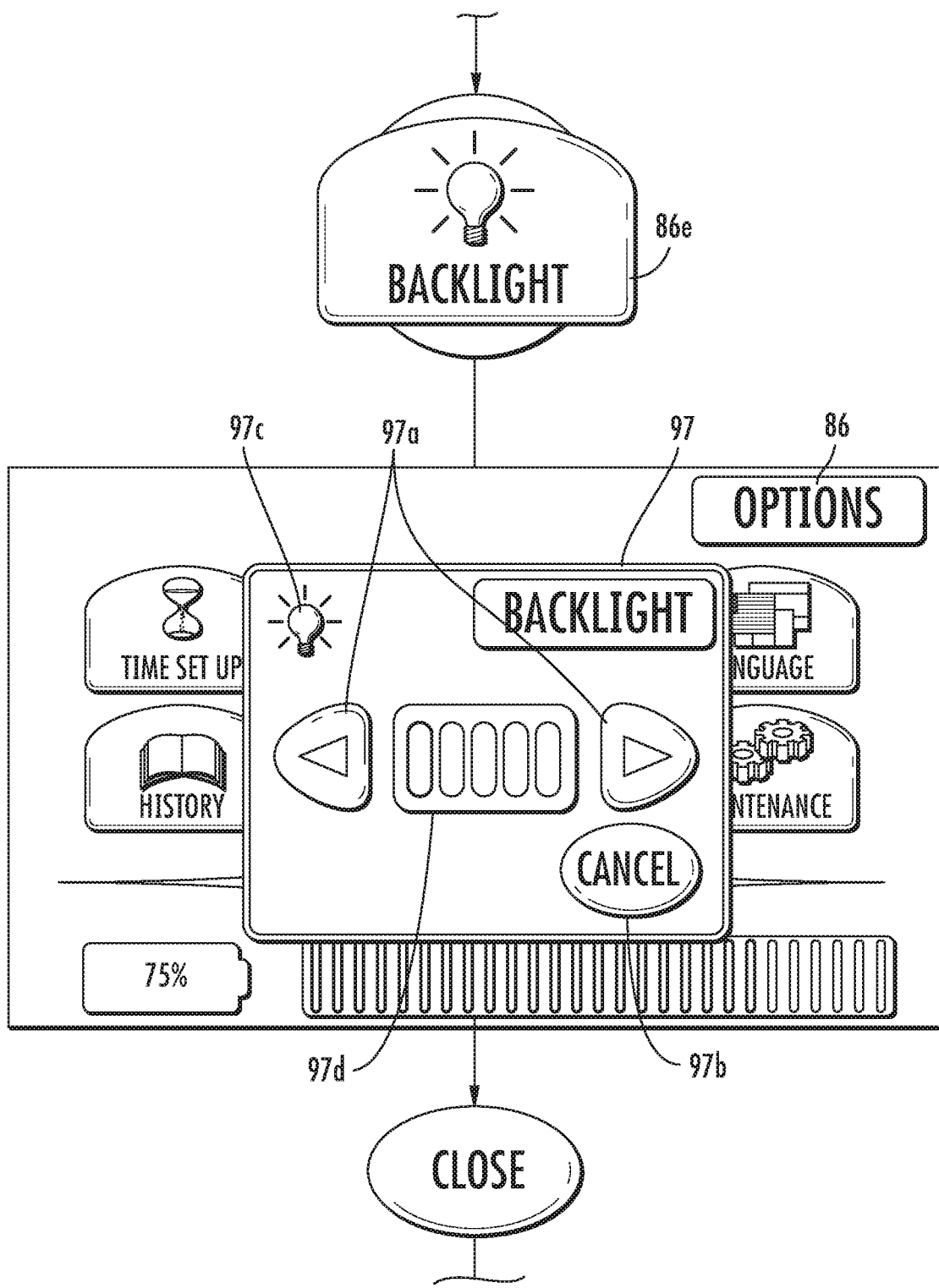
FIG. 48 illustrates a screen image provided by the controller at the display.

Referring again to FIG. 42, when a user selects user interface 86c, the controller will generate an overlay screen image 97 (FIG. 48), which includes a plurality of user interfaces 97a, which signal to the controller to adjust the intensity of the backlight on the bed and, further, the user interface 97b enter the selected light intensity. Optionally, screen image 97 includes icons 97c that represents the backlight itself and, further, an icon 97d that provides a graphical representation of the intensity of the light. Once the adjustment is made, and the user accepts the selected intensity by selecting user interface 97b, which signals to the controller to adjust the light accordingly. The controller will then return the screen image 97 to screen image 86 after a selected period of time as measured by the control system. Optionally, screen image 97 may include a further user interface (not shown) to close the screen image.

Figure 49:
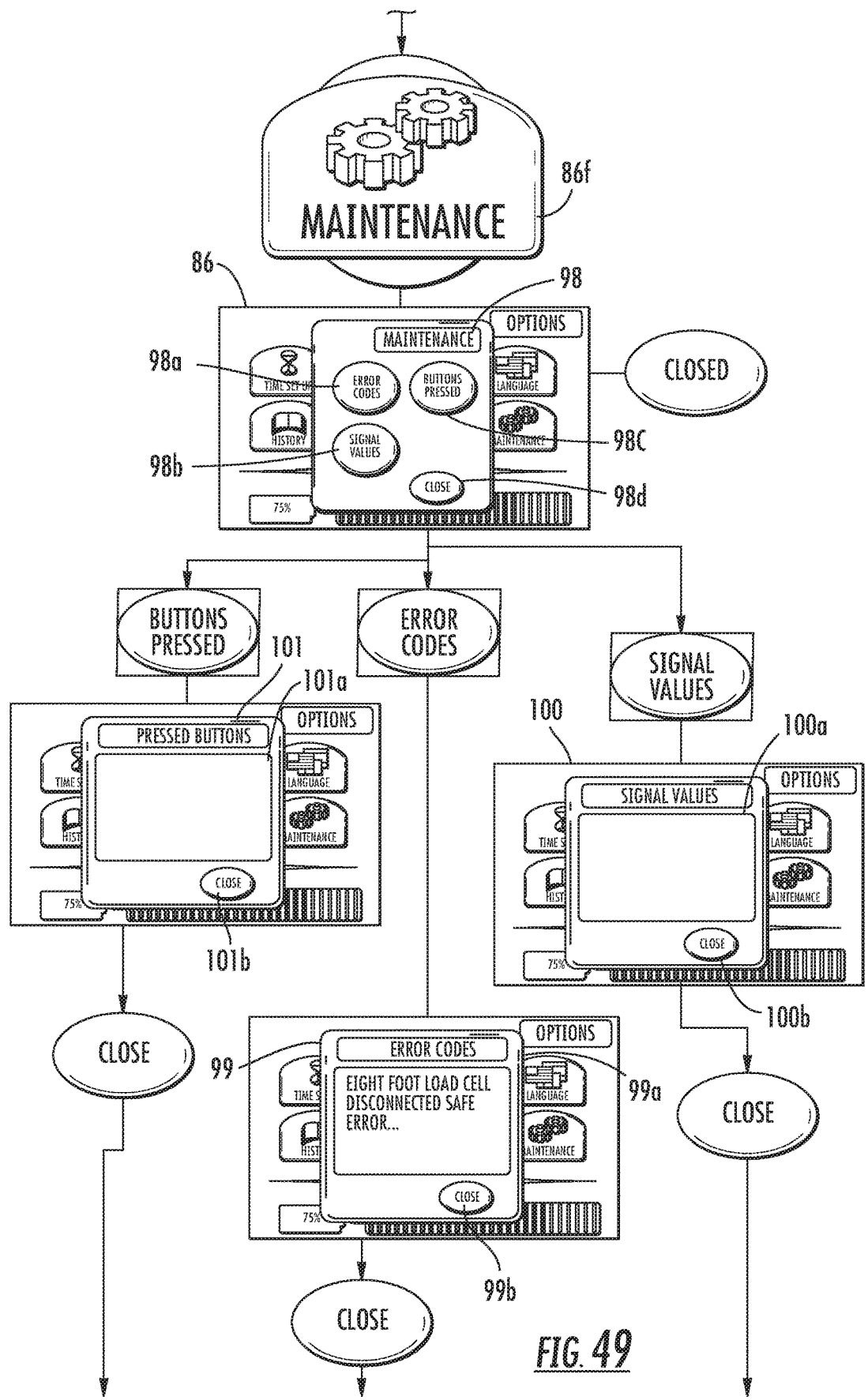
FIG. 49 illustrates a screen image provided by the controller at the display.

Referring again to FIG. 42, when the user selects user interface 86f, control system 25 will generate an overlay screen image 98 (FIG. 49), which allows a user to check the status of the maintenance of the bed. For example, in the illustrated embodiment, screen image 98 includes a plurality of user interfaces 98a, 98b, 98c, and 98d. User interface 98a allows the user to signal to the controller to display error codes, which are displayed on a second overlay screen image 99. Image 99 includes a text display 99a that will provide an indication of any error codes that may exist on the bed. Further, screen image 99 includes a user interface 99b that allows the user to close the screen image.

User interface 98b allows the user to signal to the controller to display the signal values. In the illustrated embodiment, the controller generates another overlay screen image 100, which includes, for example, a text box 100a that similarly lists the signal values. Further, screen image 100 includes a user interface 100b to allow the user to close the screen image.

When a user selects user interface 98c, user interface 98c signals to the controller 25 to list the buttons that have been pressed on the bed. In the illustrated embodiment, the controller generates yet another screen image 101 with a text area or display 101a where the identification information relating to the selected user interface may be displayed in alphanumeric text. Similarly, screen image 101 includes a user interface 101b that allows the user to close the screen image and turn to screen image 98. Once the user is completed with the maintenance check, the user can select user interface 98a to close the screen image and return to screen image 86.

Optionally, when user interfaces 36a, user interface 36c, and user interface 36g are selected at the same time, the controller may generate a screen (not shown) that allows the user to modify the configuration of the touch screen.

Figure 50:
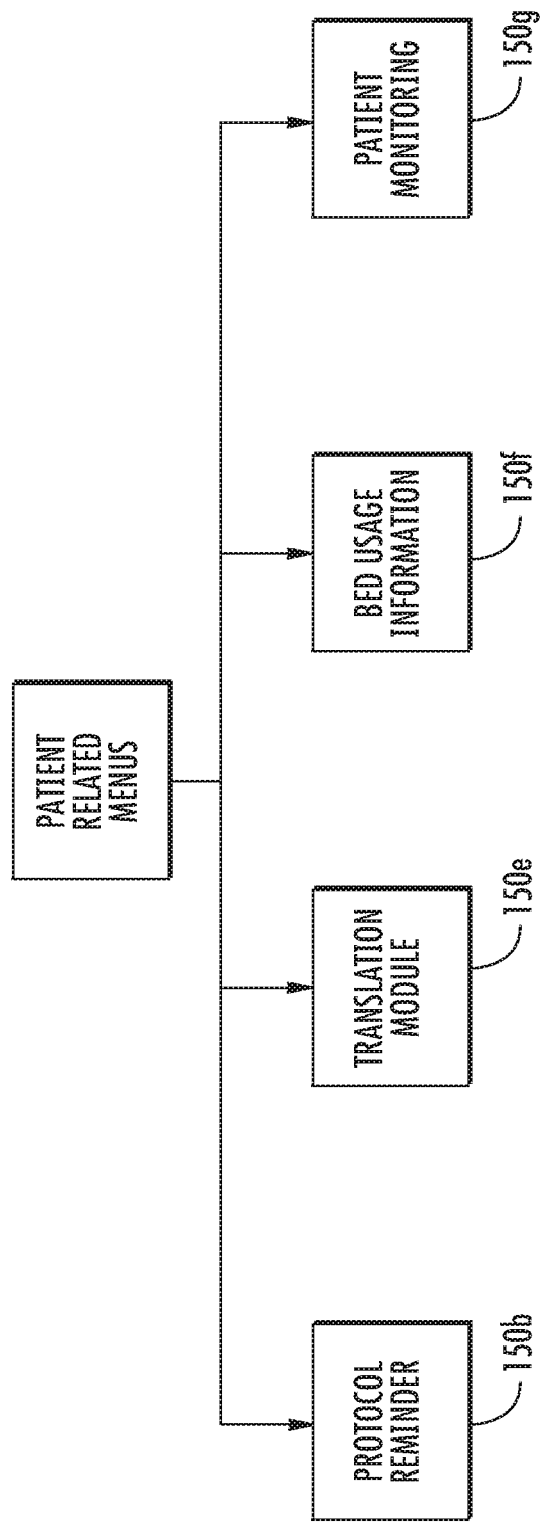
FIG. 50 illustrates a flowchart of additional features that may be provided by the control system of the present invention.

Referring to FIG. 50, the control system of the present invention may provide additional features. These features may be added to the controller software or may be added by modules that are coupled to the bed control system and in communication with the controller. For example, additional or expanded menus, such as patient related menus may be provided, such as an expanded protocol reminder menu 150b, an expanded translation module menu 150e, a bed usage information menu 150f, and a patient monitoring menu 150g.

Figure 51:
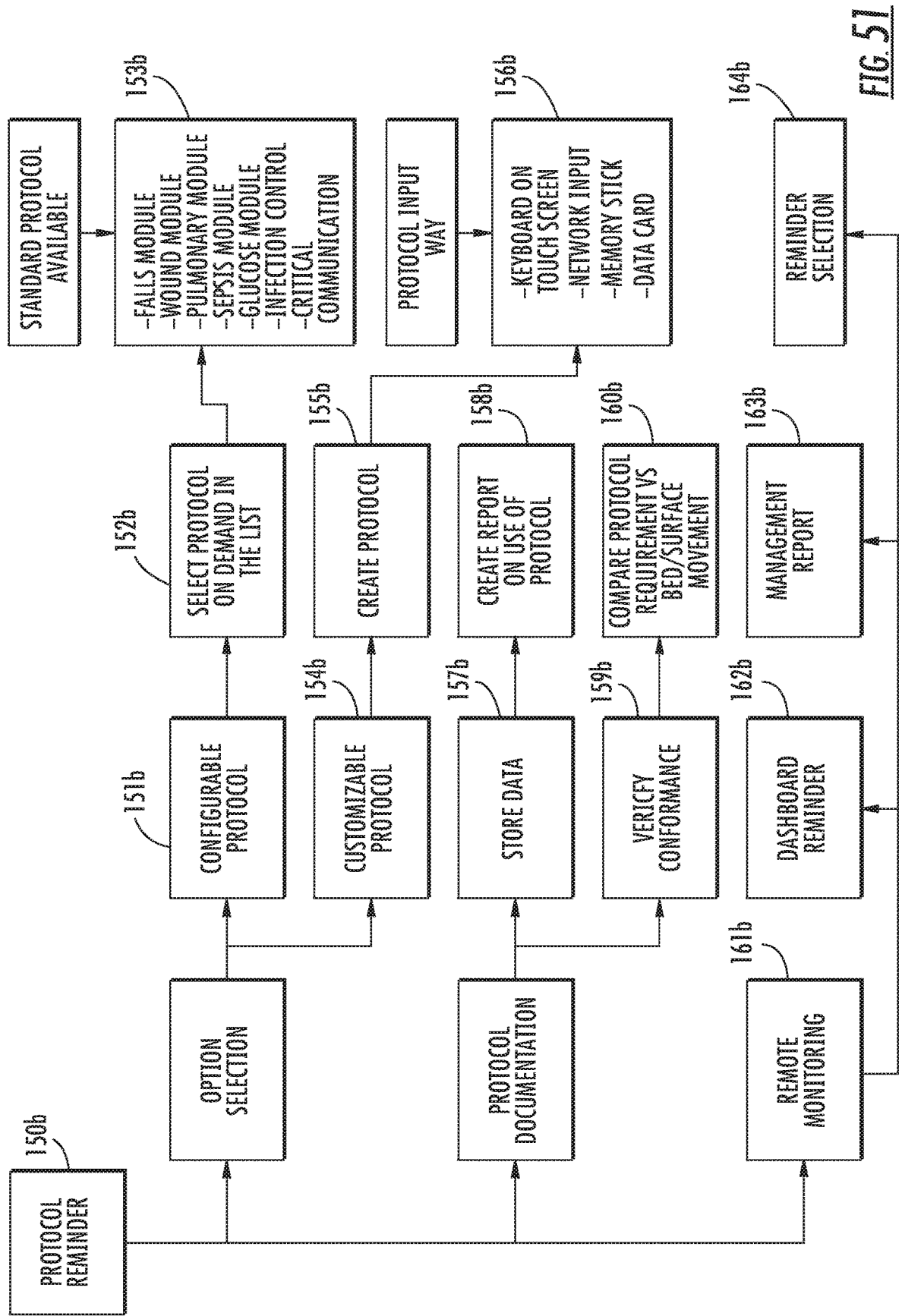
FIG. 51 is a flowchart illustrating a further refinement of a protocol reminder menu or module.

Referring to FIG. 51, the expanded protocol reminder menu 150b may allow a user to add (151b-153b) or create (154b-156b) a protocol. As noted above, standard protocols may be stored in the controller, which may be selected by the user. The protocols may be increased by uploading additional protocols or providing additional modules that provide other functionality. When new protocols are to be added to the control system, the protocols may be created using an input device (156b), such as a keyboard, or input from a network or through a USB port, using a memory stick or data card or the like. For example, the controller may generate a "create new protocol" icon, which once selected would allow a user, using the keyboard at the touch screen or another key board at the control module, to key in the name of the protocol code, which then prompt the controller generate an icon at the display that represented that protocol. Once the name of a new (whether keyed in or uploaded) the new protocol is stored in the controller, and the new protocol will then be displayed on the list of protocols that can be then selected by the user using the routine described above.

In this manner, the protocol reminder menu 150b provides an expanded choice of functions and protocols that can be monitored and prompted and displayed at display 38.

In addition, protocol reminder menu 150b may also provide an option to document protocols. For example, the controller may be configured to store data (157b) associated with a protocol. Further, the controller may be configured to store the type and occurrence of a protocol reminder and whether the protocol was followed by the healthcare worker as indicated by an acknowledgement entered by the healthcare worker. For example, when a healthcare worker takes the associated action or actions associated with a protocol, the healthcare worker may indicate to the controller that the sequence or acts associated with the protocol are complete. This may be achieved through a user interface, which may be provided on the display, such as a touch screen area of the display, or on a separate button provided at control panel 38 that when selected indicates that the protocol sequence was followed. In addition, the controller may store the time entry of the acknowledgement. In addition, the controller may produce a report based on the data collected with regard to the protocols.

Further, the controller may have stored therein data related to one or more of the protocols to compare the collected data to the data stored for the respective protocol to verify conformance (159b). In addition, as noted above, control system may provide remote monitoring (161*b*) and in communication with a remote device, such as a nurses' station to allow remote monitoring of the protocols. Furthermore, the remote device may collect data from the controller to create a separate report or to download the report that is generated by the controller (163*b*). In addition, the remote device may select a protocol reminder to be displayed at display 38 and/or to be displayed at the remote location, such as the nurses' station (164*b*).

Figure 52:
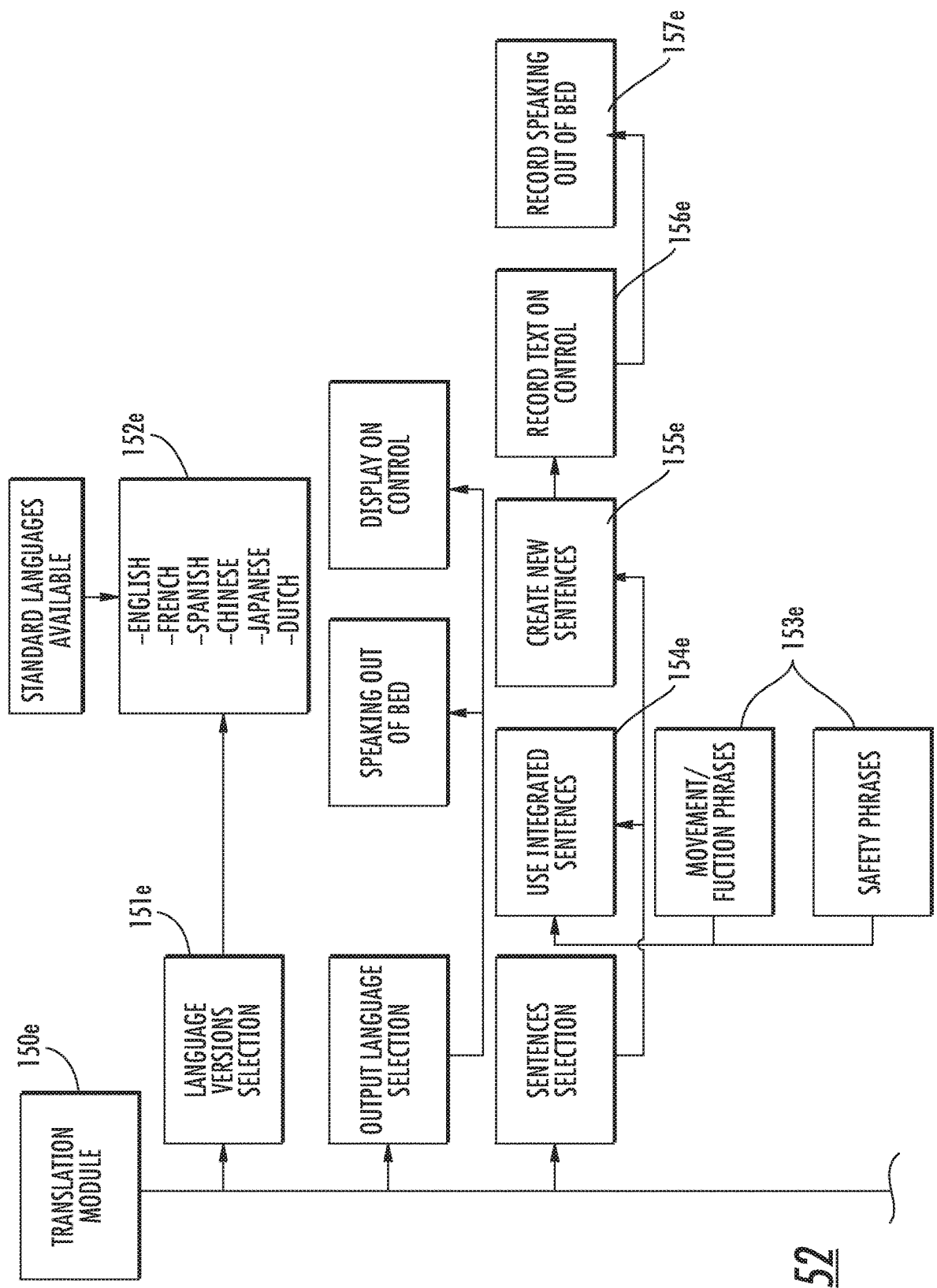
FIG. 52 is a flowchart illustrating the features of an optional translation module.

Referring to FIG. 52, translation module menu 150*e* similarly provides a user to select a language (151*e*) into which the input phrase is translated. For example, a standard set of language may be stored on the controller, which may include for example, English, French, Spanish, Chinese, Japanese, Dutch, or the like (152*e*). Similar to translation module 50*e*, translation module 150*e* may include a choice of phrases (153*e*), which may be selected for translation and may further include a database of words (154*e*) that may be selected to create a sentence (155*e*). For example, the words may be combined together or may be combined with the pre-stored phrases, such as movement or function phrases or safety phrases to be integrated into a sentence, which is then translated. These new sentences may then be stored on the controller (156*e*). Furthermore, as previously noted, the control system may optionally include a voice recorder and player so that one or more of the phrases or constructed sentences may be recorded (157*e*) and, further, played at the patient support (158*e*). In addition to selecting the language of the text to be displayed at display 38, the language of the recording being played at the patient support may also be selected. For example, a pre-selected group of recordings in the various foreign languages available on the controller may be recorded and played at the patient support, which may be particularly useful when dealing with a patient that does not speak the language of the caregiver. For example, a selection of basic phrases in any one of the languages of choice on the controller may be recorded and selected by the healthcare worker. Likewise, a selection of a plurality of phrases in the various languages available on the controller may be stored for use by the patient. For example, the patient may select from a languages with the various phrases available for their selection either in text display or to be played by the speaker of the recording/player device.

Figure 53:
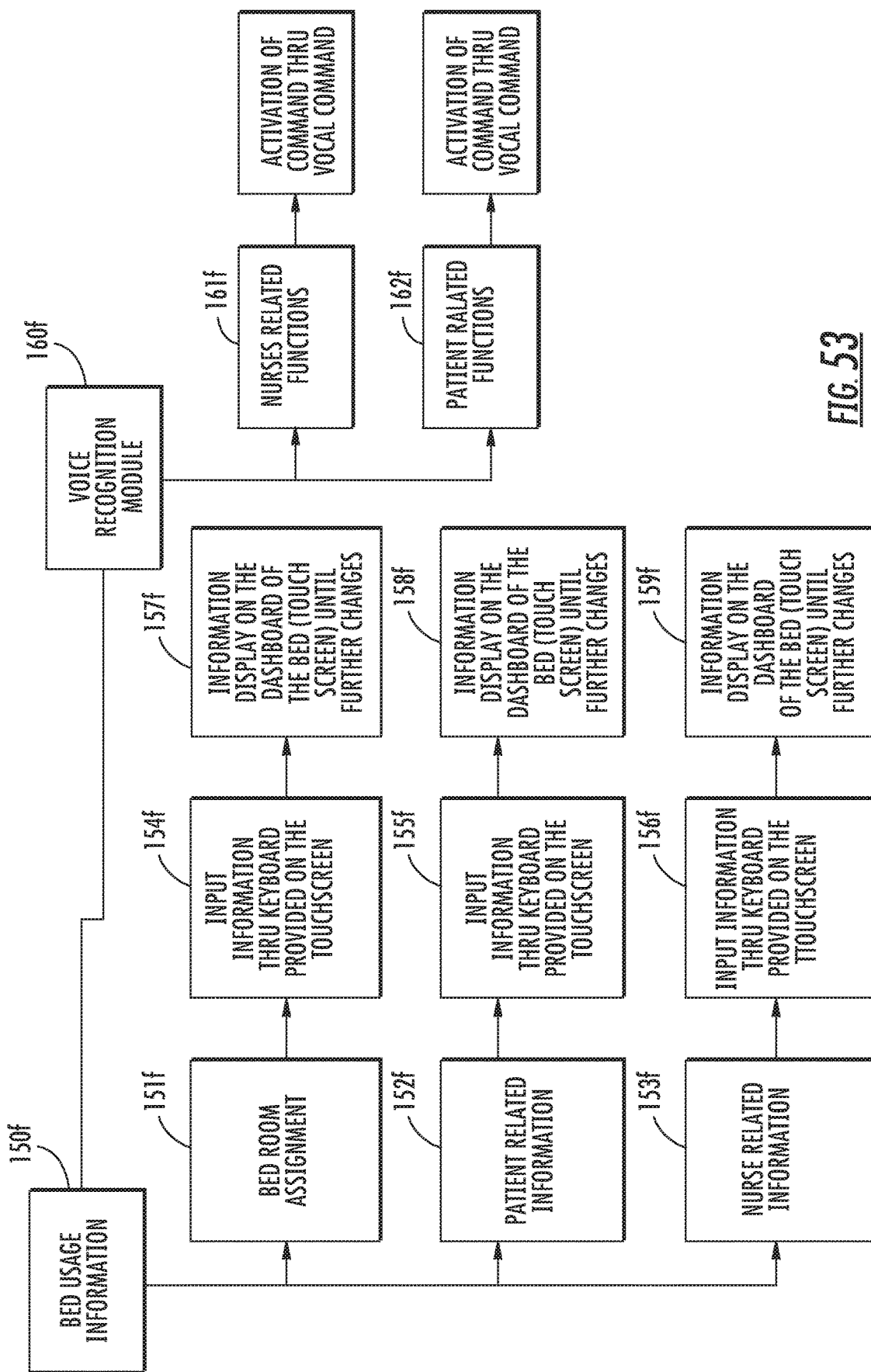
FIG. 53 is a flowchart illustrating a bed usage information module that may be used by the control system of the present invention.

Referring to FIG. 53, as noted above, bed usage information (150*0*) may be input into the controller. For example, the bed room assignment (151*f*), patient related information (152*0*), and nurse related information (153*0*) may be input into the controller. For example, the bed room assignment information, patient related information, and nurse related information may be input into the controller using a keyboard (154*f*-156*0*), such as a keyboard, such as a virtual keyboard, provided on the touch screen. Further, this information may be displayed (157*f*-159*0*) at display 38, for example until additional information is input into the controller.

In addition, the control system of the present invention may incorporate a voice recognition module 160*f*. Voice recognition module 160*f* includes a speaker and, further, voice recognition software, which allows a user to speak into the microphone and have the speech converted into input by the software for controlling various features on the bed. For example, the voice recognition module may include a speaker that is located for the patient's use as well as a speaker available for use by the healthcare provider. For example, instructions received at the patient's microphone (162*0*) may be used to control various features on the bed, such as the elevation of the head section or the foot section of the bed, or accessories at the bed, such as a light, TV, radio, or the like, or to activate the nurse call system. In contrast, the microphone located at the, for example, foot end of the bed for use by healthcare worker, may be used to control the orientation of the bed with some additional expanded options, for example to move the bed into a Trendelenburg or reverse-Trendelenburg position. For example, a healthcare worker may input commands to the voice recognition module to adjust the firmness of the bed, to initiate rotational, vibration, or percussion therapy, etc.

Figure 54:
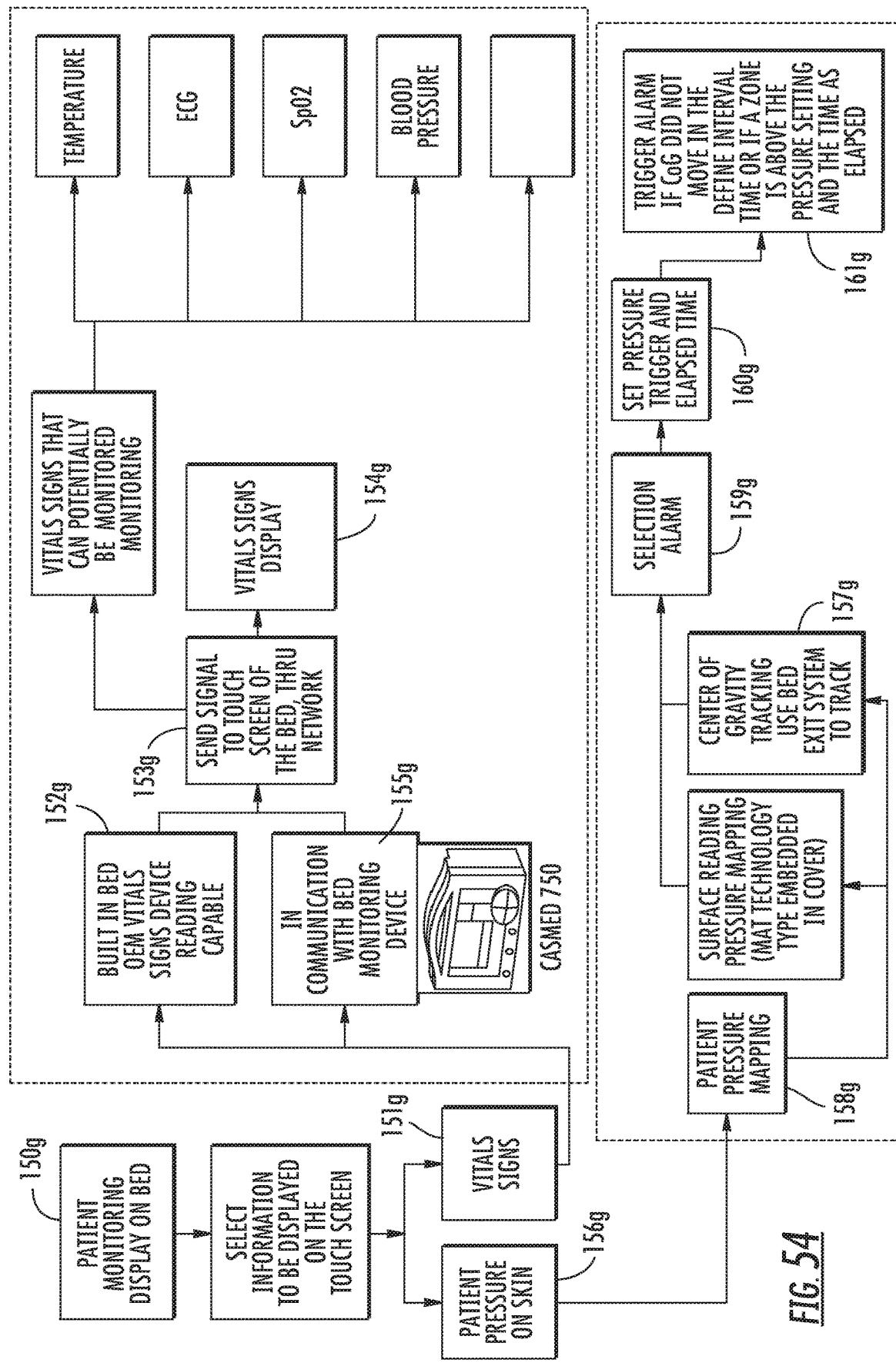
FIG. 54 illustrates a flowchart of patient conditions that may be monitored by the control system of the present invention.

Referring to FIG. 54, the patient monitoring functions (150*g*) may also be displayed at display 38. For example, as previously noted, the patient's vital signs (151*g*) may be displayed at display 38. The vital signs may be collected by a bed base vital signs device (152*g*), which is incorporated into the control system and which generates signals to the controller, which in turn communicates the signals to the display through the bed network (153*g*) for displaying at display 38 (154*g*). Alternately, a commercially available vital signs monitoring device (155*g*), such as a CASMED 750 available from Philips, may be coupled to the bed network, which generates signals to the controller again for display at display 38 (154*g*). For example, suitable vital signs may include the patient's temperature, ECG, SpO2 patient's blood pressure, or the like. This may be displayed in the form of a text or graphical form.

In addition to monitoring vital signs, the control system on the bed may monitor the pressure on the patient's skin (156*g*). For example, as previously noted, the control system may include load cells, which can be used to indicate the location of the patient on the bed and, further, indicate whether there is a likelihood of a high pressure zone on the patient's body. Further, the patient support may incorporate pressure sensors in the mattress or on top of the mattress in the form of a matt, which may be used to generate a pressure map (158*g*), which in turn may be used to locate high pressure points on the patient. Knowing the pressure points on the patient support surface may enable the healthcare worker to know whether a particular part of the patient's body is vulnerable to forming sores and needs to be moved. For example, the controller may include a set pressure point and a set time (160*g*), which when exceed indicates that the patient is vulnerable to a bed sore. When the controller detects a high pressure point, the controller may trigger an alarm (161*g*) so that the healthcare worker may adjust the position of the patient on the bed. For example, the controller may initiate an alarm when a high pressure point is detected, and, further, only after a pre-selected period of time has elapsed. This may be achieved by storing on the controller a look-up table of pre-selected pressure point values, which when exceeded trigger the alarm. Further, a matrix may be stored on the controller, which includes time periods and pressure points values, which define different combinations of pressure point values and time periods to serve as the trigger.

Similarly, the controller may trigger an alarm when the load cells indicate a lack of activity on the part of the patient. For example, as previously noted, the load cells may be used to track the center of gravity of the patient with the control and monitoring the movement of the center of gravity (157*g*) to determine whether the patient is moving. If the controller determines a patient has not moved for a period of time that exceeds a maximum time period (which is stored in the controller), the controller may then trigger an alarm.

As noted above, the controller may, in response to the input from a button 40*a*, generate drive signals for one or more of the actuators on the bed, for example, the actuator 29 that moves the brake of the caster to a brake, neutral or steer position.

Figure 15:
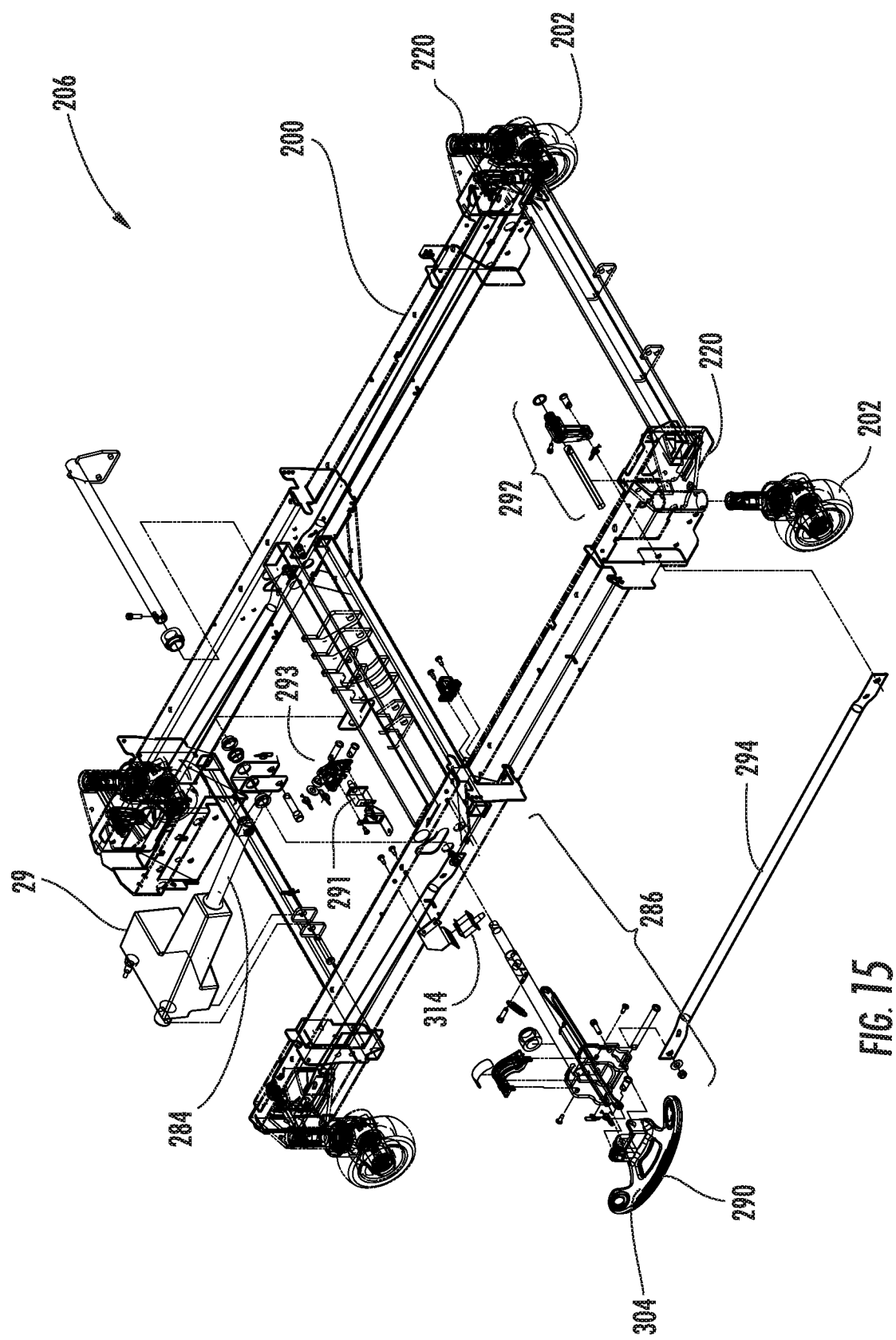
FIG. 15 is an exploded perspective view of the base frame and braking system.

As described in the referenced applications and illustrated in FIGS. 15 and 15A-15O, in order for the bed to be mobile to enable transport of the bed and/or patient from one location to another, a plurality of bearing members, such as wheels or caster devices, including casters or caster wheel assemblies 202, may be provided to enable bed mobility. In this particular embodiment, four casters or caster wheel assemblies 202 are provided and pivotally mounted to the base frame 200 by means of respective mounting brackets 220 secured in a conventional manner to the corners of the base frame 200. Further, each caster includes operatively associated therewith a brake, which are well known in the art and available, for example, from Tente.

For example, the controls may be configured to provide three operating states: a brake state, wherein the casters 202 are locked (e.g. both from turning and from pivoting), a neutral state, wherein the casters 202 are free to move and driving and maneuverability of the bed is achieved manually, and a driving or steering state, wherein the casters 202 are again free to move and wherein the drive wheel mechanism is actuated to bring the drive wheel in operative engagement with the floor and the drive controls (discussed below) are activated. It will be understood that a variety of other methods and systems can be used to activate and operate the above and other such drive wheel systems, and that such alternative methods and systems should not be considered to depart from the general scope and nature of the present disclosure.

In one embodiment, illustrated for example in FIGS. 15 and 15A-15O, the braking system 206 generally comprises a low force braking system for reducing the force needed by a user to activate and deactivate the braking system 206. For instance, the bed may comprise a power-assisted or actuated breaking system 206 (e.g. as described below) to facilitate an operation of the bed using various available steering and/or braking features of this mechanism. In addition, such systems may further comprise one or more hand and/or foot actuated manual override mechanisms (e.g. see FIGS. 15A-15O) in the event of a power failure, for example. Contemplated brake system control means may include, but are not limited to, power-assisted hand and/or foot brakes, such as handles or pedals, user actuatable devices, such as a button, a touch screen, and/or a switch, on one or more control panels provided on or near the bed, and other such controls powered electrically, hydraulically, pneumatically and/or magnetically, as will be readily understood by the person skilled in the art.

Figure 13:
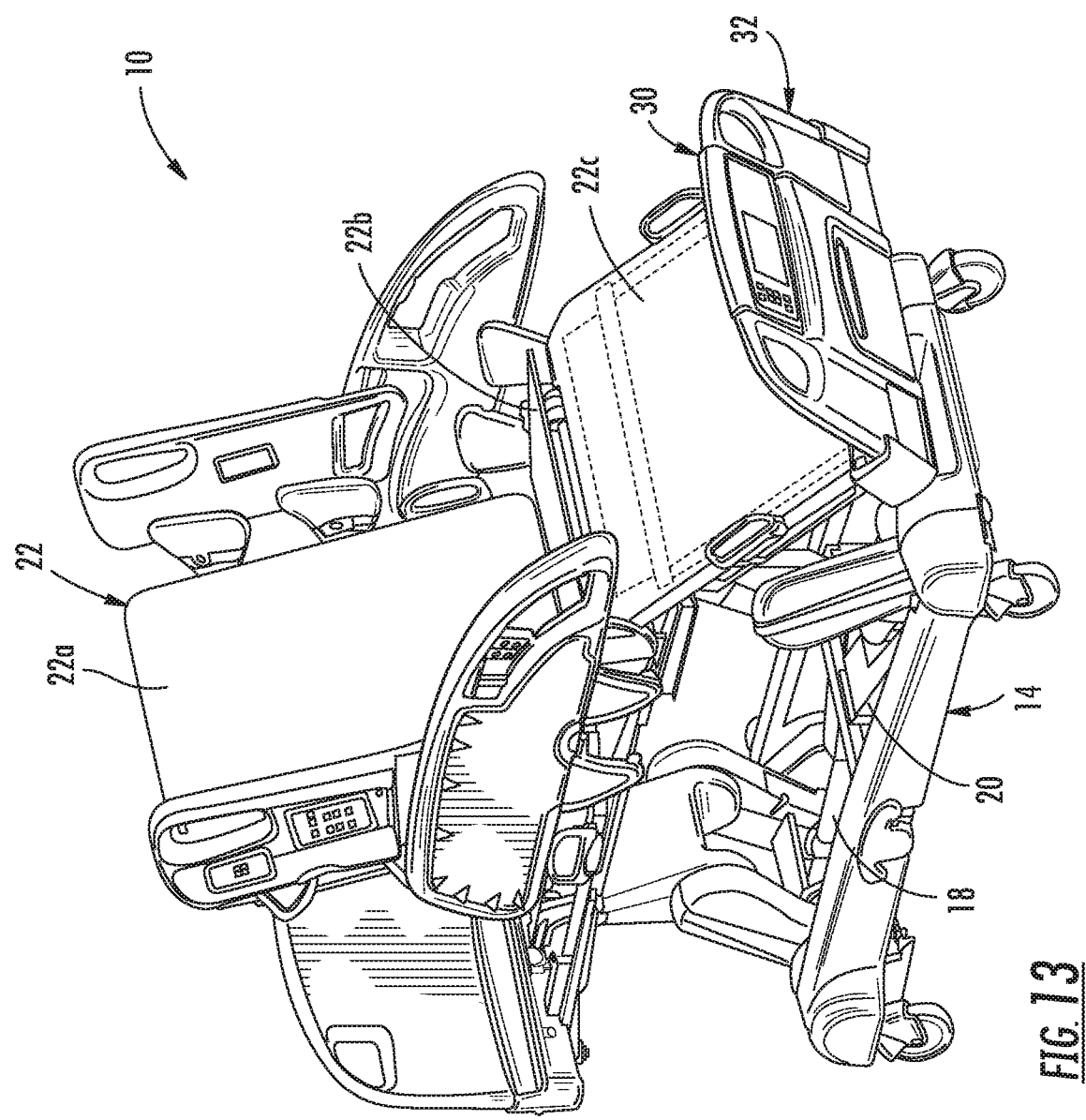
FIG. 13 is another perspective view of the patient support illustrating the deck articulated to provide a sitting position for the patient.
Figure 14:
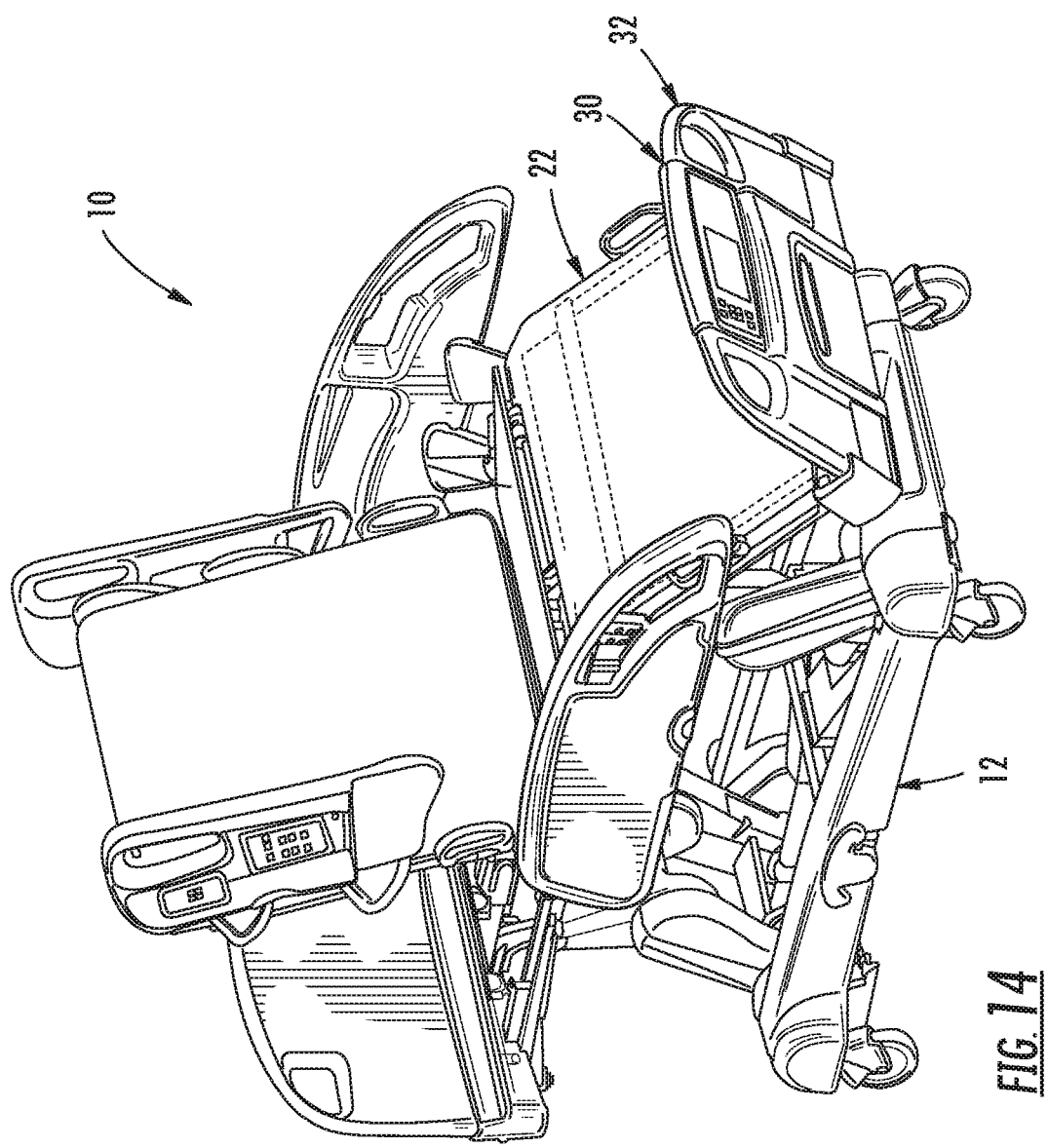
FIG. 14 is a similar view to FIG. 13 illustrating the deck in an articulated position with one of the side rails lowered.

For example, in one embodiment, the user can activate the brakes on one or more control panels (e.g. see FIGS. 1, 2 and 13) located, for example, on the exterior of the head-end or foot-end side rails and/or on the head-end structure, within the vicinity of the push handles, as depicted for example in the referenced applications and patents. Access to the brake activation can also be available on other control panels, including for example, a footboard control console, other interfaces, or a removable panel, and the like. The positioning of the brake controls on one or more control panels allows the user to more easily access and activate the braking system 206. For instance, in some embodiments, the positioning of the bed's side rails and/or the positioning of the bed itself (e.g. when the bed is in a lowered position) may impede access to a manual brake activation pedal or handle (e.g. brake pedal 290 of FIGS. 15A-15O). Using controls disposed on one or more control panels, however, the braking system 206 may still be readily accessed and controlled.

Furthermore, automatic brake control via the bed control system (numeral 1000 in referenced parent patents) can also provide a safety feature when the system is in a motion lockout, further discussed in the parent patents. In a total lockout of motion, a lock mechanism prohibits movement functions from being controlled on the control panel(s), located for example on the side rails, footboard, pendant and headboard, etc. The brake can be set during the lockout but, for safety reasons, preferably cannot be removed at any point during a total lockout.

In one embodiment, the brake control(s) is located proximate the push handles (for example handles numbered 451 in parent patents) and can be engaged or disengaged without removing the user's hands from the handles. For example, the bed generally rolls in the direction guided by the user who is controlling one or more of the push handles. When force is not exerted on the handles, the drive wheel decelerates, and eventually comes to a halt, usually within 4-10 seconds. While the braking system 206 may be used to assist in bed deceleration, it is usually not required, given the bed's slow speed. Furthermore, if a patient is in the bed, use of the brake during bed displacement may be jerky and uncomfortable. As such, the braking system 206 is typically used to secure an immobile bed, similar to a vehicle's hand brake.

When in use, the user engages the braking system 206 which imparts a braking force directly on the casters 202. The brake can be a cam that pushes on the tire or brake on the axle or separate disk or the wheel itself. The brake system is usable on heavy beds and is adaptable to different braking system (ring, wheel, or direct floor pressure).

Furthermore, the casters 202 may comprise brake casters, selectively operated in free rotation and brake modes, or steer/brake casters selectively operated in free rotation mode, pivotally locked mode and brake mode, wherein actuation of the braking system 206 can implement either immobilization of one or more casters from rotating (e.g. prohibit displacement of the bed) and/or immobilization of one or more casters from pivoting (redirecting a displacement of the bed).

For instance, in one embodiment where a drive wheel mechanism is provided (e.g. such as the drive wheel mechanism described above), the bed may be operated in three states, a braking state wherein the casters 202 are rotatably and pivotally immobilized, a neutral state where the casters 202 are free to move in either direction, and a steering state wherein the casters 202 are still free to move in either direction while a drive wheel mechanism is activated. In another embodiment where a drive wheel mechanism is not provided, the bed may again be operated in three states, braking and neutral states as above, and a steering state wherein the foot-end casters 202 (or head-end casters if the bed is commonly operated from the foot-end) are pivotally immobilized while the head-end casters 202 can move freely. Other combinations and permutations of the above breaking and steering options may also be considered, as will be apparent to the person skilled in the art. Selection of the brake mechanism's state may be implemented using conventional means, such as a manually operated handle and/or pedal, or again via electronic controls (e.g. provided via control panels or the like).

For example, in one embodiment, three push buttons corresponding to brake, steer and neutral modes are provided on one or more control panels (e.g. see FIGS. 1, 2 and 13) to selectively operate the braking system 206. These buttons may be operatively coupled to one or more actuators, such as in actuator 29 of FIGS. 15, 15A-15O, configured to activate or deactivate the braking system 206. A manual override system 208 may also be integrated into the braking system 206 and may include, for example, a manually actuated pedal, as in pedal 290 of FIGS. 15A-15O, or the like.

The exemplary braking system 206 depicted in FIGS. 15 and 15A-15O will now be described in greater detail. The braking system 206 is generally configured to immobilize the casters 202 from rotating such that a displacement of the bed is substantially mobilized, and/or from pivoting such that a direction of the caster 202 is stabilized to facilitate, for example, steering of the bed. In the latter case, pivotal braking may be limited, for example, to two of the four casters 202 such that an operator of the bed may select an orientation of the bed displacement by pivoting two of the casters 202, while using the pivotally locked casters 202 to facilitate this directional displacement.

In the embodiment illustrated in FIG. 15, the braking system 206 is configured such that a motorized control of the system 206 is imparted via a single motor or actuator 29. In particular, the actuator 29, controlled or operated from one or more control means such as brake handles, user actuatable devices, such as push buttons and the like, as described above, is used to mechanically activate a locking mechanism on each of the casters 202. For example, a nurse may activate the brakes from the push handles. In an optimal form, the nurse may activate the brakes without removing his/her hands from the push handles. A person of skill in the art will understand that, although the present embodiment is described as including a single actuator 29, such as an electric, a pneumatic, a magnetic, or a hydraulic actuator, for all four casters 202, a similar braking system 206 could be designed to include one such actuator for each caster 202, or again, one actuator for each two casters 202 (e.g. an actuator to control the head-end casters 202 and a second actuator to control the foot-end casters 202). Other combinations of actuators for any number of casters may also be contemplated herein without departing from the general scope and nature of the present disclosure, as will be readily understood by the person skilled in the art.

Figure 15D:
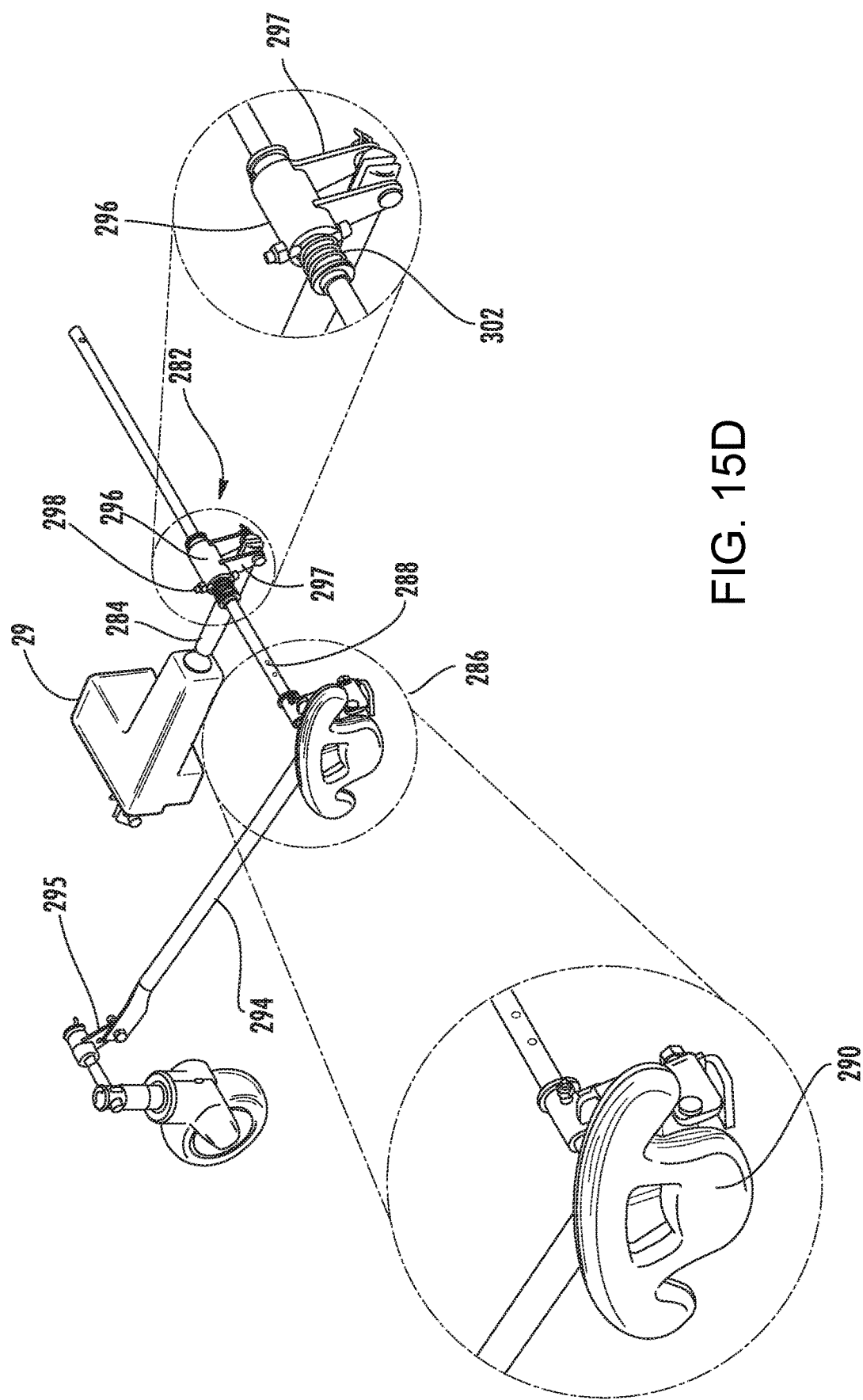
FIG. 15D is a right perspective view of the braking system in a steer position showing in details A and B central and lateral levering mechanisms thereof respectively.

Referring to FIG. 15D, the braking system 206 generally comprises a central levering mechanism 282 operatively interconnecting a driven member 284 of actuator 29 to lateral levering mechanisms 286 on each side of the base frame 200 via a transversal shaft 288. The lateral levering mechanisms 286, the right-hand side one of which is illustratively coupled to a manual override actuation pedal 290, are themselves configured to actuate the brake mechanism 292 on each caster 202 via longitudinally extending brake actuator bars 294 configured such that a substantially linear displacement thereof pivots respective brake actuating levers 295 configured to operate the respective brake mechanisms 292 of each caster 202. Contemplated brake mechanisms 292 may include, for example, a locking cam or the like configured to selectively immobilize a given caster 202 from rotating and/or pivoting, depending on the type of caster used. It will be understood that other braking mechanisms may be considered herein without departing from the general scope and nature of the present disclosure. As noted, commercially available braking mechanisms are available from Tente. Furthermore, different braking mechanisms 292 may be used for different casters 202, depending on the intended purpose and use of such brake mechanisms.

Figure 15E:
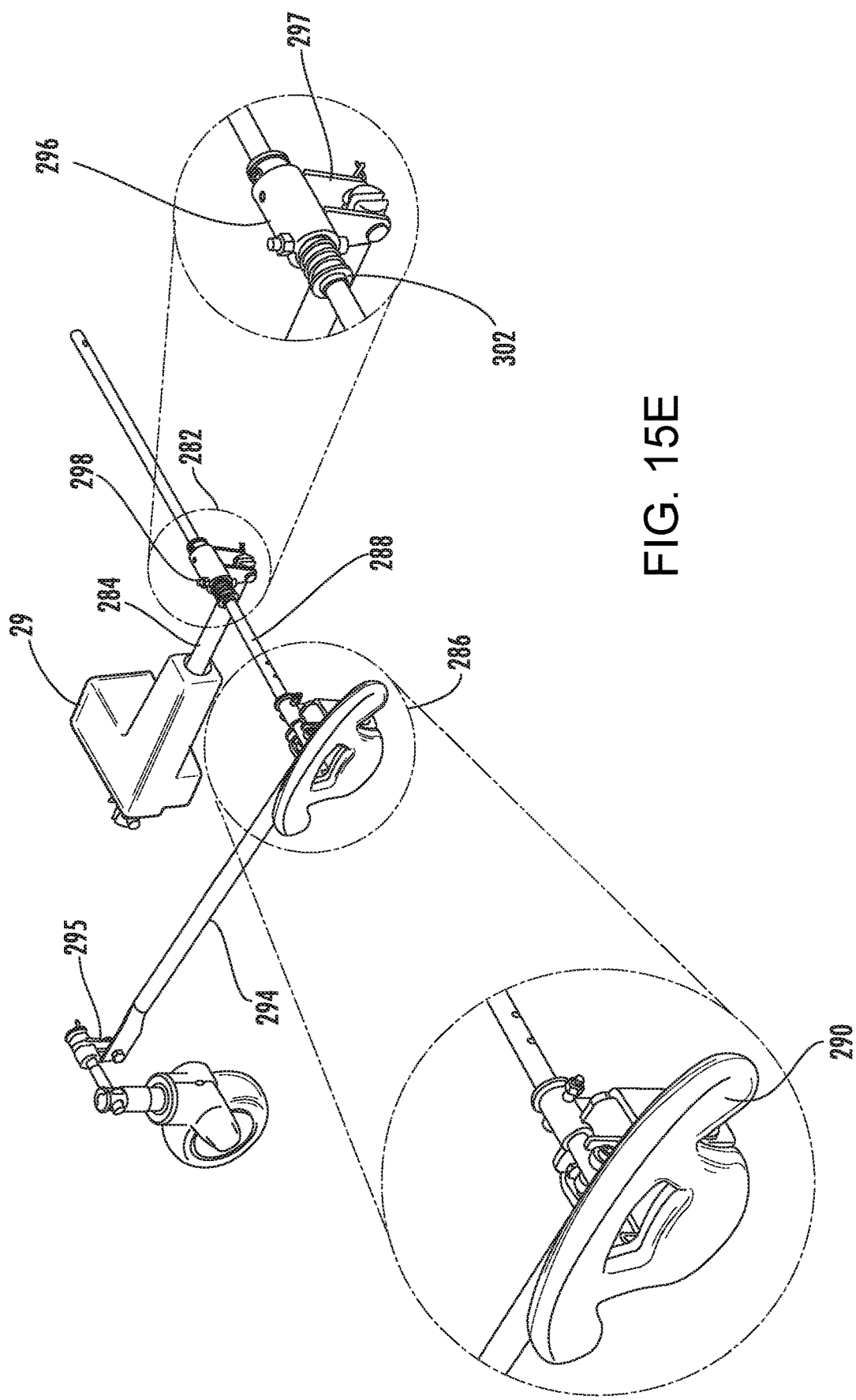
FIG. 15E is a right perspective views of the braking system in a neutral position showing in details A and B central and lateral levering mechanisms thereof respectively.
Figure 15F:
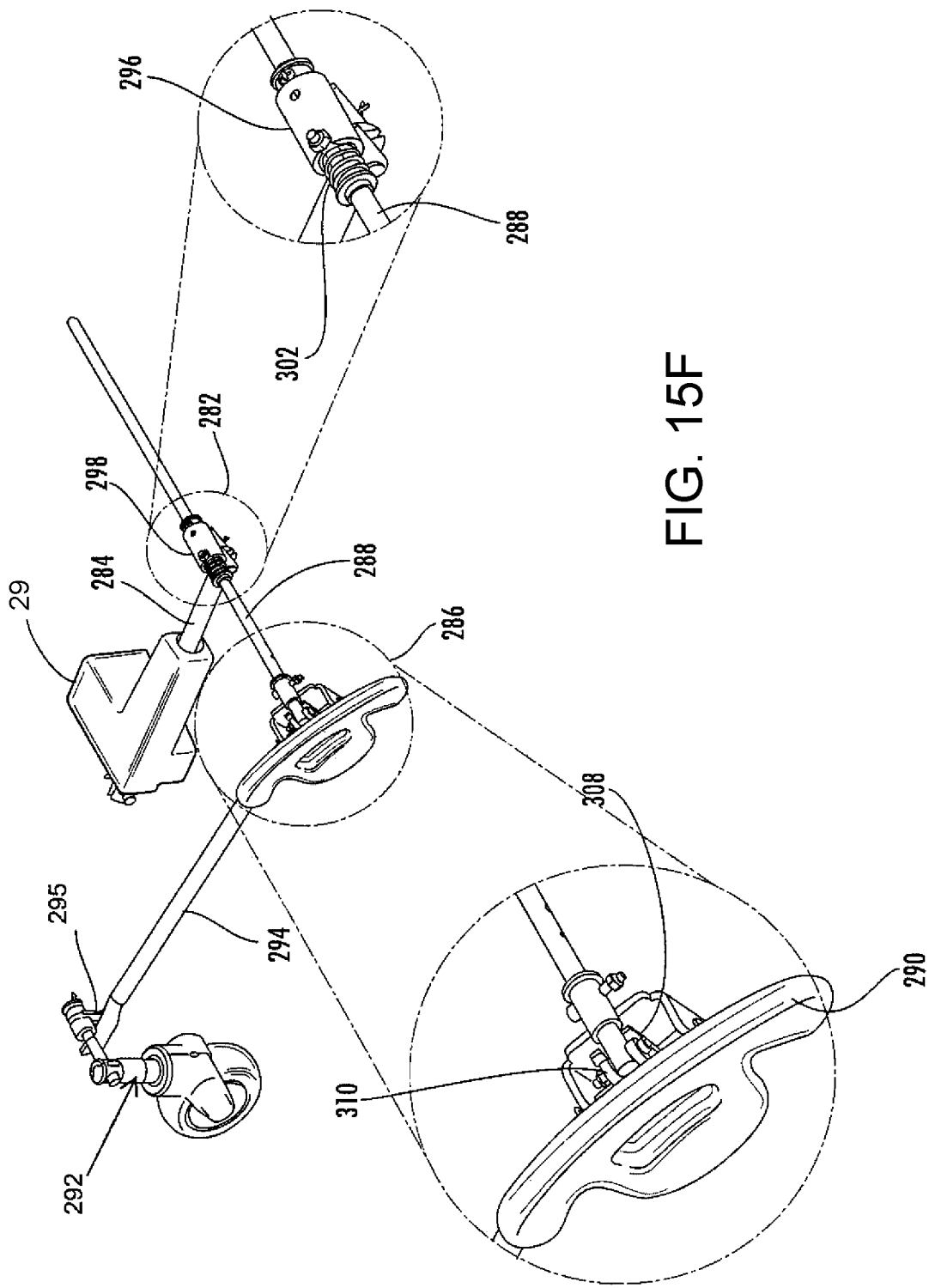
FIG. 15F is a right perspective view of the braking system in a brake position showing in details A and B central and lateral levering mechanisms thereof respectively.

Referring to FIGS. 15D-15F, in particular, the central levering mechanism 282 comprises a sleeve member 296 that is slid toward the center of shaft 288 and coupled to the driven member 284 via flanges 297 extending radially outward therefrom. A bolt or pin 298 is further provided through the shaft 288 and biased within a notch 300 formed in through a periphery of the sleeve 296 by a spring mechanism 302, thereby operatively coupling the sleeve 296 to the shaft 288 when the pin 298 is so biased, such that a rotation of the sleeve 296 under a pivoting action applied to the flanges 296 by the driven member 284, induces a rotation of the shaft 288. As will be described below, when the override pedal 290 is deployed, the shaft 288 is shifted toward the right such that the pin 298 is released from the notch 300, thereby uncoupling the shaft 288 from the sleeve 296 and allowing for manual operation of the caster brake mechanisms 292.

The shaft 288 extends across the base frame 200 and through to the lateral levering mechanisms 292 such that a rotation of the shaft 288 imparts a substantially linear displacement of the bars 294. As recited above, displacement of the bars 294 generally translates into operation of each caster's brake mechanism 292 via respective brake actuating levers 295. A protective cover 299 may also be provided to hide and possibly protect the bars 294 and other elements of the braking system 206.

As introduced above, an override pedal 290 is provided on the right-hand side of the bed and is operatively coupled to the lateral levering mechanism 286 on this side. In general, the override mechanism is practical in situations where the actuator 29 is in a given position and power thereto or to the control system is unavailable, thus preventing the actuator 29 from changing from one mode to another. In one embodiment, the pedal 290 is spring-biased in an upright and stowed position (e.g. FIGS. 15A-C) such that a downward pivoting force is required to extend the pedal 290 to an operable position in which an operating surface thereof 304 is substantially parallel with the floor (e.g. FIG. 15G). Furthermore, the pedal 290 may be configured such that when it is stowed, a clearance of about five inches is maintained below the pedal 290 irrespective of the pedal's orientation. Although this clearance may be obstructed when the pedal 290 is engaged, the clearance is regained automatically as the pedal 290 is returned to its stowed position.

When such a force is applied to the pedal 290, a corresponding set of pivoting flanges 308 are configured to pivot and engage a bolt 310 transversally fastened through the end of the shaft 288 such that the shaft 288 is pulled toward the pedal side of the bed, thereby releasing the pin 298 from notch 300 and disengaging the actuator 29 from operative control of the braking system 206. As a result, control of the braking system 206 is then provided via the deployed pedal 290 rather than the motorized actuator 29 and controls thereof. When the foot or hand of the operator releases the pedal 290, the latter springs back to its upright position and the pin 298 is again urged toward the notch 300 by the spring mechanism 302.

In one embodiment, the release of pedal 290 is monitored by a switch 291 configured to report to the control system, whether the braking system 206 is currently in override mode. For example, as shown in FIG. 15, as the shaft 288 is pulled toward the pedal 290, a levering mechanism 293 may be configured to release a user actuatable device, such as a switch 291, indicating that the braking system 206 is in override mode. When the pedal 290 is released to its upright position, the switch 291 is pressed and reports this event to the control system, which may then activate the actuator 29 to pivot the central levering mechanism 282 through its course thereby rotating the sleeve member 296 to realign the notch 300 therein with pin 298 so to re-couple the actuator 29 with shaft 288. Alternatively, the pin 298 may be re-engaged with the notch 300 by manual rotation of the released pedal 290, or again by a control user actuatable device, such as a button or switch, provided therefor with the control system.

In one embodiment, a visual indicator 312 is also provided above the pedal 290 and configured to indicate a status of the braking system 206 as the breaking system 206, and consequently the pedal 290, is moved through different positions (e.g. brake, neutral, steer), either manually or automatically via the control system. A sensor 314, such as a user actuatable device, such as a button or switch or the like, may also be provided to report a brake status to the control system, which may be conveyed to the operator via one or more visual user interfaces, as described further below. In general, the brake status indicator(s) may help to avoid having the user inadvertently leave the bed without the brakes being set, which could result in inconveniences or safety concerns for the patient.

FIGS. 15A to 15C shows a change of the visual indicator 308 and a motion of the pedal 290, when stowed, as the braking system 206 is selectively moved from steer, neutral and brake positions respectively.

FIGS. 15D-15F show an automatic actuation of the braking system 206 in steer, neutral and brake positions respectively. For instance, in FIG. 15D, the actuator 29 fully extends the driven member 284 to pivot the handle 290 toward the head-end of the bed, thereby moving the bars 294 toward the foot-end of the bed, which in turn positions the caster breaking systems 292 in steer mode. In one embodiment, steer mode implies that all casters 202 are free to rotate and pivot, for example when a drive wheel mechanism is used. In another embodiment, steer mode implies that only head-end casters are free to rotate and pivot, while foot-end casters are pivotally immobilized. In the latter case, selecting the steer mode may pivotally immobilize the foot-end casters in their current orientation until a push or pull force is applied to the bed, at which point these casters will orient themselves with an axis of the bed and lock to maintain this orientation as they rotate.

In FIG. 15E, the actuator 29 partially extends the driven member 284 to level the handle 290, thereby centering the bars 294, which in turn positions the caster breaking systems 292 in neutral mode. In one embodiment, neutral mode implies that all casters 202 are free to rotate and pivot.

In FIG. 15F, the actuator 29 fully retracts the driven member 284 to pivot the handle 290 toward the foot-end of the bed, thereby moving the bars 294 toward the head-end of the bed, which in turn positions the caster breaking systems 292 in brake mode which immobilizes the casters 202. During operation when the bed is not moving, users typically engage the braking system 206. Users can visually verify the status of the brake position with the status indicator 312, depicted in FIGS. 15A-15C.

FIGS. 15G-15O illustrate the manual override of the braking system 206, wherein the pedal 290 is deployed, generally by the foot of a user, though hand operation may also be contemplated. In general, as introduced above, when the pedal 290 is deployed, the pin 298 is released from notch 300 thereby uncoupling the actuator 29 and the shaft 288.

The pedal 290 can then be used to manually override the braking system 206 using foot or hand actuation. In FIGS. 15G-15I, the actuator 29 coupling to the shaft 288 is released when in the steer position and remains in this position while the pedal 290 is moved from a brake position (FIG. 15G), through a neutral position (FIG. 15H), to a steer position (FIG. 15I). In FIGS. 15J to 15L, the actuator 29 coupling to the shaft 288 is released when in the neutral position and remains in this position while the pedal 290 is moved from a brake position (FIG. 15J), through a neutral position (FIG. 15K), to a steer position (FIG. 15L). In FIGS. 15M-15O, the actuator 29 coupling to the shaft 288 is released when in the brake position and remains in this position while the pedal 290 is moved from a brake position (FIG. 15M), through a neutral position (FIG. 15N), to a steer position (FIG. 15O).

As stated above, when the pedal 290 is released, the pin 298 is again urged toward the sleeve member 296 such that as the sleeve 296 is rotated about the shaft 288 by activation of the actuator 29, the pin 298 eventually re-engages the notch 300 therein, thereby re-coupling the actuator 29 to the shaft 288 and caster braking mechanisms 292. Alternatively, the shaft 288 and pin 298 can be rotated manually using the stowed pedal 290 until the notch 300 is re-engaged by the pin 298.

Accordingly, the present invention provides a patient support that incorporates a control system which provides enhanced control over one or more the bed functions and further over information relating to the bed and to the patient. Further, the controller allows the user to select a protocol for the patient and further have the control system remind the user of the protocols. Additionally, the control system allows the user to store and review patient data to help to define better treatment for the patient or define trends about the patient's healing process.

While several forms of the invention have been shown and described, other forms and features will now be apparent to those skilled in the art. For example, the various components of the apparatus, such as the side rails, footboard, and headboard, as well as the elevation mechanism and deck actuators may be modified. Therefore, it will be understood that the embodiments shown in the drawings and described above are merely for illustrative purposes, and are not intended to limit the scope of the invention which is defined by the claims which follow as interpreted under the principles of patent law including the doctrine of equivalents.

We claim:

1. A patient support apparatus comprising:
   a deck for supporting a mattress thereon, the deck having a fowler section for supporting a head end of the mattress, said fowler section having a fowler angle and being movable to adjust the fowler angle;
   a controller;
   a sensor detecting the fowler angle of the fowler section, the sensor operably coupled to the controller;
   a user input operably coupled to the controller, the user input operable to allow a user to select a selected fowler angle, the selected fowler angle comprising a desired state for the fowler section; and
   wherein the controller is operable to monitor the fowler angle of the fowler section and generate an alert when the fowler angle is not in the desired state and further configured to monitor a time the fowler angle has been monitored.

2. The patient support apparatus according to claim 1, further comprising an actuator to change the fowler angle of the fowler section, and the controller is operable to control the actuator to change the angle of the fowler section.

3. The patient support apparatus according to claim 1, wherein the user input is operable to activate the controller to monitor the fowler angle.

4. The patient support apparatus according to claim 1, further comprising a display in communication with the controller, the controller being operable to display at the display the time the fowler angle has been monitored.

5. The patient support apparatus according to claim 4, wherein the user input is at the display.

6. The patient support apparatus according to claim 5, wherein the display comprises a touch screen and includes said user input.

7. The patient support apparatus according to claim 1, wherein the selected fowler angle comprises a range of predetermined angles.

8. The patient support apparatus of claim 1, wherein the controller is operable to monitor and track the fowler angle and determine how long the fowler angle is not in the desired state over a period of time.

9. The patient support apparatus of claim 8, wherein the controller is operable to store data regarding the fowler angle.

10. The patient support apparatus of claim 9, wherein the controller is operable communicate the data to a remote station.

11. The patient support apparatus of claim 8, wherein the controller is operable log the date and time when the fowler angle is not in the desired state.

12. The patient support apparatus of claim 11, wherein the controller is operable communicate the date and time when the fowler angle is not in the desired state to a remote location remote from the patient support apparatus.

13. The patient support apparatus of claim 12, wherein the controller is operable to communicate the date and time when the fowler angle is not in the desired state to a remote station remote from the patient support apparatus.

14. The patient support apparatus of claim 13, wherein the controller is operable to display the date and time when the fowler angle is not in the desired state at the remote station.

15. The patient support apparatus according to claim 1, further comprising an indicator, the indicator generating an indication at the patient support apparatus when the fowler angle is not in the desired state.

16. The patient support apparatus according to claim 15, wherein the indicator comprises a light.

17. The patient support apparatus according to claim 16, wherein the light generates light with a first color when the fowler angle is in the desired state and a second color different from the first color when the fowler angle is not in the desired state.

18. A patient support apparatus comprising:
- a deck for supporting a mattress thereon, the deck having a fowler section for supporting a head end of the mattress, the fowler section having a fowler angle and being movable to adjust the fowler angle;
- a controller;
- a fowler monitoring system including a sensor to detect the fowler angle of the fowler section, the sensor operably coupled to the controller;
- a user input operably coupled to the controller, the user input operable to allow a user to select a selected fowler angle and to activate the fowler monitoring system to monitor the fowler angle, the selected fowler angle comprising a desired state for the fowler section; and
- wherein in response to a user activating the fowler monitoring system with the user input and selecting the selected fowler angle, the fowler monitoring system being operable to monitor the fowler angle of the fowler section and generate an alert when the fowler angle is not in the desired state and further configured to track an amount of time during which the fowler monitoring system is active.

19. The patient support apparatus according to claim 18, wherein the selected fowler angle comprises a range of predetermined angles.

20. The patient support apparatus of claim 18, wherein the controller is operable to determine how long the fowler angle is not in the desired state.

21. The patient support apparatus of claim 18, wherein the controller is operable to store data regarding the fowler angle.

22. The patient support apparatus of claim 21, wherein the controller is operable communicate the data to a remote station.

* * * * *